(12) United States Patent
Aoki et al.

(10) Patent No.: US 11,408,804 B2
(45) Date of Patent: Aug. 9, 2022

(54) PATHOLOGICAL SPECIMEN PREPARATION DEVICE AND PATHOLOGICAL SPECIMEN PREPARATION SYSTEM

(71) Applicant: SEIKO EPSON CORPORATION, Tokyo (JP)

(72) Inventors: Taro Aoki, Niigata (JP); Tadashi Sato, Ugo (JP); Yoichi Suzuki, Yuzawa (JP); Masayuki Kadota, Ugo (JP); Ryo Sato, Yokote (JP)

(73) Assignee: SEIKO EPSON CORPORATION

( * ) Notice: Subject to any disclaimer, the term of this patent is extended or adjusted under 35 U.S.C. 154(b) by 711 days.

(21) Appl. No.: 16/329,539

(22) PCT Filed: Aug. 31, 2017

(86) PCT No.: PCT/JP2017/031401
§ 371 (c)(1),
(2) Date: Feb. 28, 2019

(87) PCT Pub. No.: WO2018/043655
PCT Pub. Date: Mar. 8, 2018

(65) Prior Publication Data
US 2019/0195756 A1 Jun. 27, 2019

(30) Foreign Application Priority Data

Sep. 1, 2016 (JP) .............................. JP2016-170564
Aug. 21, 2017 (JP) .............................. JP2017-158463

(51) Int. Cl.
*G01N 1/38* (2006.01)
*G01N 33/48* (2006.01)
(Continued)

(52) U.S. Cl.
CPC ............... *G01N 1/38* (2013.01); *G01N 1/312* (2013.01); *G01N 1/34* (2013.01); *G01N 33/48* (2013.01);
(Continued)

(58) Field of Classification Search
None
See application file for complete search history.

(56) References Cited

U.S. PATENT DOCUMENTS 5,358,691 A 10/1994 Clark et al.
5,507,410 A 4/1996 Clark et al.
(Continued)

FOREIGN PATENT DOCUMENTS

JP H07-505473 A 6/1995
JP H09-321118 A 12/1997
(Continued)

*Primary Examiner* — Lore R Jarrett
(74) *Attorney, Agent, or Firm* — Harness, Dickey & Pierce, P.L.C.

(57) ABSTRACT

A pathological specimen preparation device includes a stage portion including a stage, a reagent supply portion 150 capable of supplying a reagent to a substrate W mounted on the stage, a washing portion capable of supplying a washing solution to the substrate, an electric field stirring portion capable of stirring the reagent or the washing solution supplied to the substrate by applying an electric field to the reagent or the washing solution, and a control unit, wherein the washing portion, the reagent supply portion, and the electric field stirring portion are sequentially disposed in a Y direction as a first direction, and the device includes a stage transport mechanism that moves the stage in the Y direction, and a stage tilting mechanism that tilts the stage in an X direction as a second direction crossing the Y direction when the stage is positioned in the washing portion.

18 Claims, 44 Drawing Sheets

(51) Int. Cl.
  *G02B 21/34* (2006.01)
  *G01N 1/31* (2006.01)
  *G01N 1/34* (2006.01)
  *G01N 33/483* (2006.01)
  *G01N 35/00* (2006.01)
  *G01N 1/00* (2006.01)

(52) U.S. Cl.
  CPC ..... *G01N 33/483* (2013.01); *G01N 35/00029* (2013.01); *G02B 21/34* (2013.01); *G01N 2001/002* (2013.01); *G01N 2001/386* (2013.01); *G01N 2035/00039* (2013.01)

(56) References Cited

U.S. PATENT DOCUMENTS

| | | |
|---|---|---|
| 5,575,978 A | 11/1996 | Clark et al. |
| 5,610,069 A | 3/1997 | Clark et al. |
| 5,627,522 A | 5/1997 | Walker et al. |
| 5,635,364 A | 6/1997 | Clark et al. |
| 2005/0153453 A1 | 7/2005 | Copeland et al. |
| 2006/0120921 A1 | 6/2006 | Elliot et al. |
| 2006/0153736 A1* | 7/2006 | Kalra ............... G01N 33/5302 422/400 |
| 2013/0078624 A1* | 3/2013 | Holmes ............... C12Q 1/00 73/61.52 |
| 2015/0233902 A1* | 8/2015 | Akagami ............... G01N 1/28 435/7.1 |

FOREIGN PATENT DOCUMENTS

| | | |
|---|---|---|
| JP | 2001-296219 A | 10/2001 |
| JP | 2004-276460 A | 10/2004 |
| JP | 2005-530165 A | 10/2005 |
| JP | 2007-528485 A | 10/2007 |
| JP | 2015-155811 A | 8/2015 |
| JP | 2015-204811 A | 11/2015 |
| JP | 2016-109636 A | 6/2016 |
| WO | WO-93-20440 A1 | 10/1993 |
| WO | WO-2004-001390 A1 | 12/2003 |
| WO | WO-2005-024385 A2 | 3/2005 |

* cited by examiner

[Fig. 1]
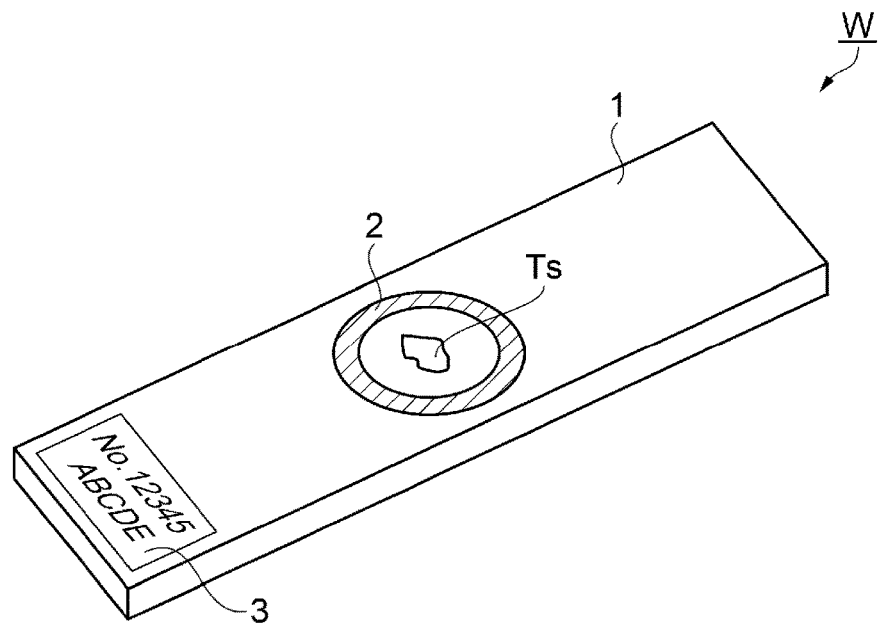
[Fig. 2]
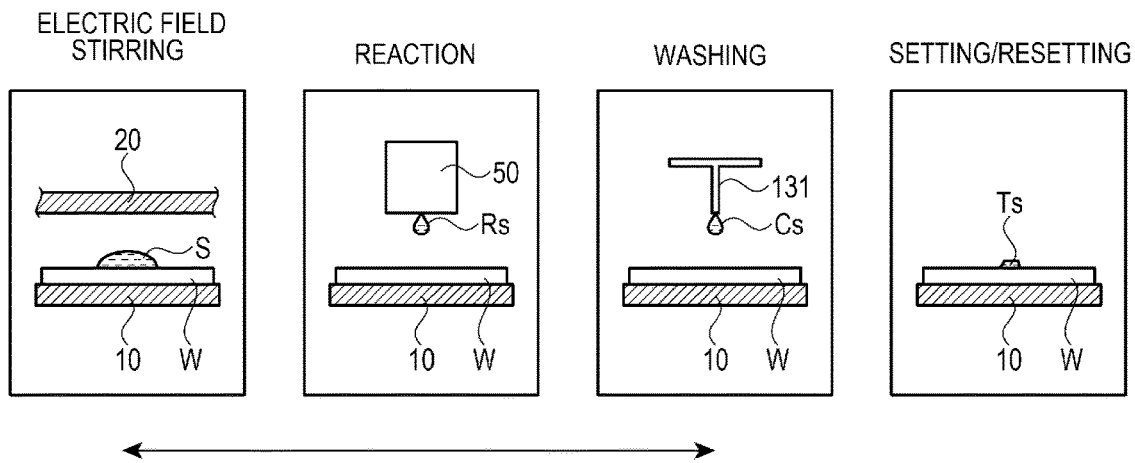

[Fig. 3]
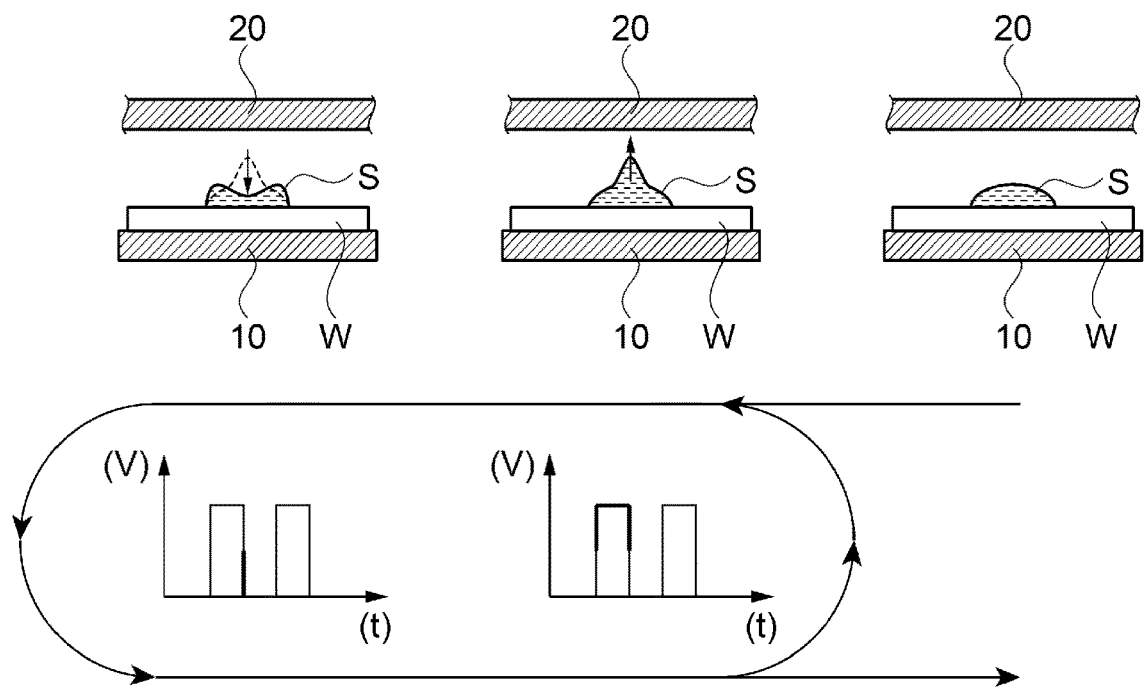

[Fig. 4]
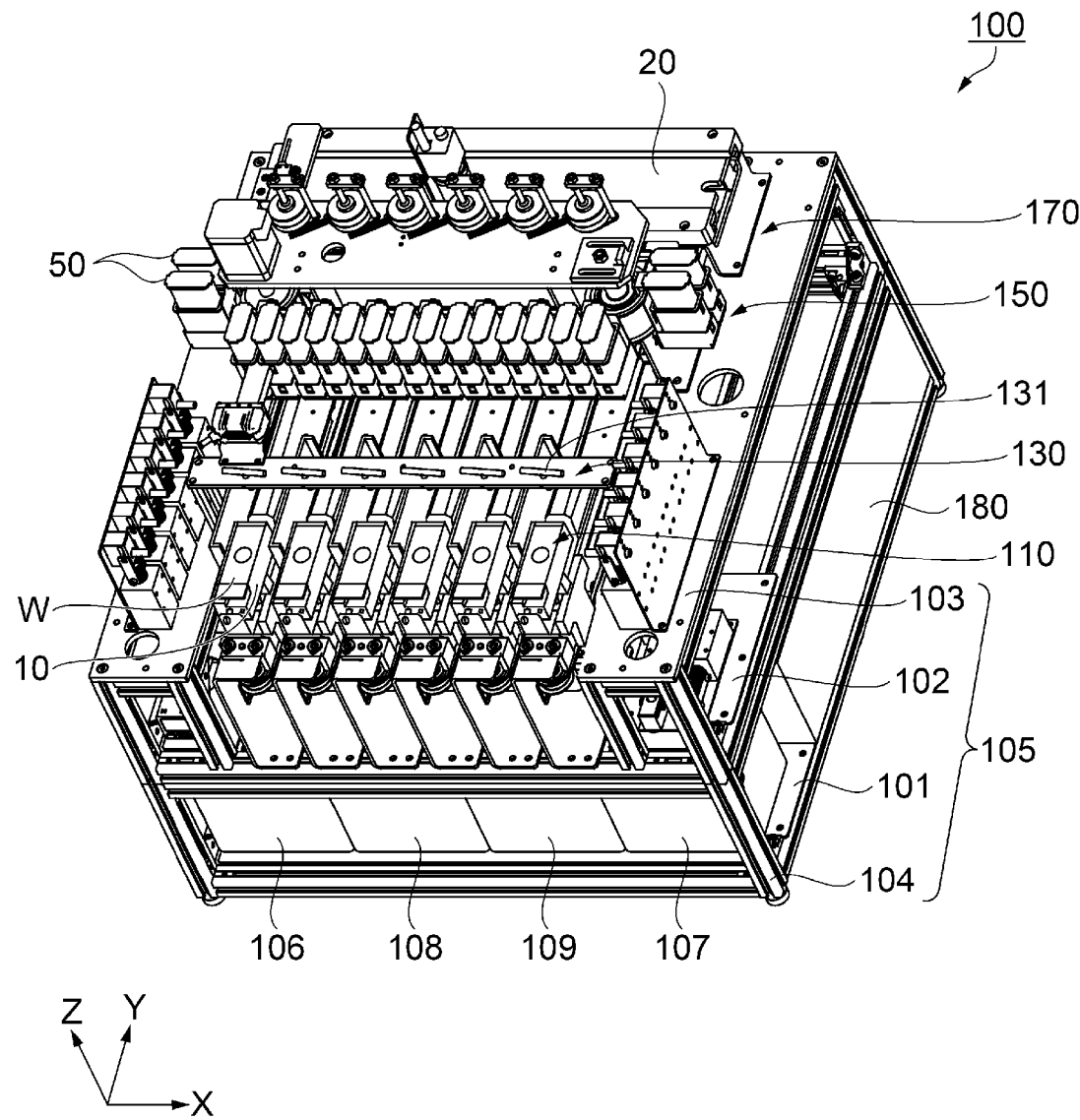

[Fig. 5]
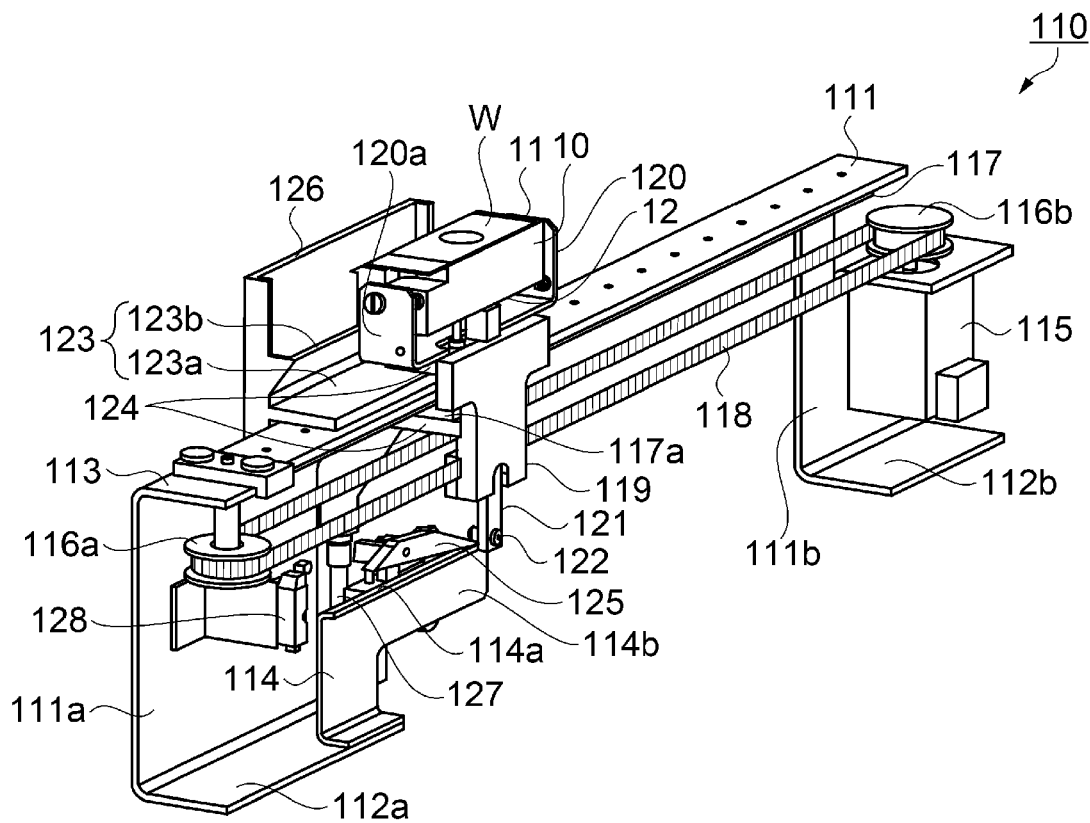

[Fig. 6]
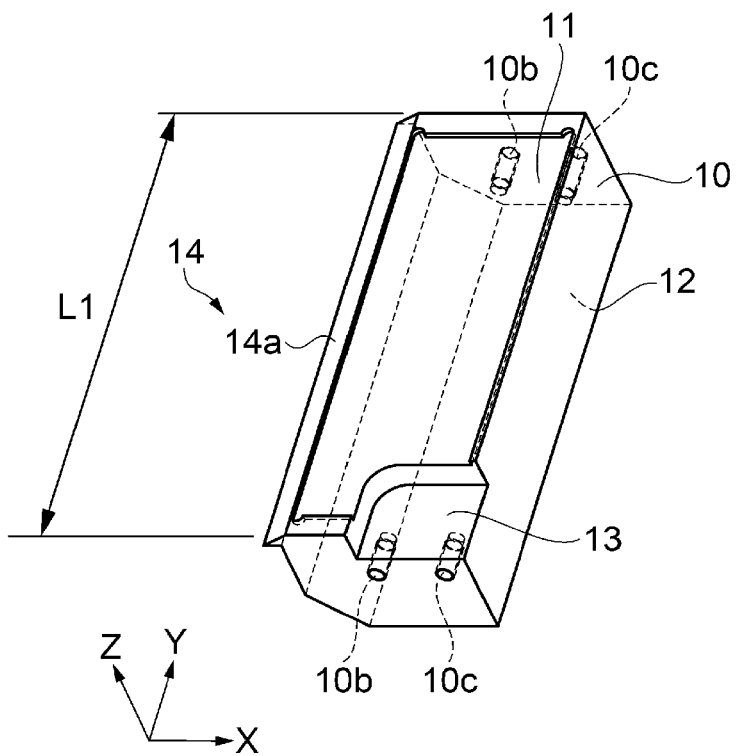
[Fig. 7]
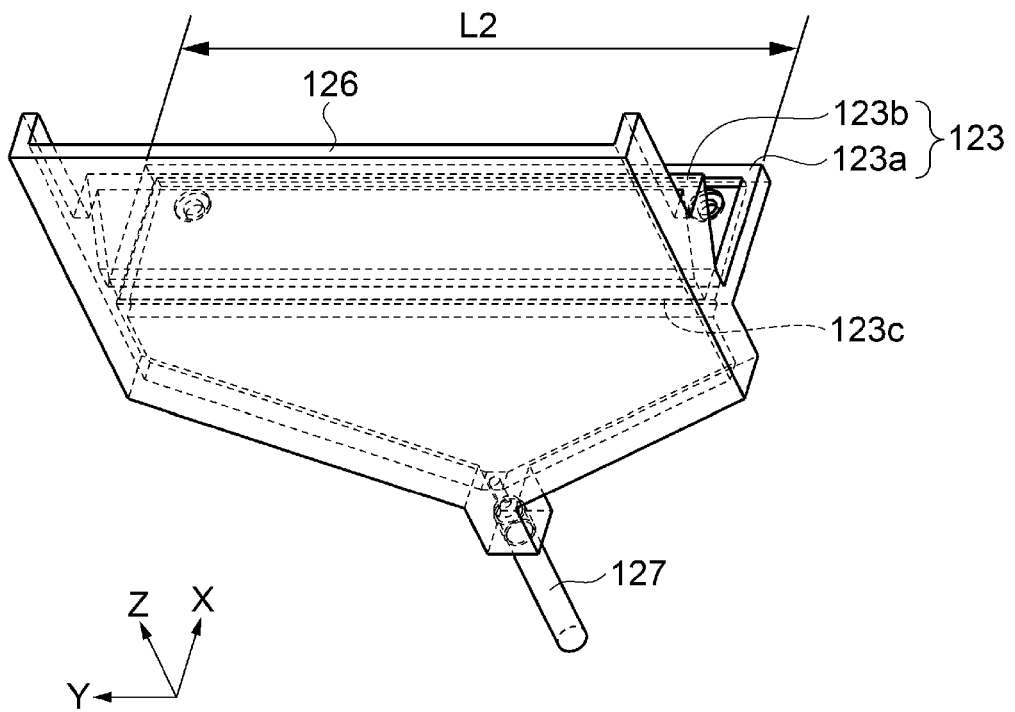

[Fig. 8]
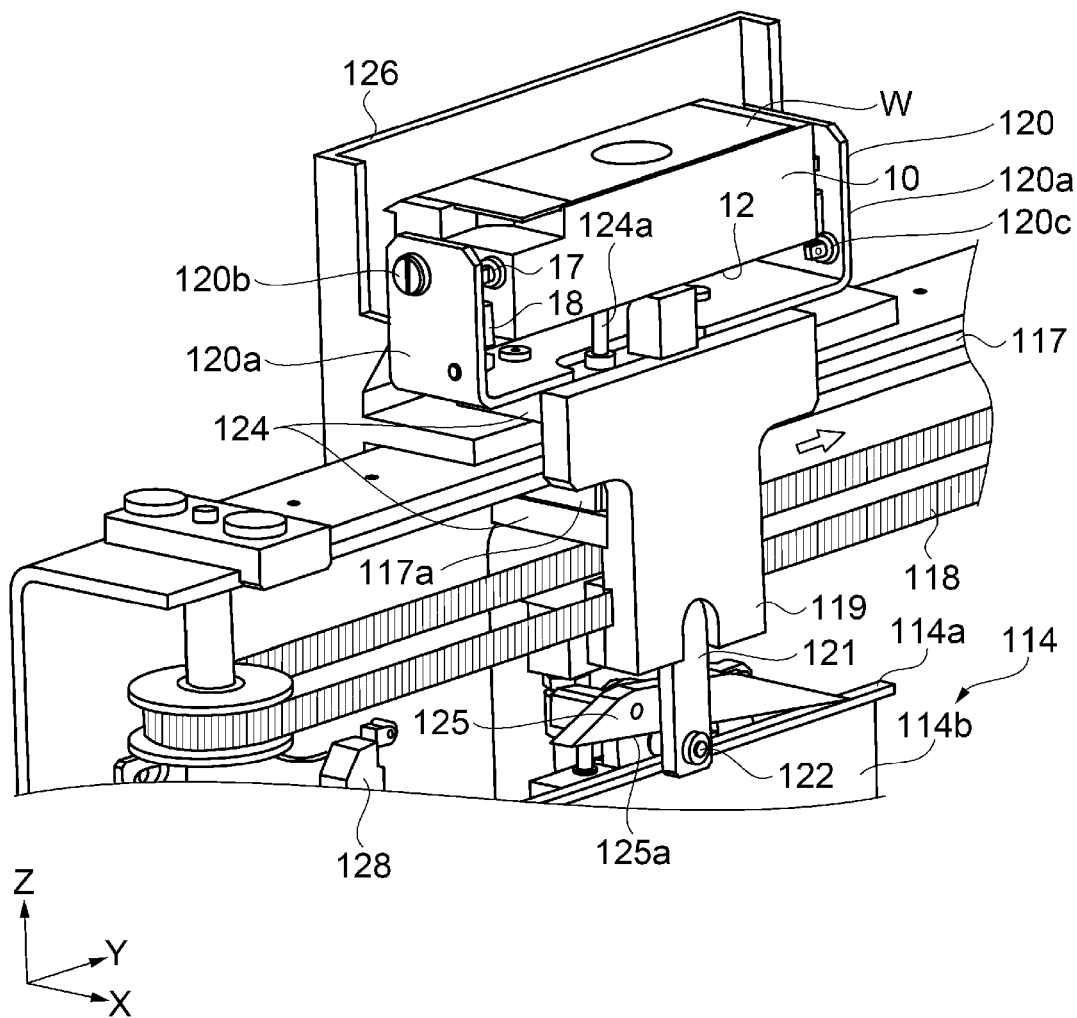

[Fig. 9]
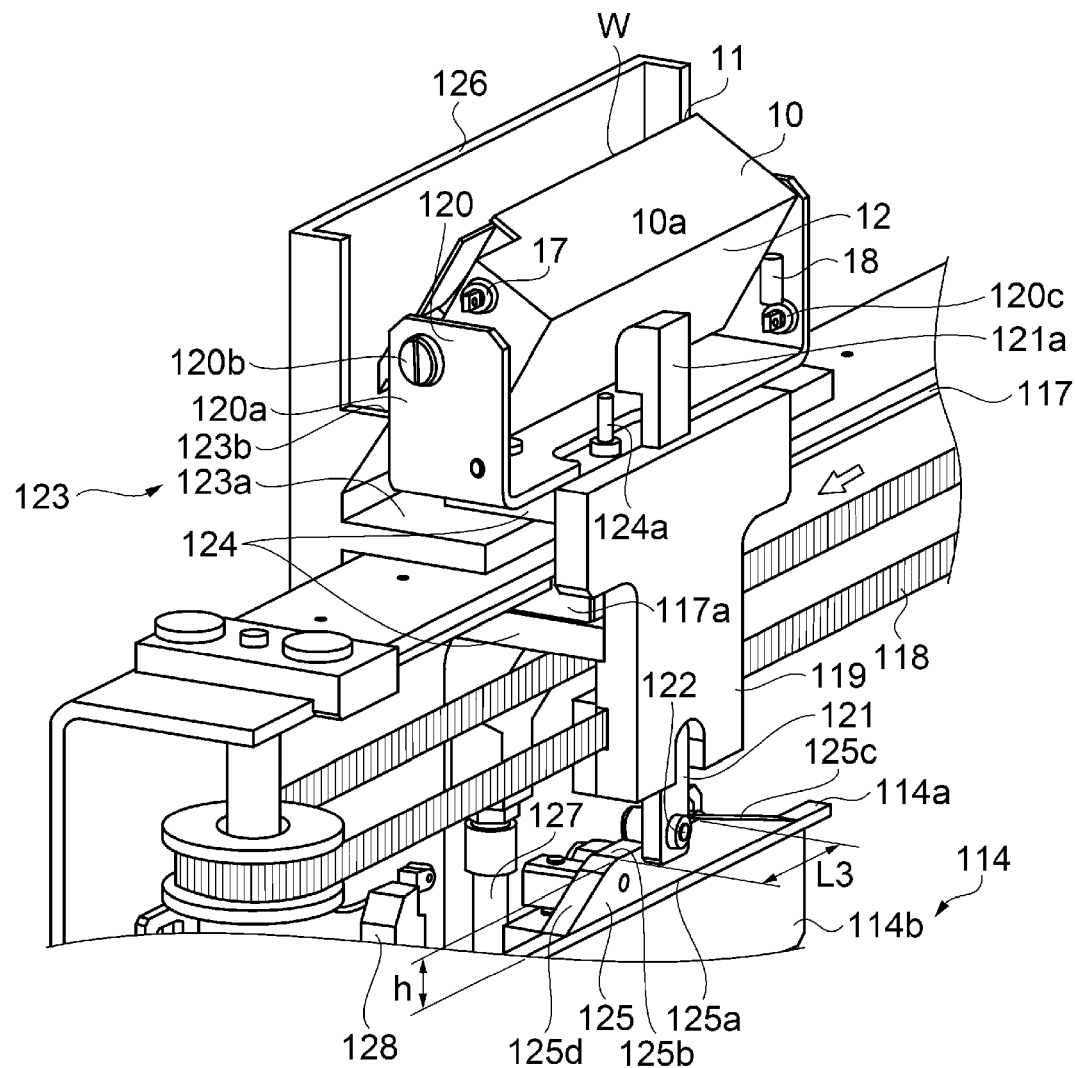

[Fig. 10]
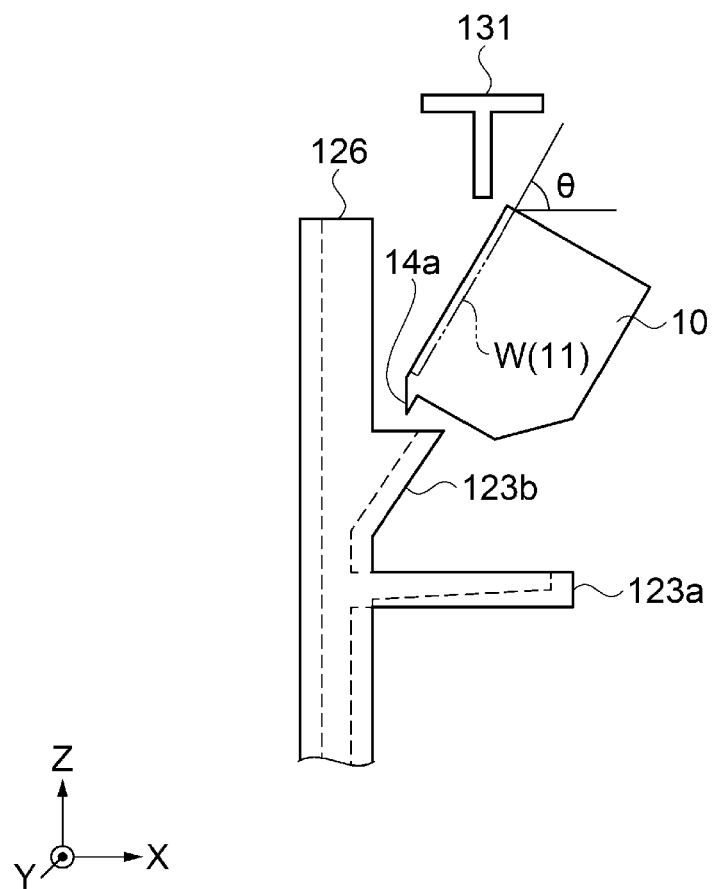

[Fig. 11]
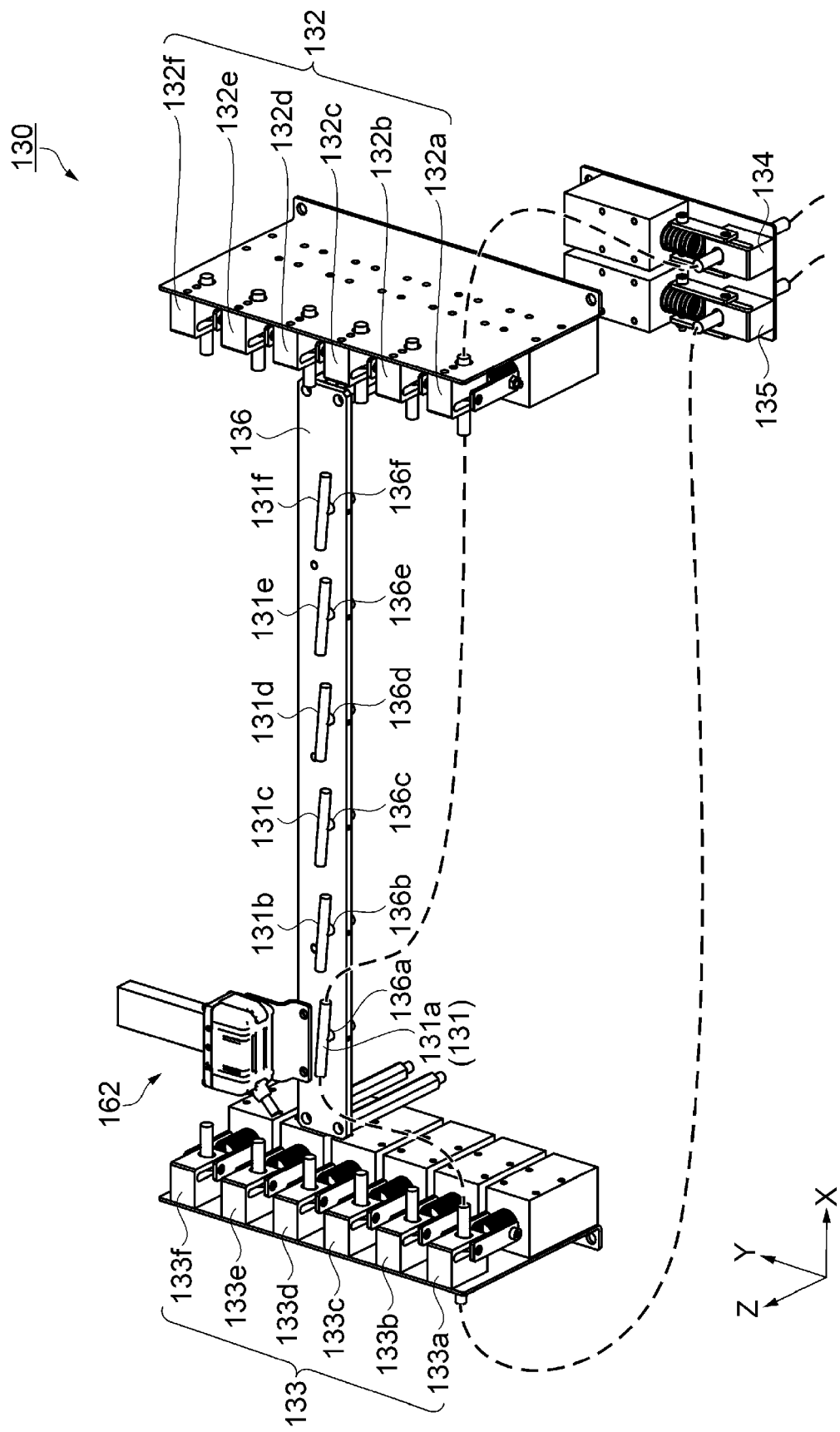

[Fig. 12]
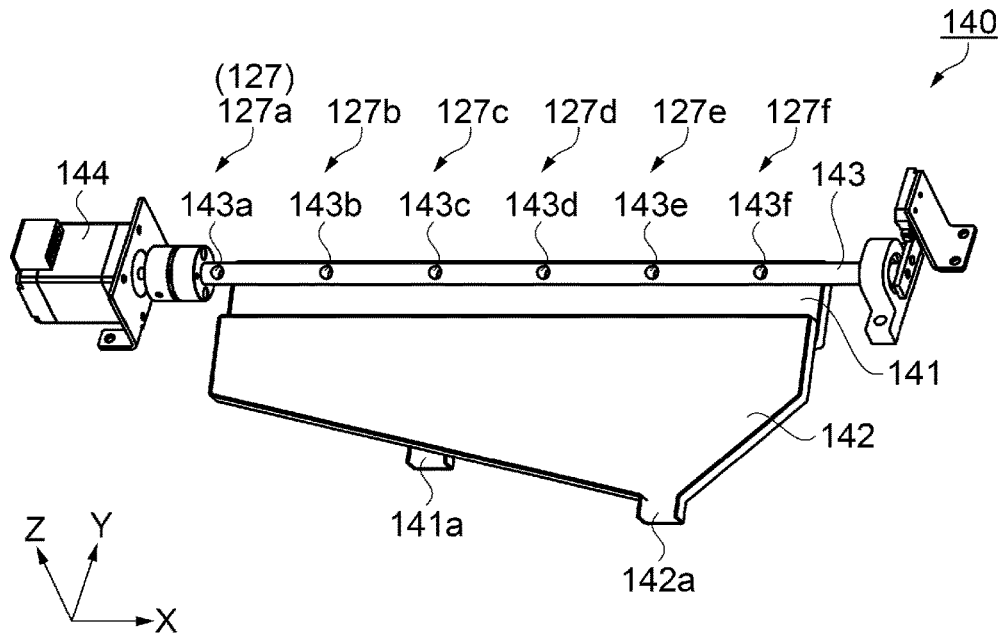
[Fig. 13]
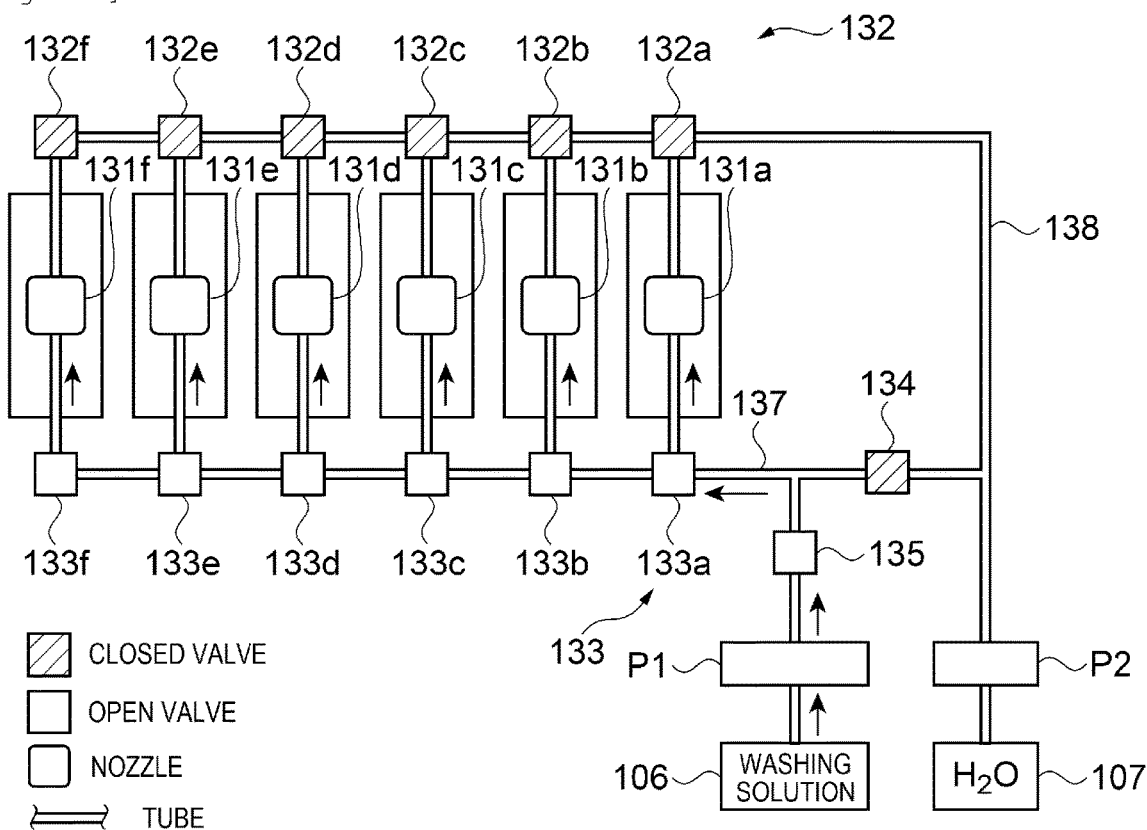

[Fig. 14]
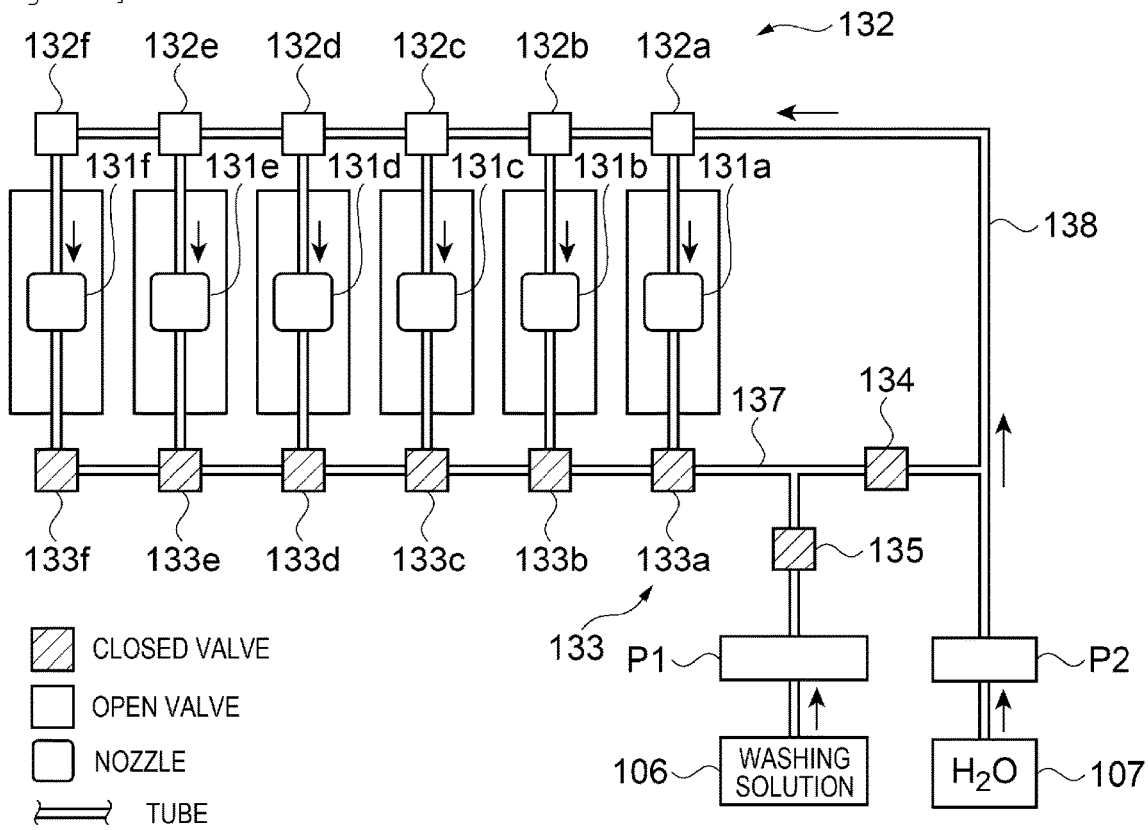
[Fig. 15]
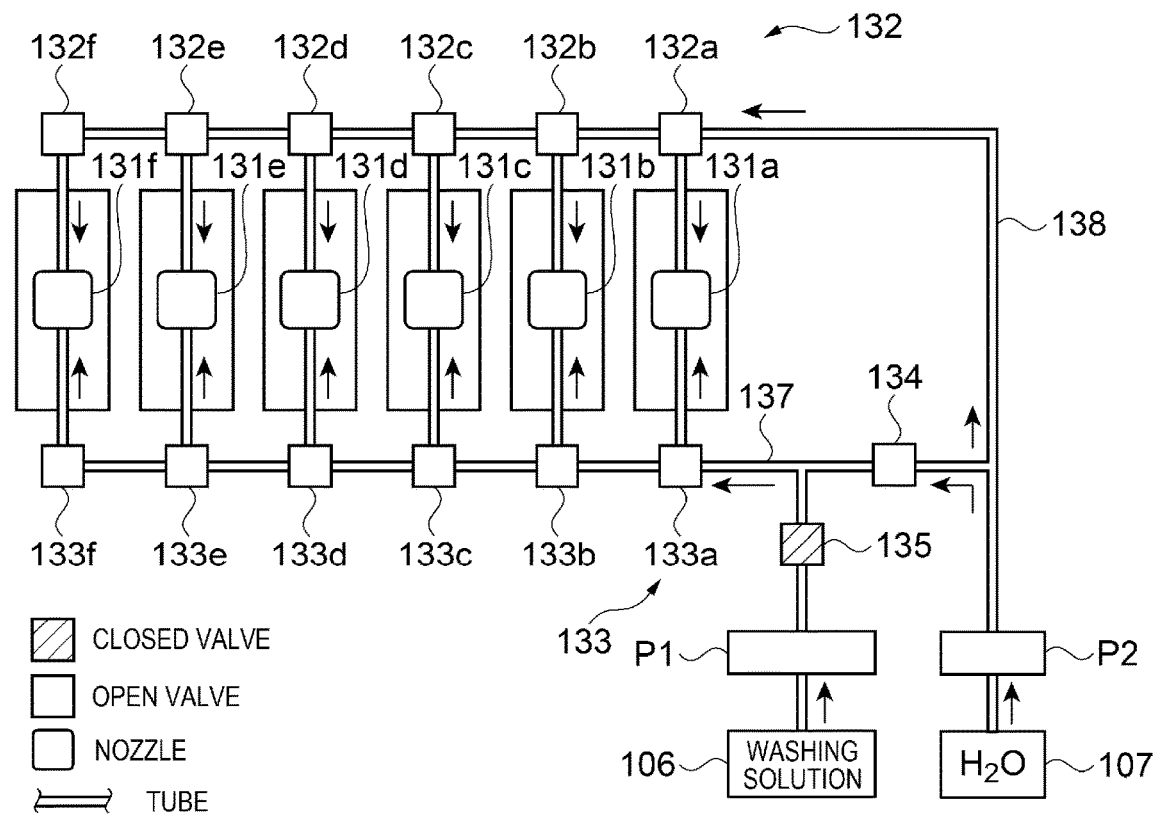

[Fig. 16]
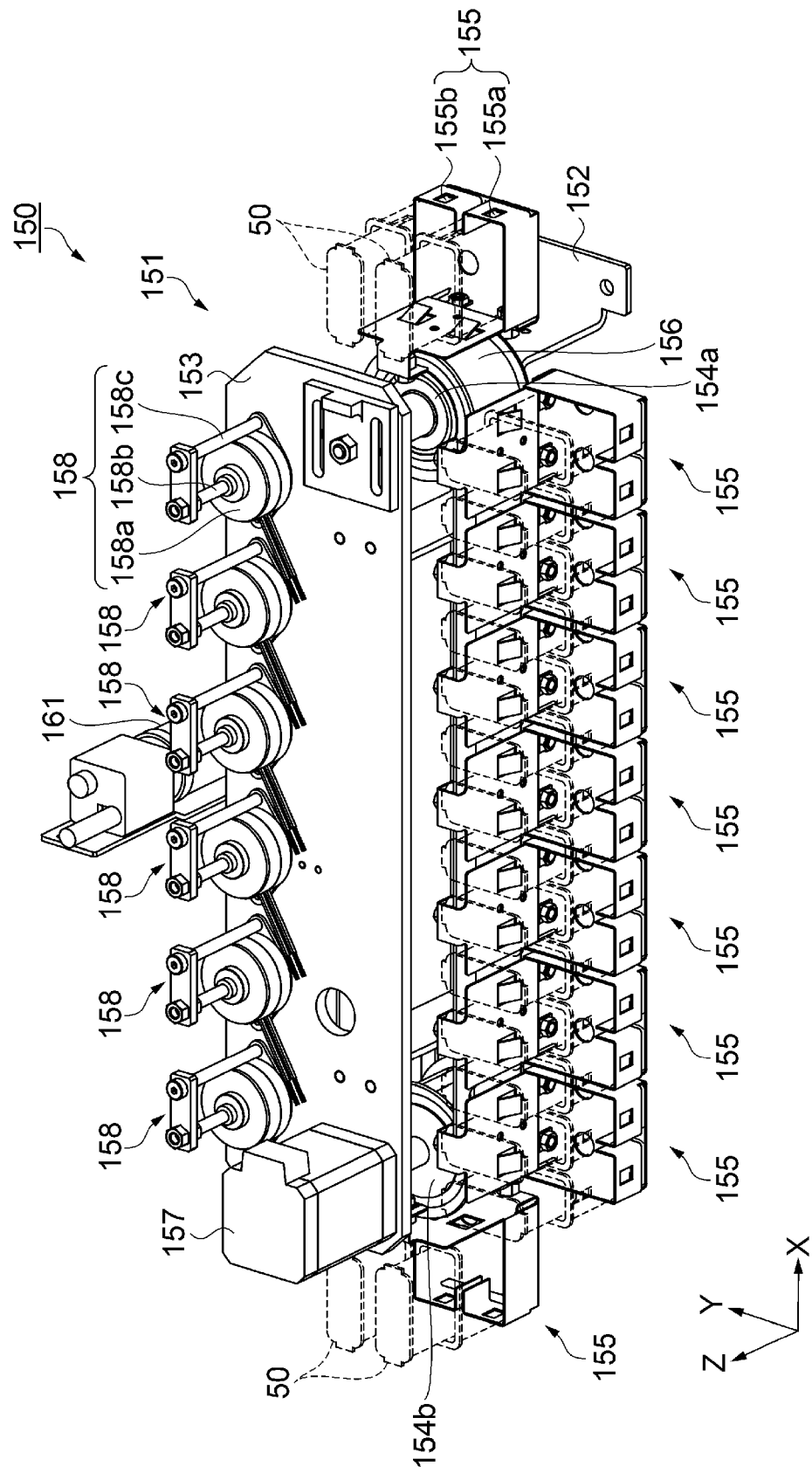

[Fig. 17]
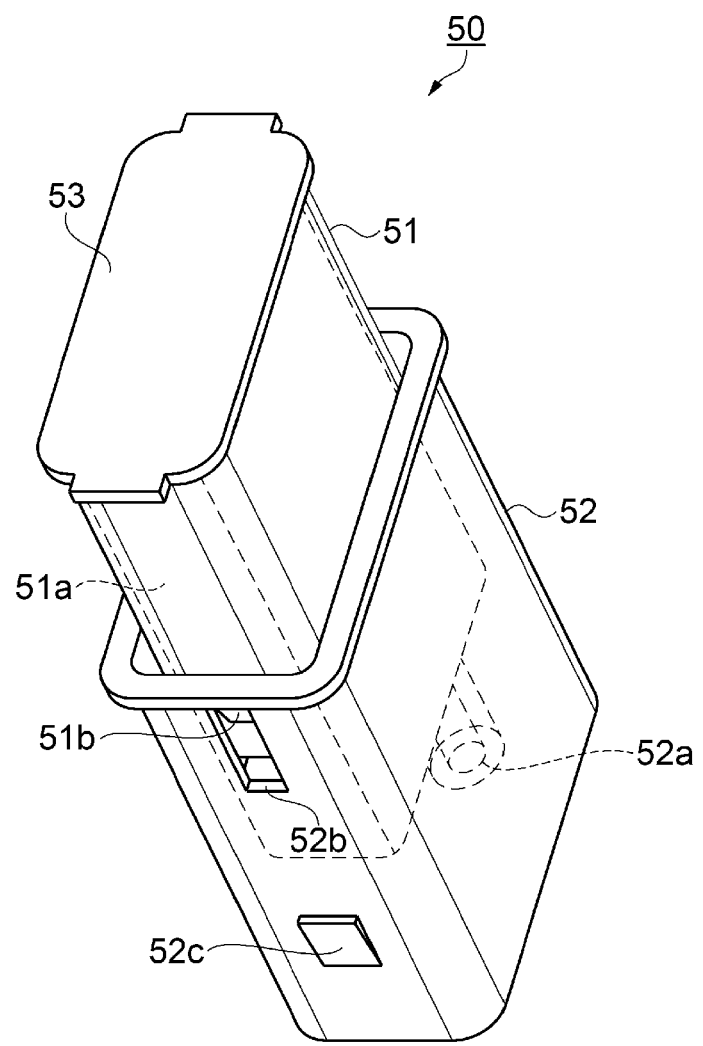

[Fig. 18]
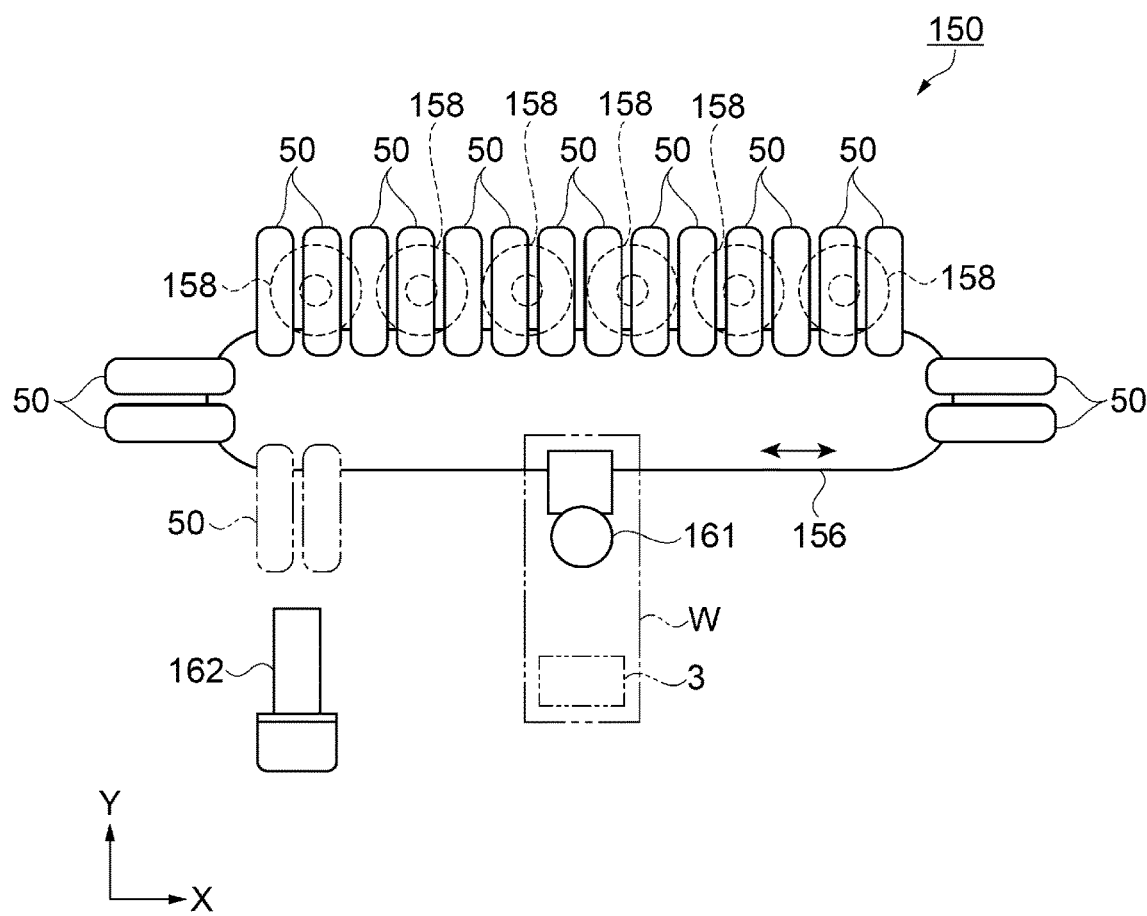

[Fig. 19]
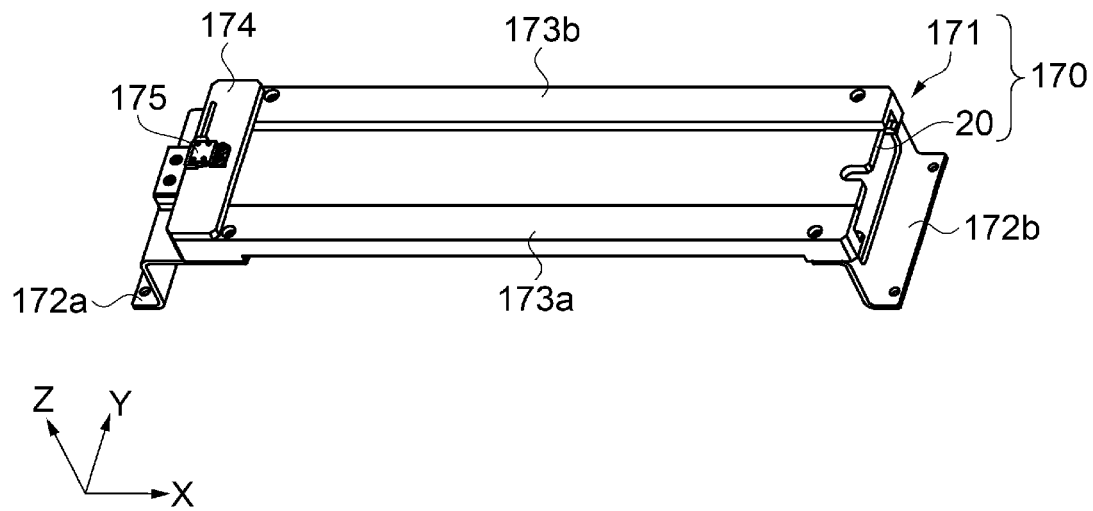
[Fig. 20]
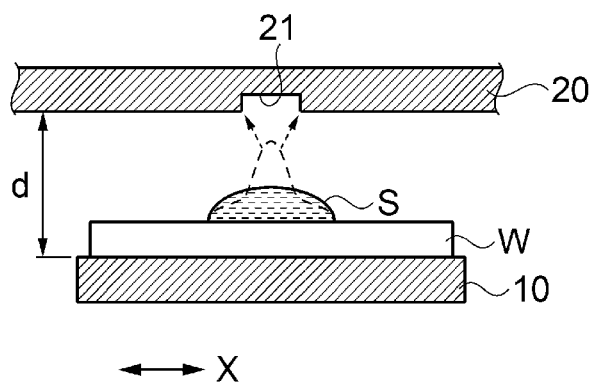

[Fig. 21]
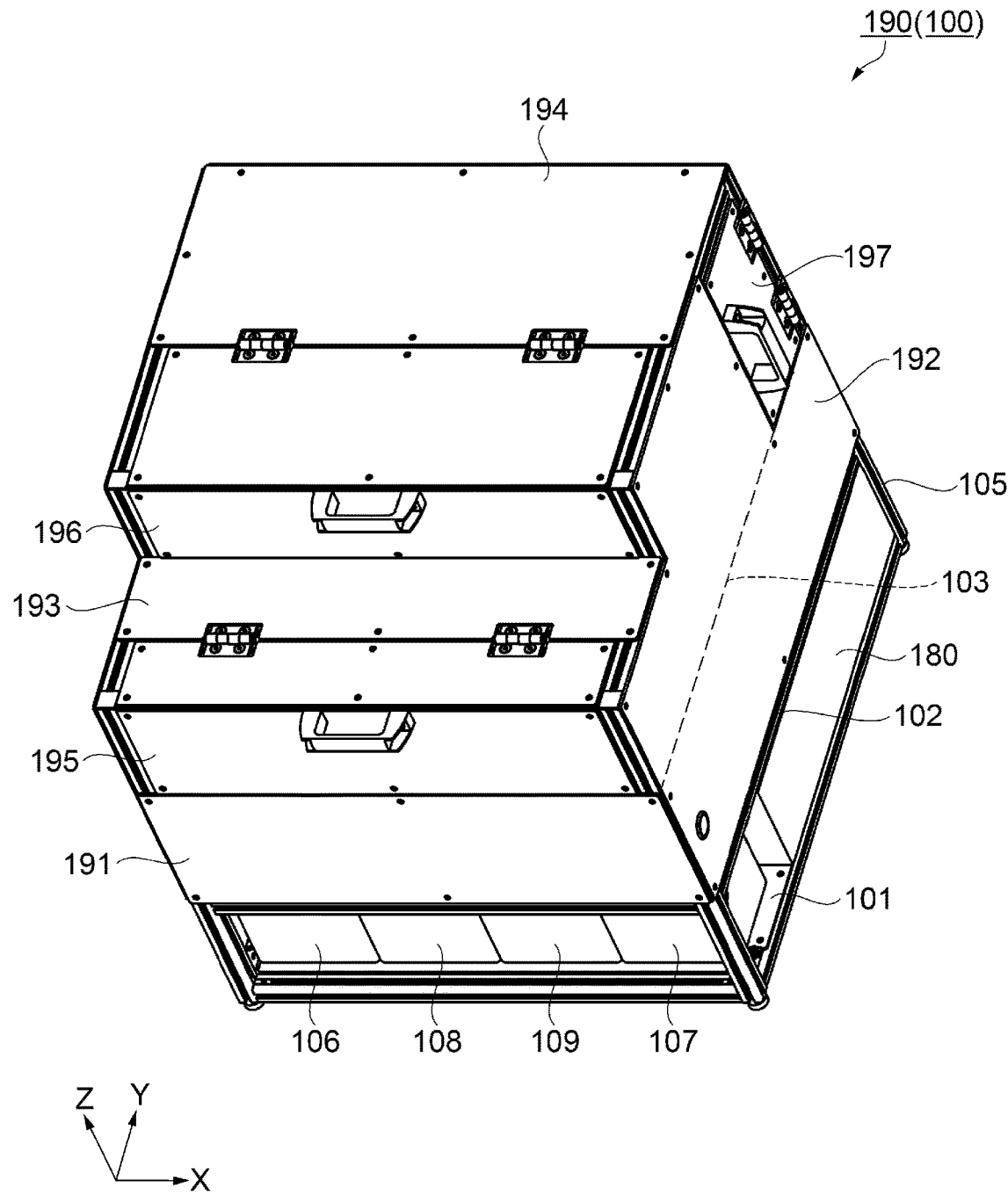

[Fig. 22]
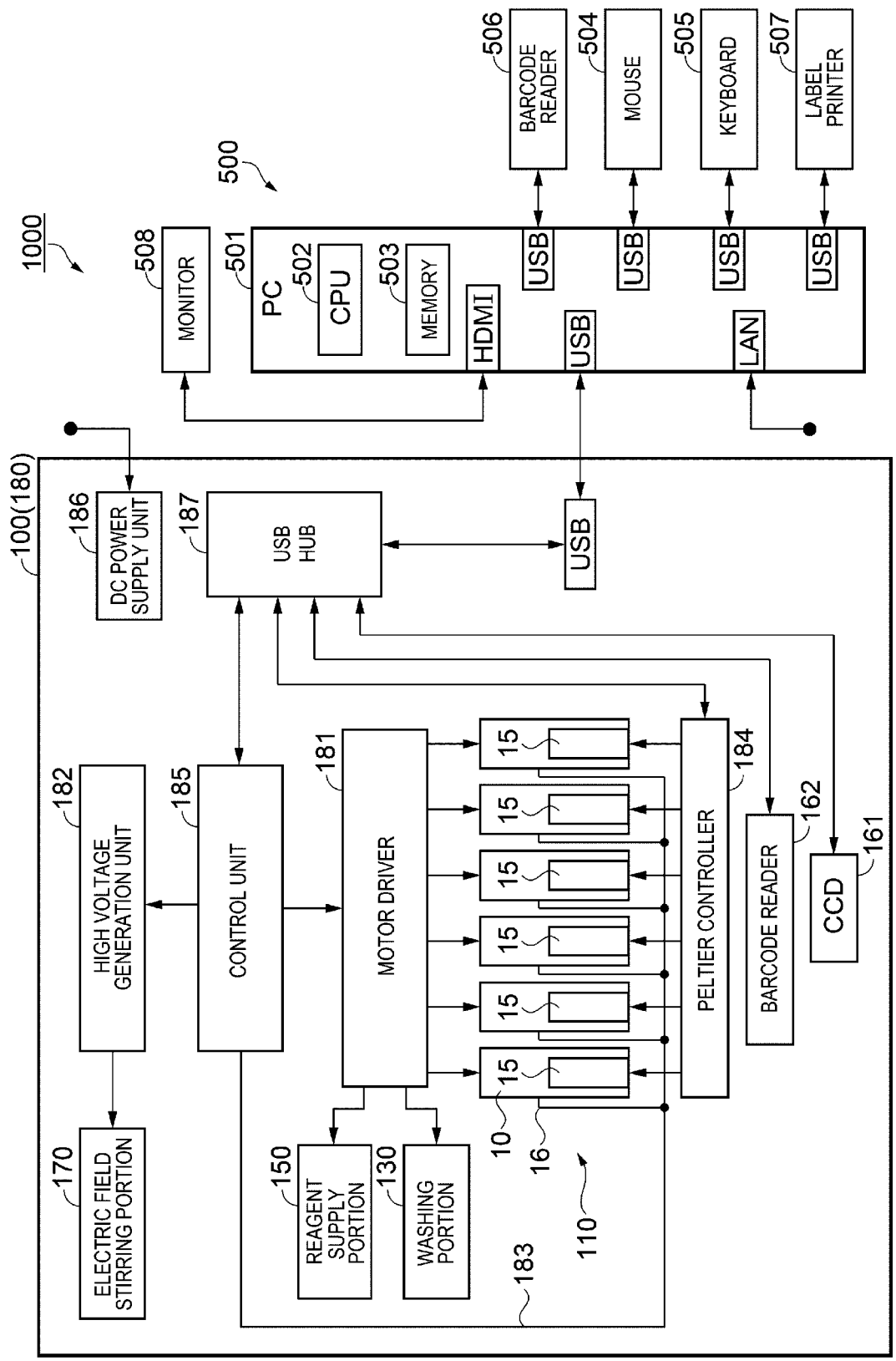

[Fig. 23]

(EXAMPLE 1)

| STEP NAME | USED REAGENT | OPERATION | TIME | |
|---|---|---|---|---|
| SLICING | PIG LIVER BLOCK | | | |
| FIXING | ACETONE | IMMERSION | 2 MIN | |
| WASHING | PBS-T | CONTINUOUS FLOW | 30 SEC | USING DEVICE |
| REMOVAL OF ENDOGENOUS PO | 3% AQUEOUS HYDROGEN PEROXIDE SOLUTION | LEAVING TO STAND IN 150 μL | 1 MIN | |
| WASHING | PBS-T | CONTINUOUS FLOW | 30 SEC | |
| PRIMARY ANTIBODY REACTION | PRIMARY ANTIBODY REAGENT | ELECTRIC FIELD STIRRING IN 150 μL | 5 MIN | |
| WASHING | PBS-T | CONTINUOUS FLOW | 30 SEC | |
| SECONDARY ANTIBODY REACTION | SECONDARY ANTIBODY REAGENT | ELECTRIC FIELD STIRRING IN 150 μL | 5 MIN | |
| WASHING | PBS-T | CONTINUOUS FLOW | 30 SEC | |
| COLOR DEVELOPMENT | DAB | LEAVING TO STAND IN 150 μL | 3 MIN | |
| WASHING | PURE WATER | CONTINUOUS FLOW | 2 MIN | |
| NUCLEAR STAINING | HEMATOXYLIN | LEAVING TO STAND IN 150 μL | 1 MIN | |
| WASHING | PURE WATER | CONTINUOUS FLOW | 2 MIN | |
| ENCAPSULATION | ENCAPSULATING AGENT | COVERING WITH COVER SLIP | 1 MIN | |
| ANALYSIS | — | IMAGE ANALYSIS, DIGITIZING DEPTH OF STAINING | 1 MIN | |
| | | TOTAL | ABOUT 25 MIN | |

[Fig. 24]

(COMPARATIVE EXAMPLE 1)

| STEP NAME | USED REAGENT | OPERATION | TIME |
|---|---|---|---|
| SLICING | PIG LIVER BLOCK | | |
| FIXING | ACETONE | IMMERSION | 2 MIN |
| WASHING | PBS-T | 3 TANKS | 30 SEC |
| REMOVAL OF ENDOGENOUS PO | 3% AQUEOUS HYDROGEN PEROXIDE SOLUTION | IMMERSION | 1 MIN |
| WASHING | PBS-T | 3 TANKS | 30 SEC |
| PRIMARY ANTIBODY REACTION | PRIMARY ANTIBODY REAGENT | LEAVING TO STAND IN 150 μL | 30 MIN |
| WASHING | PBS-T | 3 TANKS | 30 SEC |
| SECONDARY ANTIBODY REACTION | SECONDARY ANTIBODY REAGENT | LEAVING TO STAND IN 150 μL | 30 MIN |
| WASHING | PBS-T | 3 TANKS | 30 SEC |
| COLOR DEVELOPMENT | DAB | LEAVING TO STAND IN 150 μL | 3 MIN |
| WASHING | PURE WATER | RUNNING WATER | 2 MIN |
| NUCLEAR STAINING | HEMATOXYLIN | LEAVING TO STAND IN 150 μL | 1 MIN |
| WASHING | PURE WATER | RUNNING WATER | 2 MIN |
| ENCAPSULATION | ENCAPSULATING AGENT | COVERING WITH COVER SLIP | 1 MIN |
| ANALYSIS | — | IMAGE ANALYSIS, DIGITIZING DEPTH OF STAINING | 1 MIN |
| | | TOTAL | ABOUT 75 MIN |

[Fig. 25]

(IMMERSION 2)

| STEP NAME | USED REAGENT | OPERATION | TIME | |
|---|---|---|---|---|
| SLICING | PIG LIVER BLOCK | | | |
| DEPARAFFINIZATION | DEPARAFFINIZATION SOLUTION | EAVING TO STAND IN 200 μL×3(75°C) | 3 MIN | |
| WASTE LIQUID | — | DEPARAFFINIZATION AND REMOVAL ×3 | | |
| WASHING | PBS-T | CONTINUOUS FLOW | 30 SEC | |
| ANTIGEN ACTIVATION | ACTIVATION SOLUTION | ELECTRIC FIELD STIRRING IN 200 μL (95°C) | 40 MIN | |
| DROPPING OIL | OIL | ELECTRIC FIELD STIRRING IN 200 μL (95°C) | | |
| NATURAL COOLING | — | — | 20 MIN | |
| WASHING | PBS-T | CONTINUOUS FLOW | 30 SEC | USING DEVICE |
| REMOVAL OF ENDOGENOUS PO | 3% AQUEOUS HYDROGEN PEROXIDE SOLUTION | LEAVING TO STAND IN 200 μL | 1 MIN | |
| WASHING | PBS-T | CONTINUOUS FLOW | 30 SEC | |
| PRIMARY ANTIBODY REACTION | PRIMARY ANTIBODY REAGENT | ELECTRIC FIELD STIRRING IN 200 μL | 10 MIN | |
| WASHING | PBS-T | CONTINUOUS FLOW | 30 SEC | |
| SECONDARY ANTIBODY REACTION | SECONDARY ANTIBODY REAGENT | ELECTRIC FIELD STIRRING IN 200 μL | 7 MIN | |
| WASHING | PBS-T | CONTINUOUS FLOW | 30 SEC | |
| COLOR DEVELOPMENT | DAB | LEAVING TO STAND IN 200 μL | 3 MIN | |
| WASHING | PURE WATER | CONTINUOUS FLOW | 2 MIN | |
| NUCLEAR STAINING | HEMATOXYLIN | LEAVING TO STAND IN 200 μL | 1 MIN | |
| WASHING | PURE WATER | CONTINUOUS FLOW | 2 MIN | |
| CLEARING | HEMATOXYLIN, XYLENE | 10 TANKS | 100 SEC | |
| ENCAPSULATION | ENCAPSULATING AGENT | COVERING WITH COVER SLIP | 1 MIN | |
| ANALYSIS | — | IMAGE ANALYSIS, DIGITIZING DEPTH OF STAINING | 1 MIN | |
| | | TOTAL | ABOUT 96 MIN | |

[Fig. 26]

(COMPARATIVE EXAMPLE 2)

| STEP NAME | USED REAGENT | OPERATION | TIME |
|---|---|---|---|
| SLICING | PIG LIVER BLOCK | | |
| DEPARAFFINIZATION | XYLENE | 3 TANKS | 9 MIN |
| | HEMATOXYLIN | 5 TANKS | 5 MIN |
| WASHING | PBS-T | 3 TANKS | 30 SEC |
| ANTIGEN ACTIVATION | ACTIVATION SOLUTION | 1 TANK (95°C) | 40 MIN |
| — | — | — | — |
| NATURAL COOLING | — | — | 20 MIN |
| WASHING | PBS-T | 3 TANKS | 30 SEC |
| REMOVAL OF ENDOGENOUS PO | 3% AQUEOUS HYDROGEN PEROXIDE SOLUTION | IMMERSION | 5 MIN |
| WASHING | PBS-T | 3 TANKS | 30 SEC |
| PRIMARY ANTIBODY REACTION | PRIMARY ANTIBODY REACTION | LEAVING TO STAND IN 200 μL | 30 MIN |
| WASHING | PBS-T | 3 TANKS | 30 SEC |
| SECONDARY ANTIBODY REACTION | SECONDARY ANTIBODY REAGENT | LEAVING TO STAND IN 200 μL | 30 MIN |
| WASHING | PBS-T | 3 TANKS | 30 SEC |
| COLOR DEVELOPMENT | DAB | LEAVING TO STAND IN 200 μL | 3 MIN |
| WASHING | PURE WATER | RUNNING WATER | 2 MIN |
| NUCLEAR STAINING | HEMATOXYLIN | LEAVING TO STAND IN 200 μL | 1 MIN |
| WASHING | PURE WATER | RUNNING WATER | 2 MIN |
| CLEARING | HEMATOXYLIN, XYLENE | 10 TANKS | 100 SEC |
| ENCAPSULATION | ENCAPSULATING AGENT | COVERING WITH COVER SLIP | 1 MIN |
| ANALYSIS | — | IMAGE ANALYSIS, DIGITIZING DEPTH OF STAINING | 1 MIN |
| | | TOTAL | ABOUT 154 MIN |

[Fig. 27]

(EXAMPLE 3)

| STEP NAME | USED REAGENT | OPERATION | TIME |
|---|---|---|---|
| SLICING | PIG LIVER BLOCK | | |
| DEPARAFFINIZATION | XYLENE | 3'×3 TANKS | 9 MIN |
| | ETHANOL | 1'×5 TANKS | 5 MIN |
| WASHING | PBS-T | 3 TANKS | 30 SEC |
| REMOVAL OF ENDOGENOUS PO | 3% AQUEOUS HYDROGEN PEROXIDE SOLUTION | IMMERSION | 1 MIN |
| WASHING | PBS-T | 3 TANKS | 30 SEC |
| THERMAL DENATURATION | PROBE | 10 μL | 10 MIN |
| | DROPPING OIL | HEATING TO 95°C IN 40 μL | |
| | — | NATURAL COOLING | 20 MIN |
| HYBRIDIZATION | PROBE+OIL | ELECTRIC FIELD STIRRING AT 37°C IN 50 μL | 180 MIN |
| WASHING | PBS-T | CONTINUOUS FLOW | 30 SEC |
| PRIMARY ANTIBODY REACTION | PRIMARY ANTIBODY REAGENT | 30 μL | 1 MIN |
| | DROPPING OIL | 30 μL | 1 MIN |
| | — | ELECTRIC FIELD STIRRING IN 60 μL | 5 MIN |
| WASHING | PBS-T | CONTINUOUS FLOW | 30 SEC |
| SECONDARY ANTIBODY REACTION | SECONDARY ANTIBODY REAGENT | 30 μL | 1 MIN |
| | DROPPING OIL | 30 μL | 1 MIN |
| | — | ELECTRIC FIELD STIRRING IN 60 μL | 5 MIN |
| WASHING | PBS-T | CONTINUOUS FLOW | 30 SEC |
| COLOR DEVELOPMENT | DAB | ELECTRIC FIELD STIRRING IN 60 μL | 3 MIN |
| WASHING | PURE WATER | CONTINUOUS FLOW | 2 MIN |
| NUCLEAR STAINING | HEMATOXYLIN | ELECTRIC FIELD STIRRING IN 100 μL | 1 MIN |
| WASHING | PURE WATER | CONTINUOUS FLOW | 2 MIN |
| CLEARING | HEMATOXYLIN, XYLENE | 10 TANKS | 100 SEC |
| ENCAPSULATION | ENCAPSULATING AGENT | COVERING WITH COVER SLIP | 1 MIN |
| ANALYSIS | — | IMAGE ANALYSIS, DIGITIZING DEPTH OF STAINING | 1 MIN |
| TOTAL | | | ABOUT 254 MIN |

(USING DEVICE: from THERMAL DENATURATION through WASHING after NUCLEAR STAINING)

[Fig. 28]

(COMPARATIVE EXAMPLE 3)

| STEP NAME | USED REAGENT | OPERATION | TIME |
|---|---|---|---|
| SLICING | PIG LIVER BLOCK | | |
| DEPARAFFINIZATION | XYLENE | 3'×3 TANKS | 9 MIN |
| | ETHANOL | 1'×5 TANKS | 5 MIN |
| WASHING | PBS-T | 3 TANKS | 30 SEC |
| REMOVAL OF ENDOGENOUS PO | 3% AQUEOUS HYDROGEN PEROXIDE SOLUTION | IMMERSION | 1 MIN |
| WASHING | PBS-T | 3 TANKS | 30 SEC |
| THERMAL DENATURATION | PROBE | 10μL | 10 MIN |
| | DROPPING OIL | HEATING TO 95°C IN 40 μL | |
| | — | NATURAL COOLING | 20 MIN |
| HYBRIDIZATION | PROBE+OIL | ELECTRIC FIELD STIRRING AT 37°C IN 50 μL | 720 MIN |
| WASHING | PBS-T | CONTINUOUS FLOW | 30 SEC |
| PRIMARY ANTIBODY REACTION | PRIMARY ANTIBODY REAGENT | 30μL | 1 MIN |
| | DROPPING OIL | 30μL | 1 MIN |
| | | ELECTRIC FIELD STIRRING IN 60 μL | 20 MIN |
| WASHING | PBS-T | CONTINUOUS FLOW | 30 SEC |
| SECONDARY ANTIBODY REACTION | SECONDARY ANTIBODY REAGENT | 30μL | 1 MIN |
| | DROPPING OIL | 30μL | 1 MIN |
| | — | ELECTRIC FIELD STIRRING IN 60 μL | 20 MIN |
| WASHING | PBS-T | CONTINUOUS FLOW | 30 SEC |
| COLOR DEVELOPMENT | DAB | ELECTRIC FIELD STIRRING IN 60 μL | 3 MIN |
| WASHING | PURE WATER | CONTINUOUS FLOW | 2 MIN |
| NUCLEAR STAINING | HEMATOXYLIN | ELECTRIC FIELD STIRRING IN 100 μL | 1 MIN |
| WASHING | PURE WATER | CONTINUOUS FLOW | 2 MIN |
| CLEARING | HEMATOXYLIN, XYLENE | 10 TANKS | 100 SEC |
| ENCAPSULATION | ENCAPSULATING AGENT | COVERING WITH COVER SLIP | 1 MIN |
| ANALYSIS | — | IMAGE ANALYSIS, DIGITIZING DEPTH OF STAINING | 1 MIN |
| | | TOTAL | ABOUT 824 MIN |

[Fig. 29]
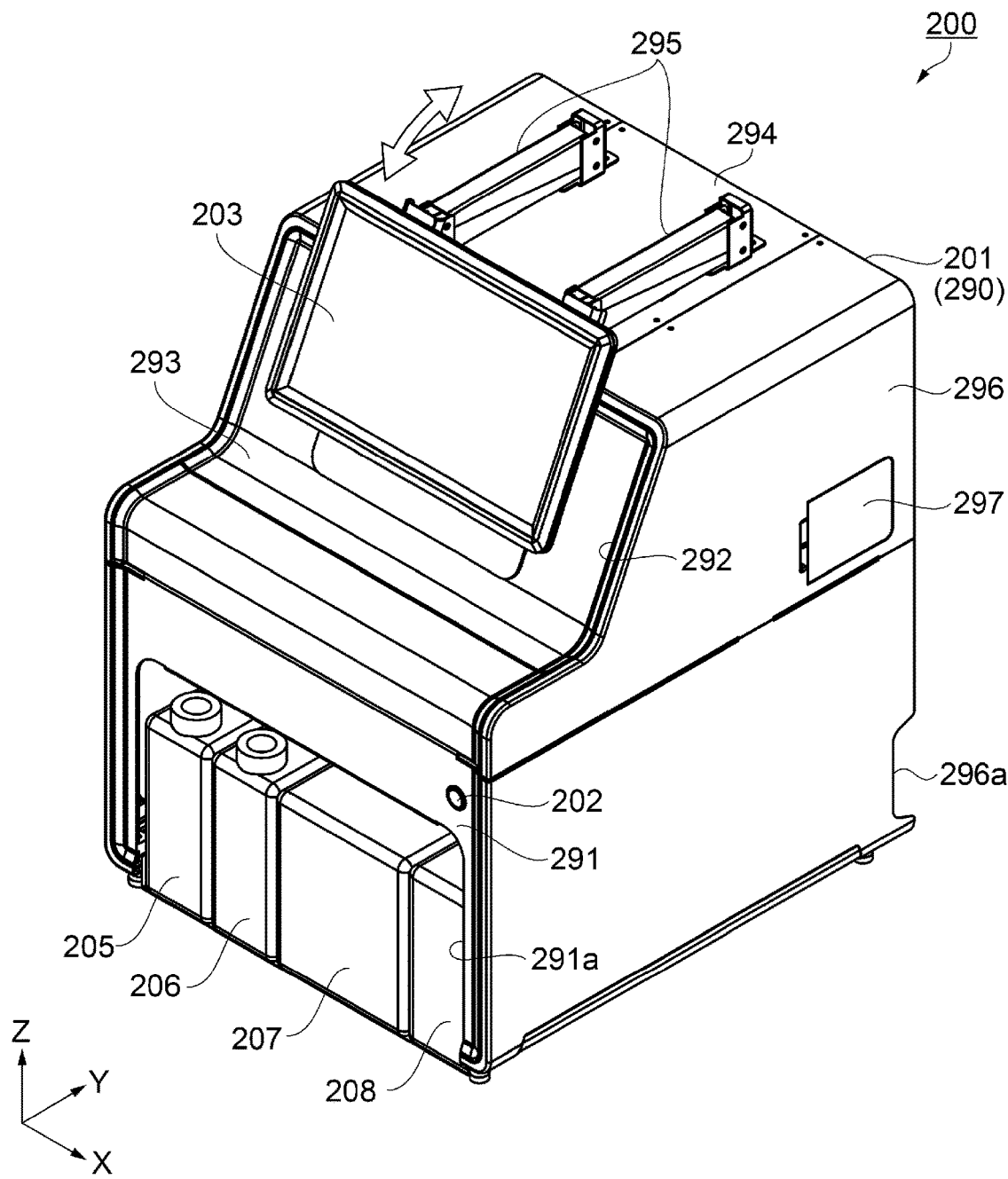

[Fig. 30]
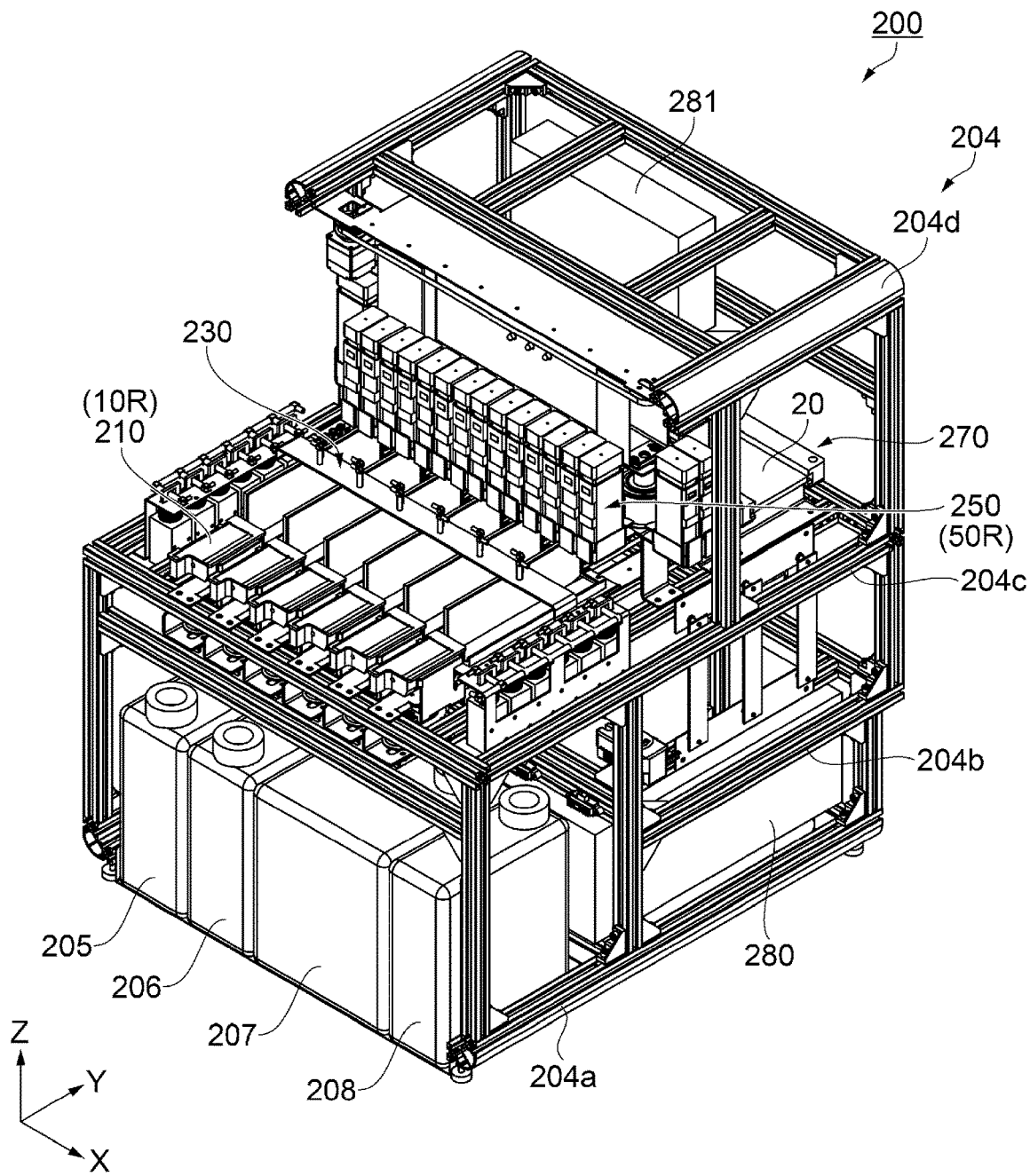

[Fig. 31]
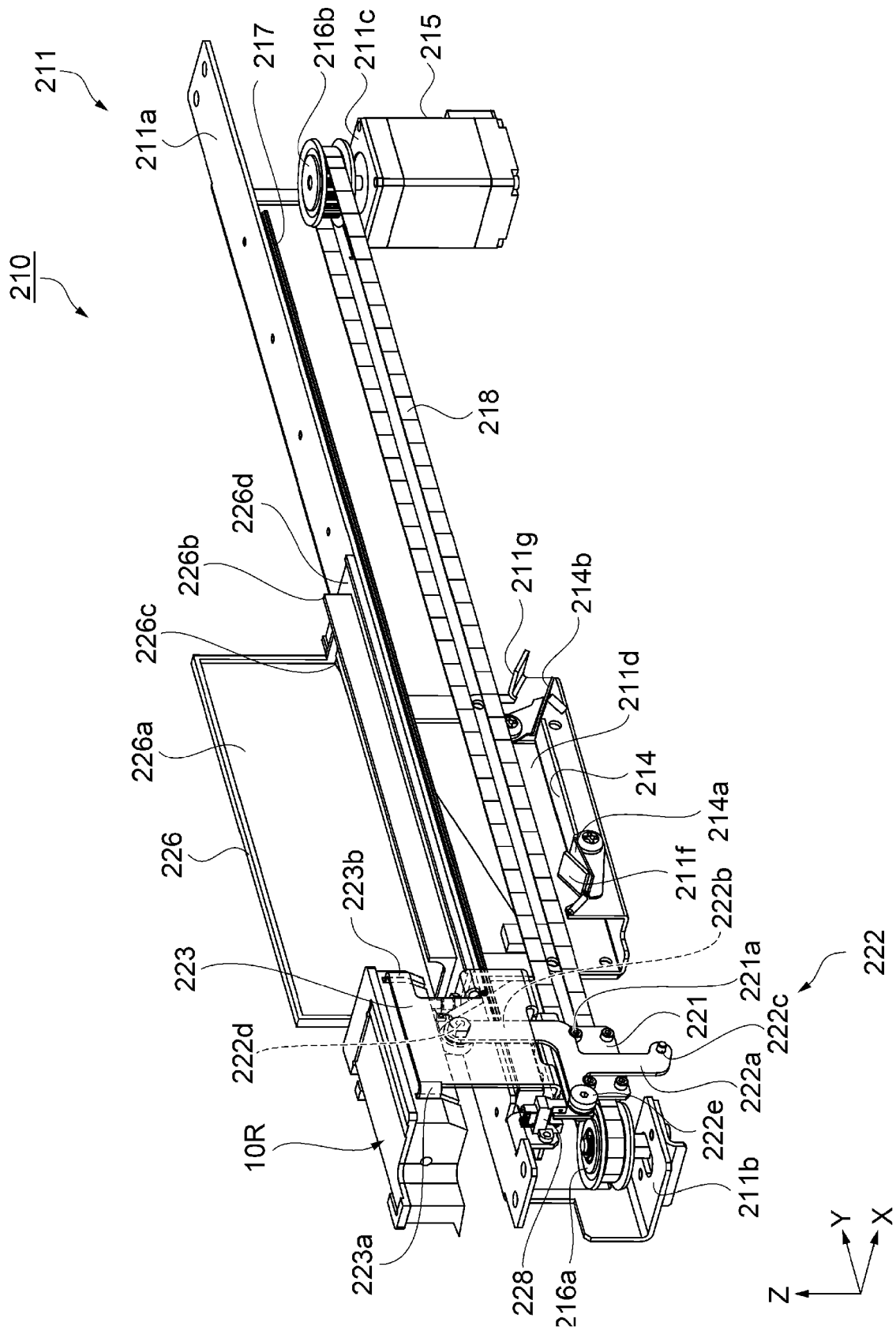

[Fig. 32]
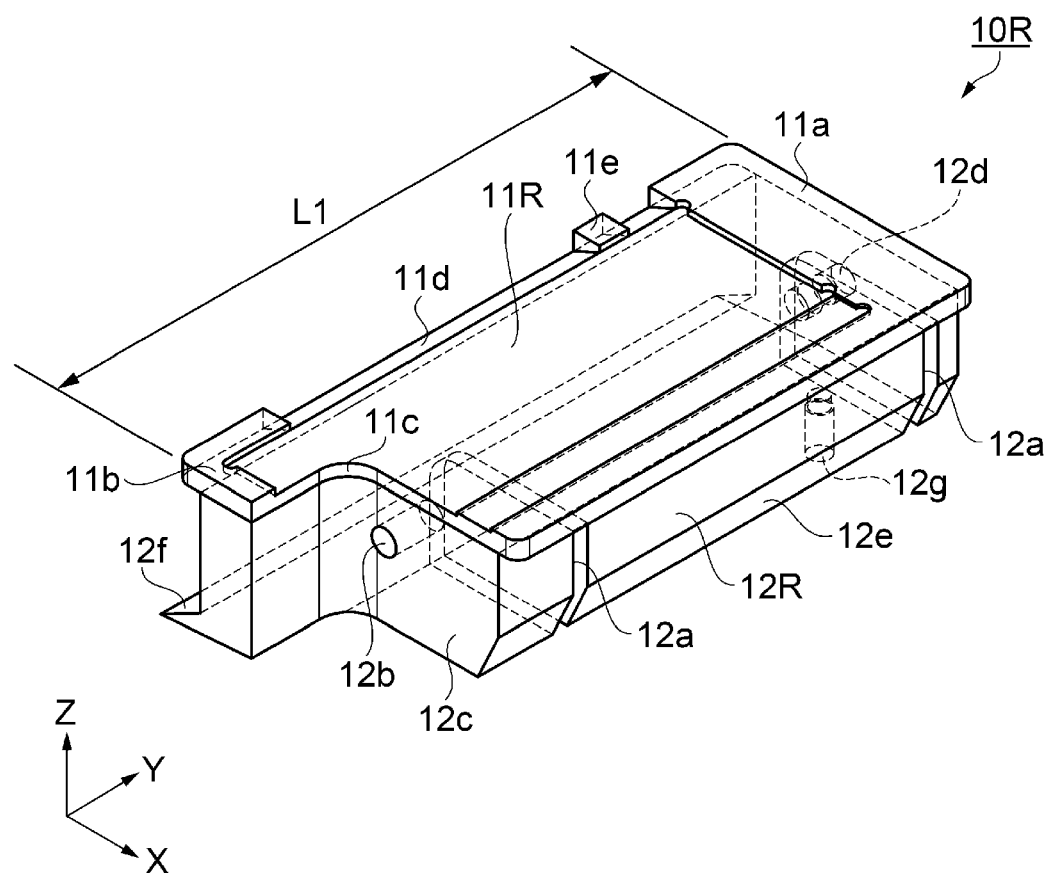

[Fig. 33]
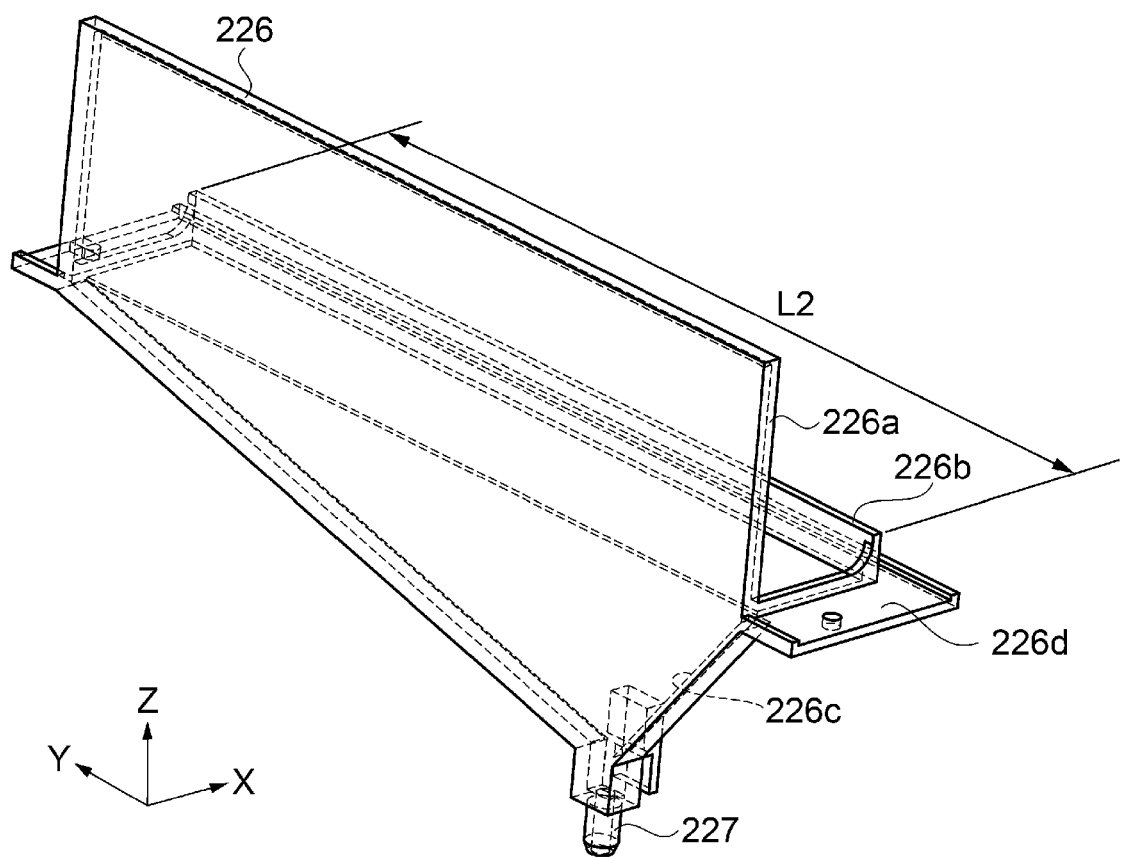

[Fig. 34]
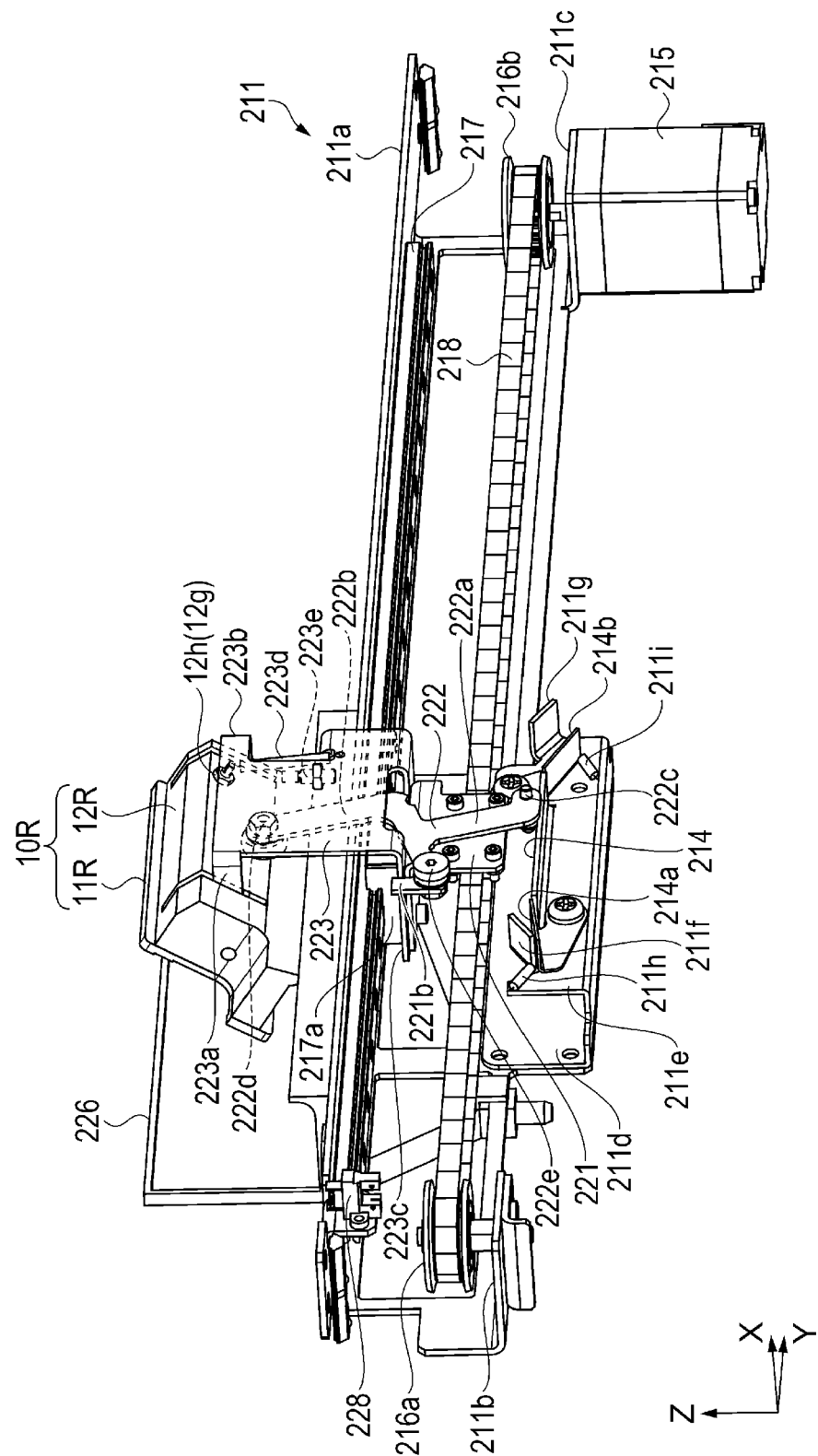

[Fig. 35]
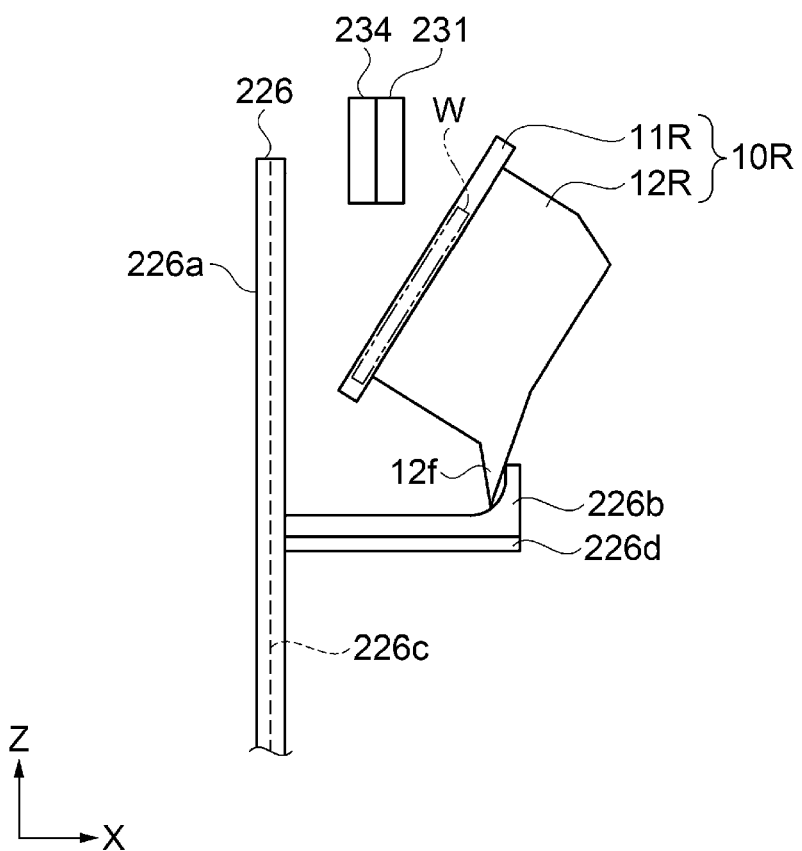

[Fig. 36]
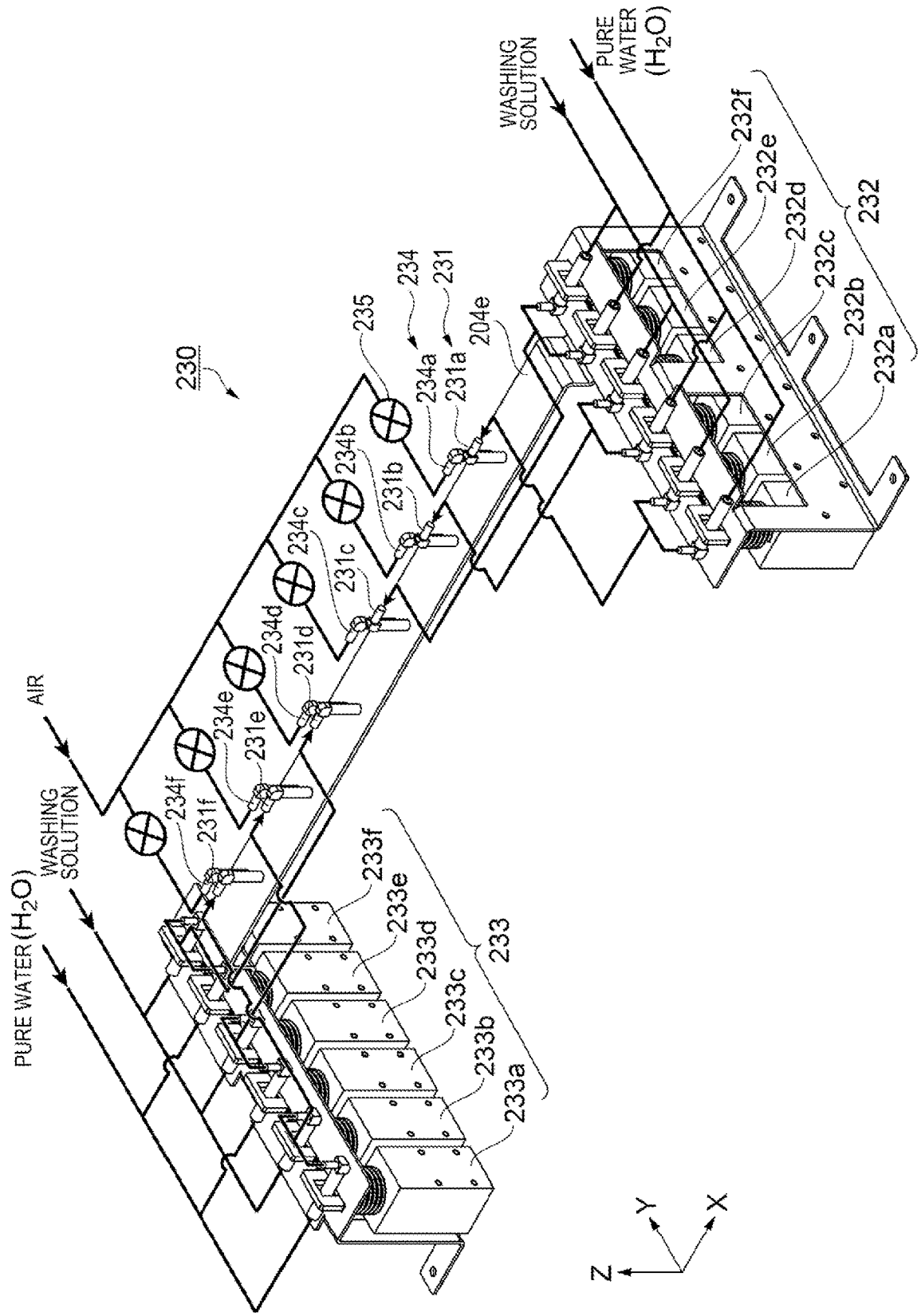

[Fig. 37]
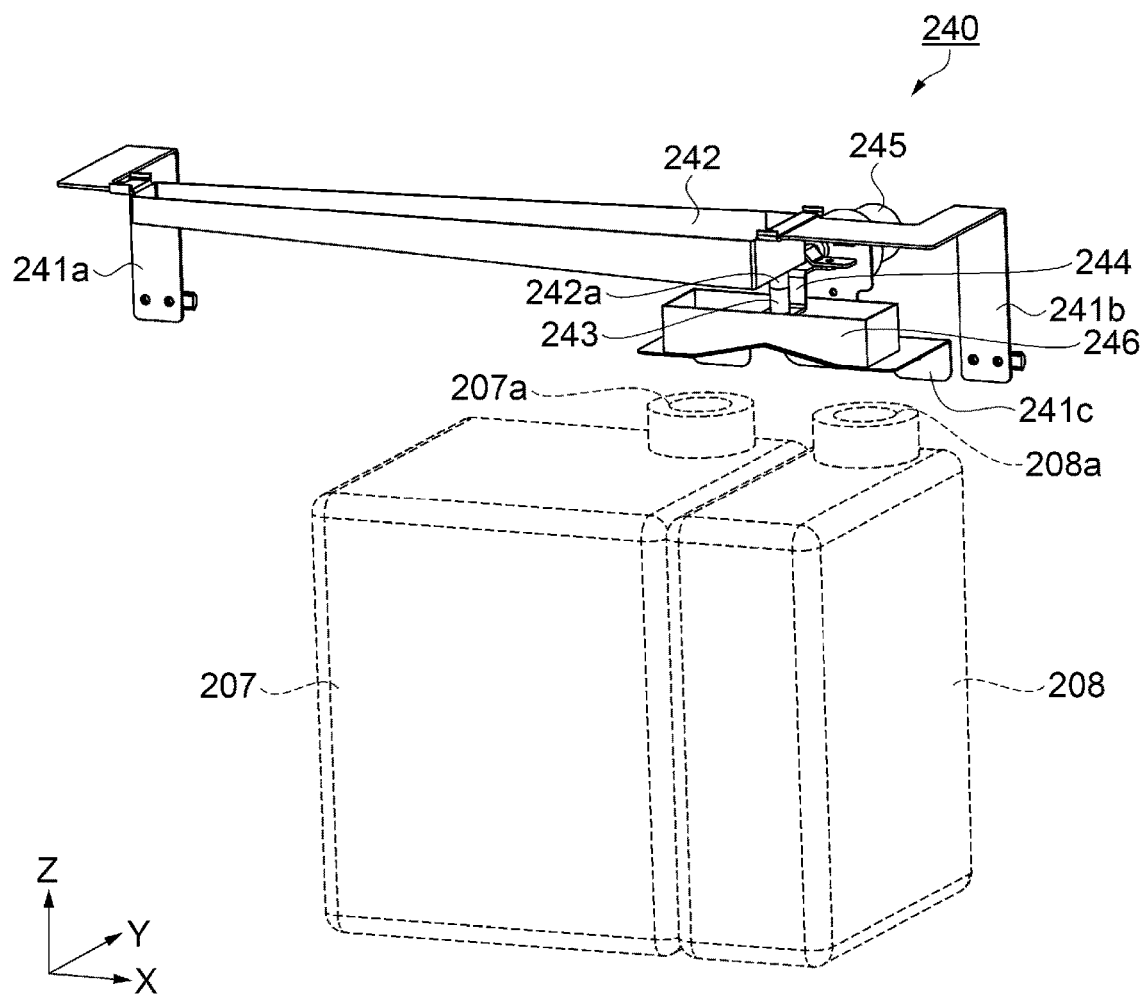

[Fig. 38]
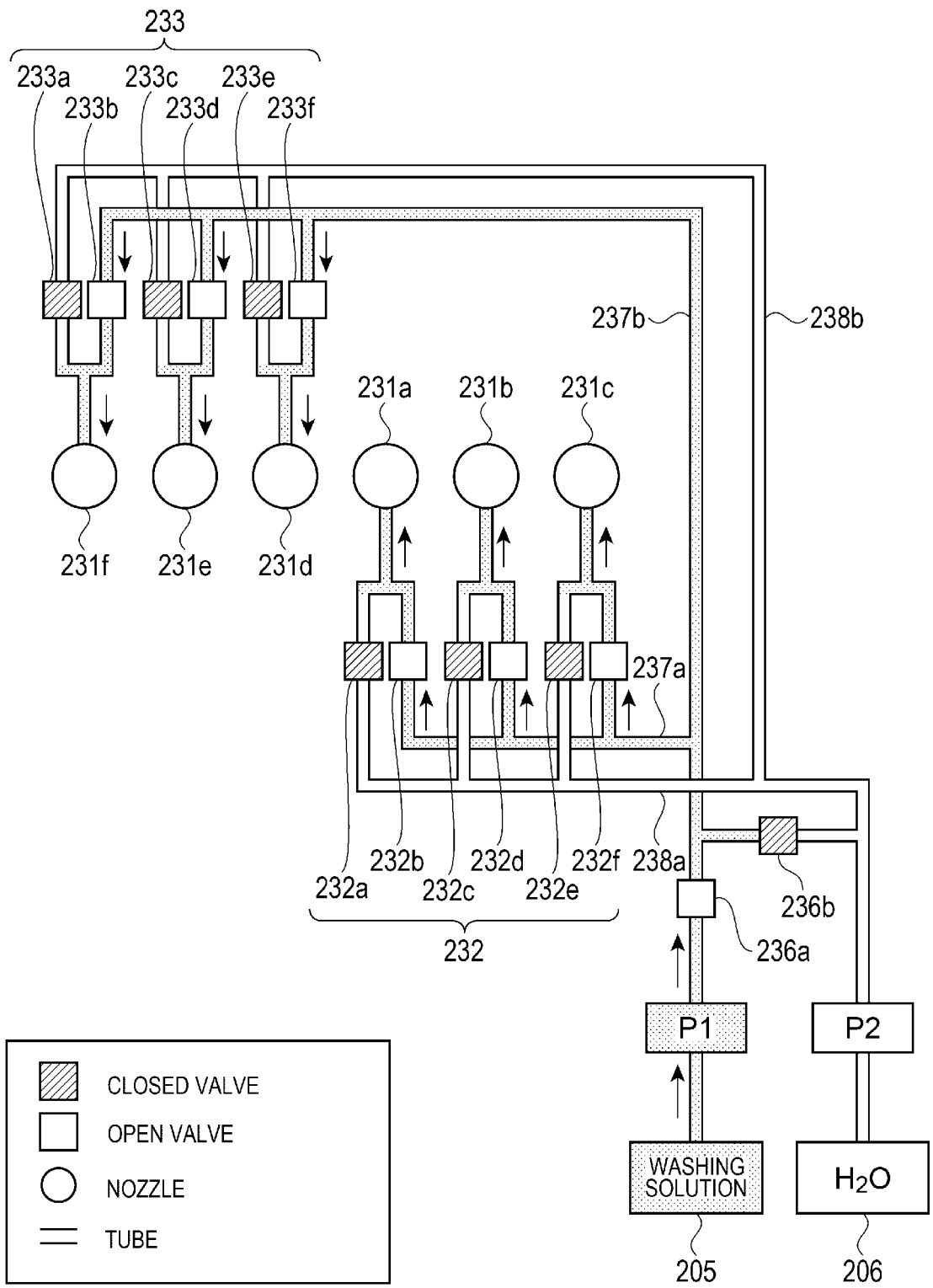

[Fig. 39]
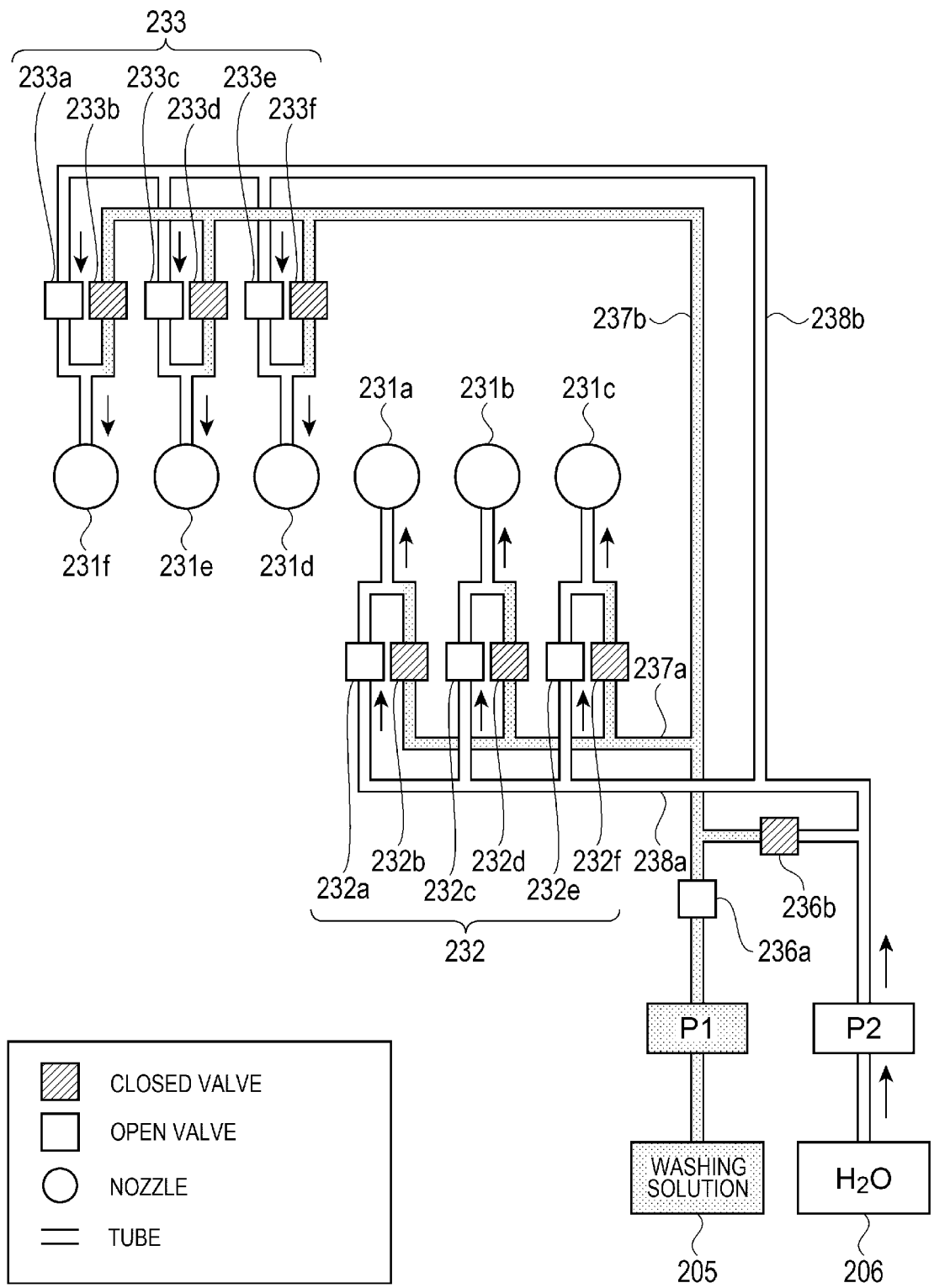

[Fig. 40]
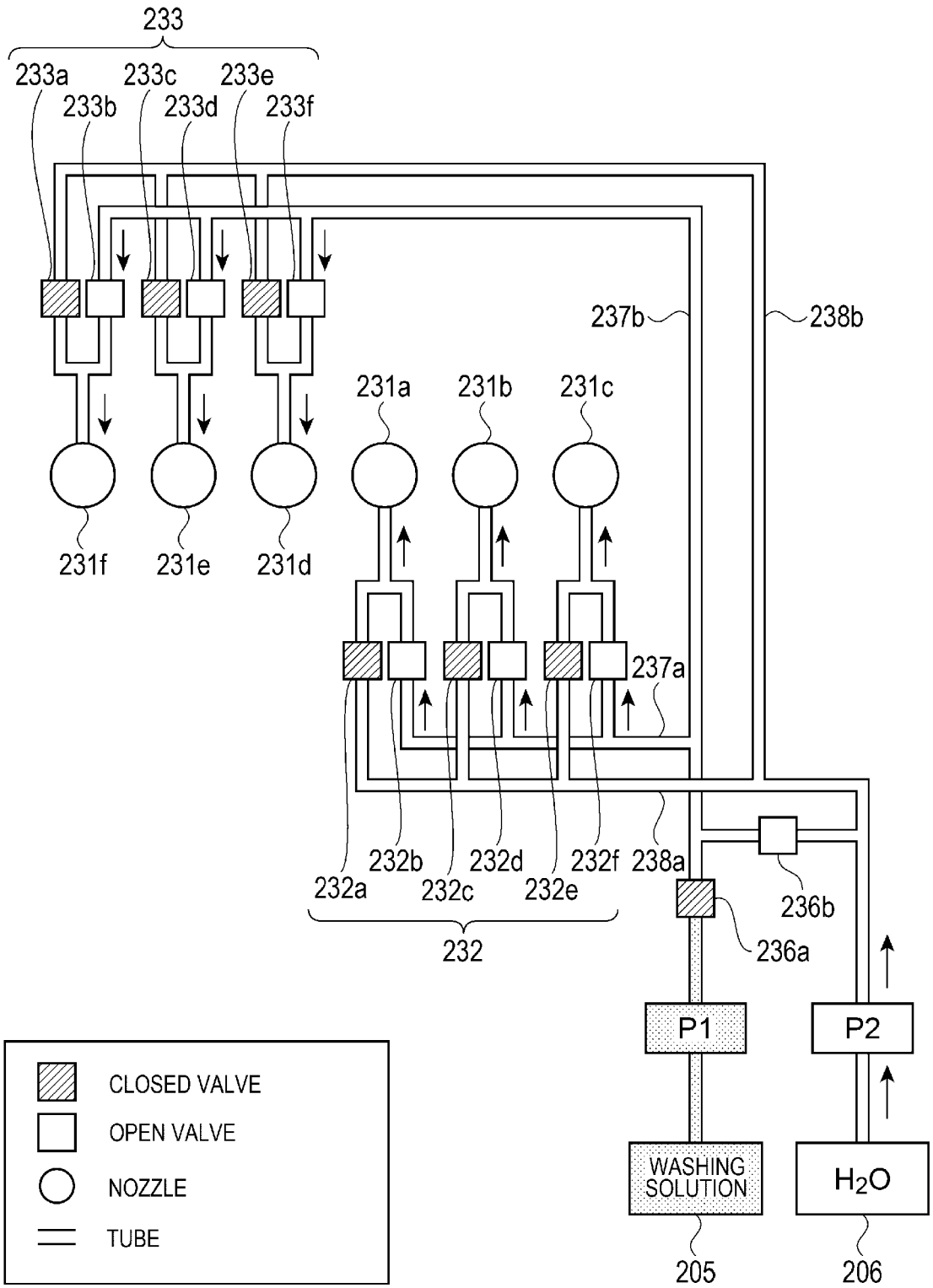

[Fig. 41]
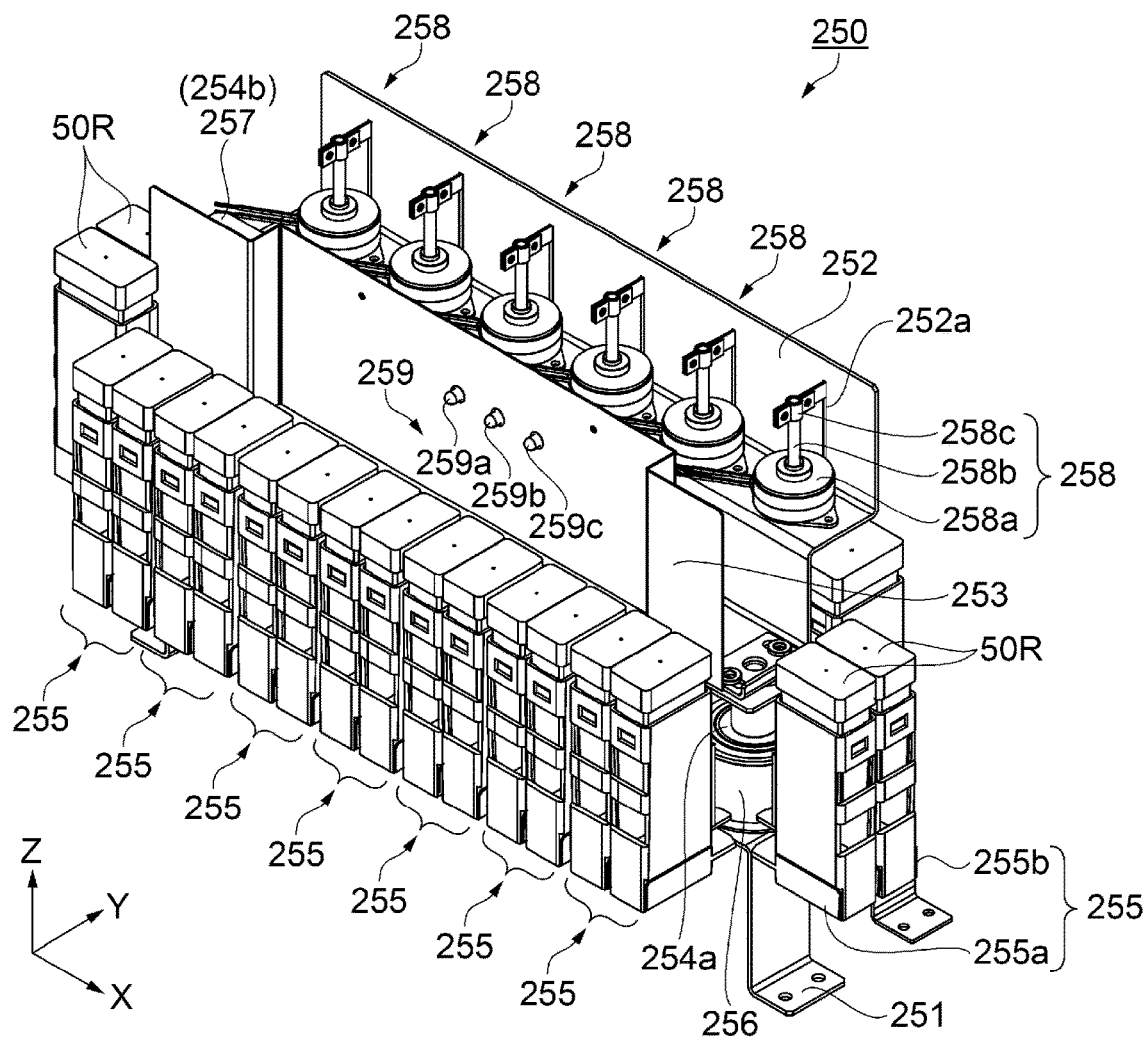

[Fig. 42]
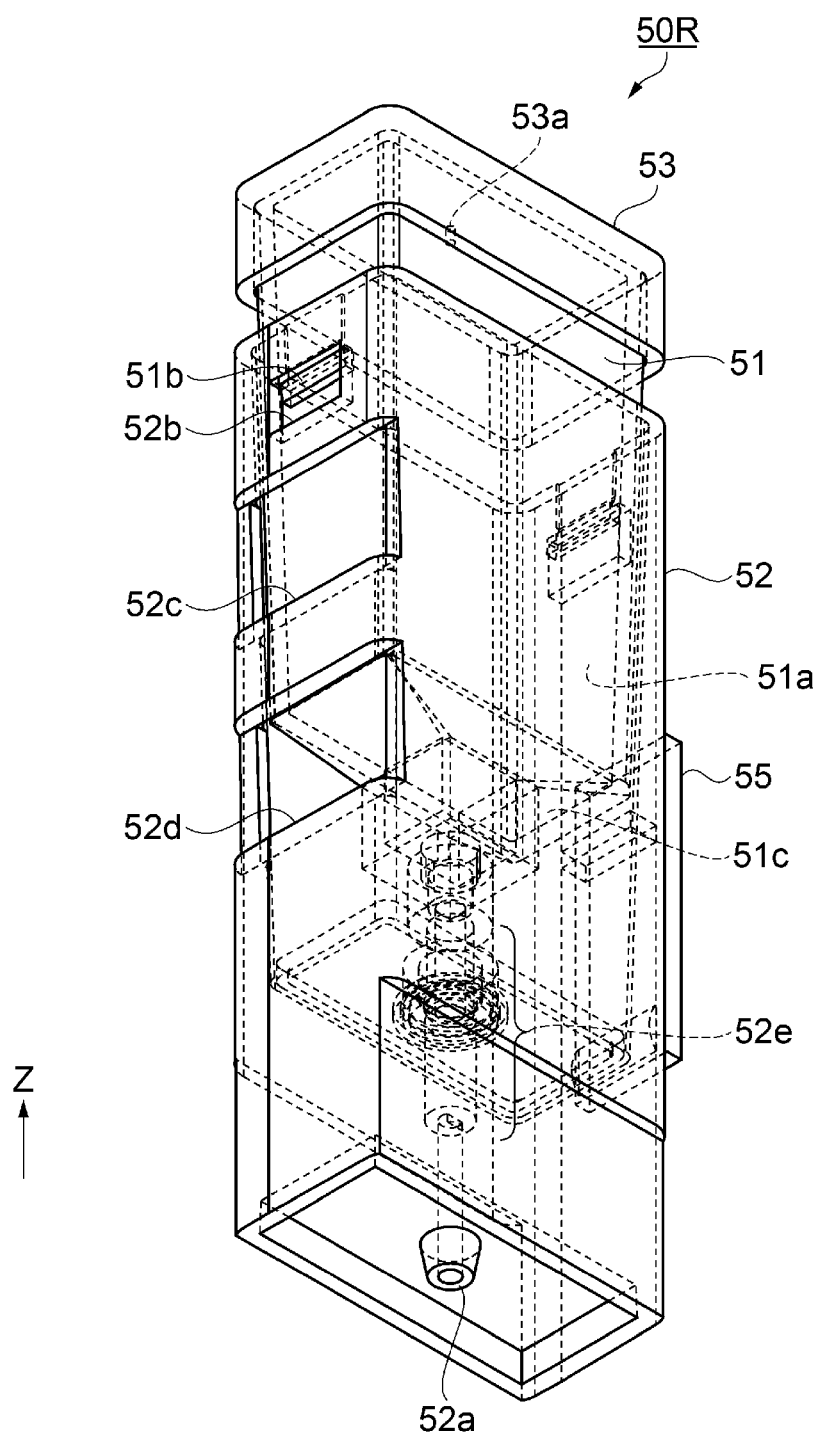

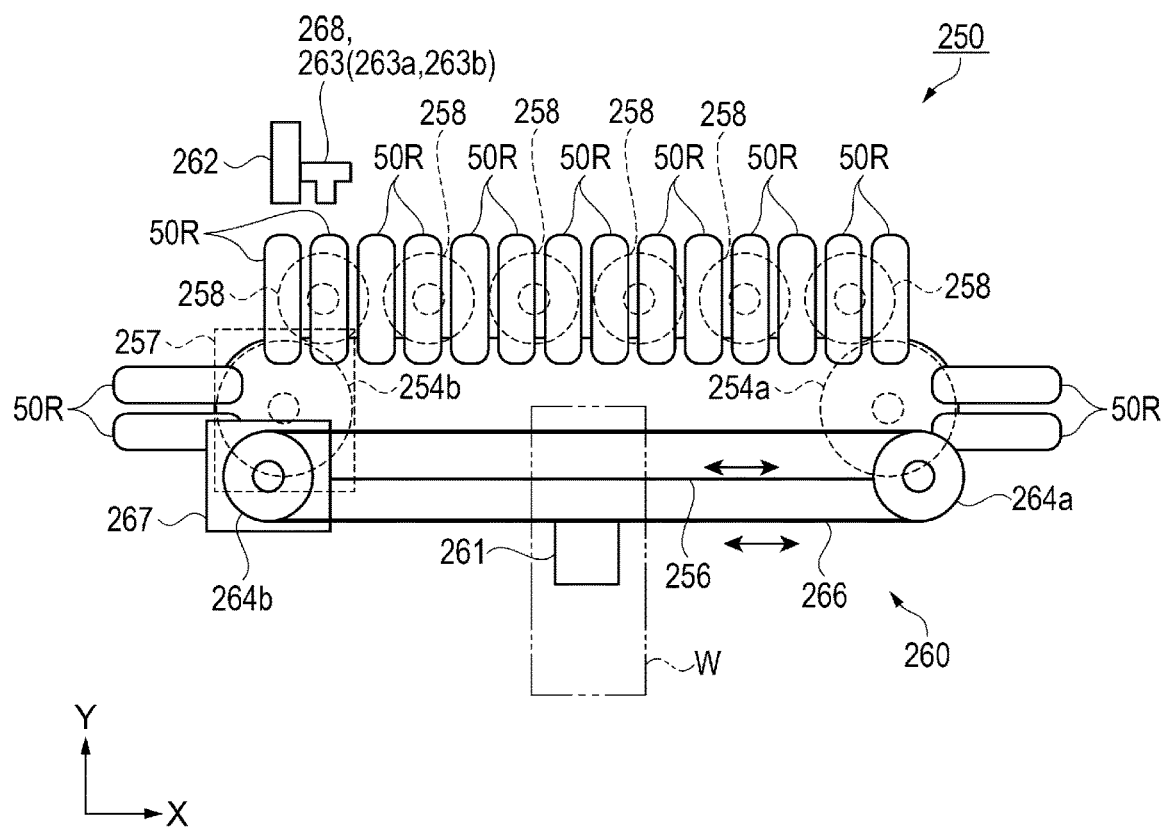
[Fig. 43]

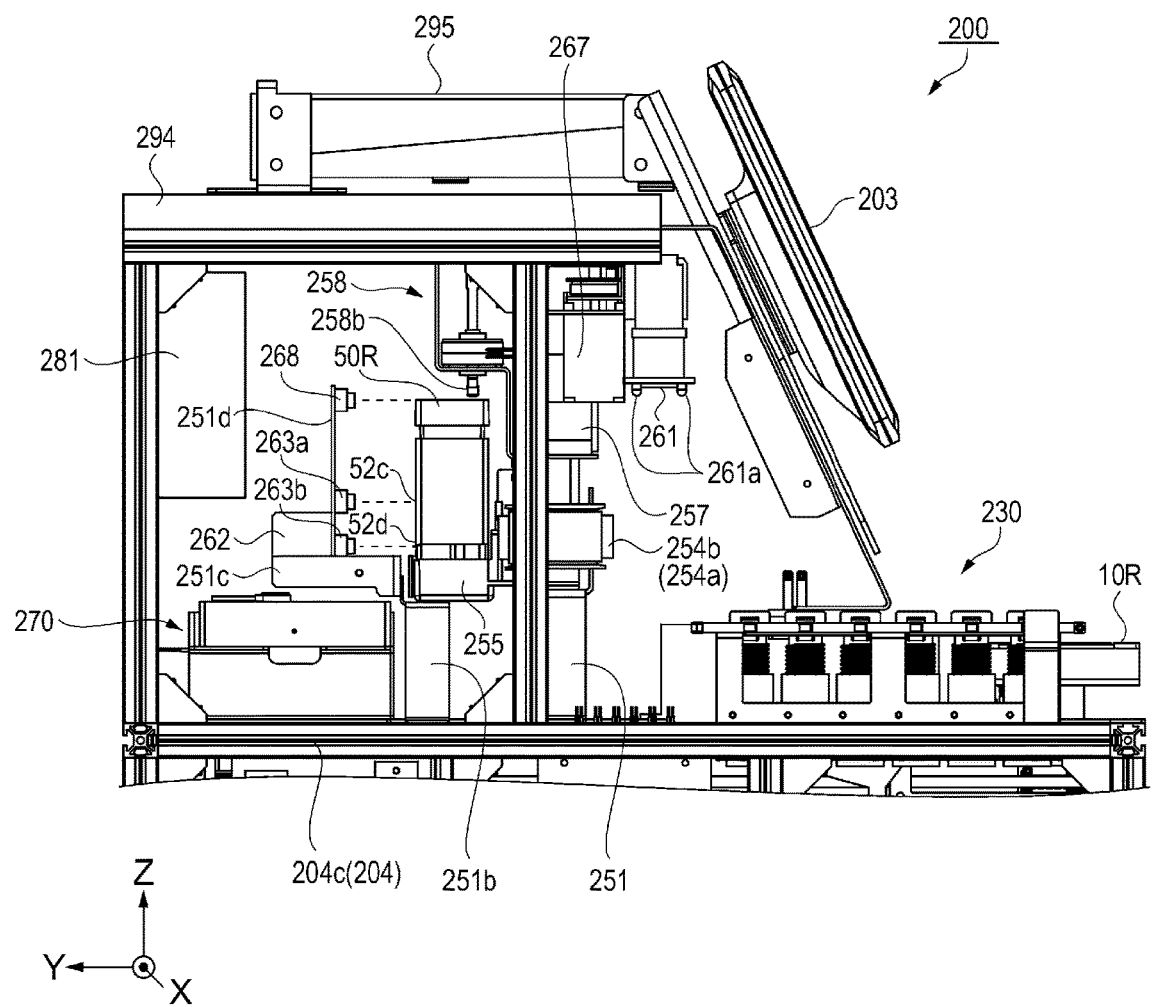
[Fig. 44]

[Fig. 45]
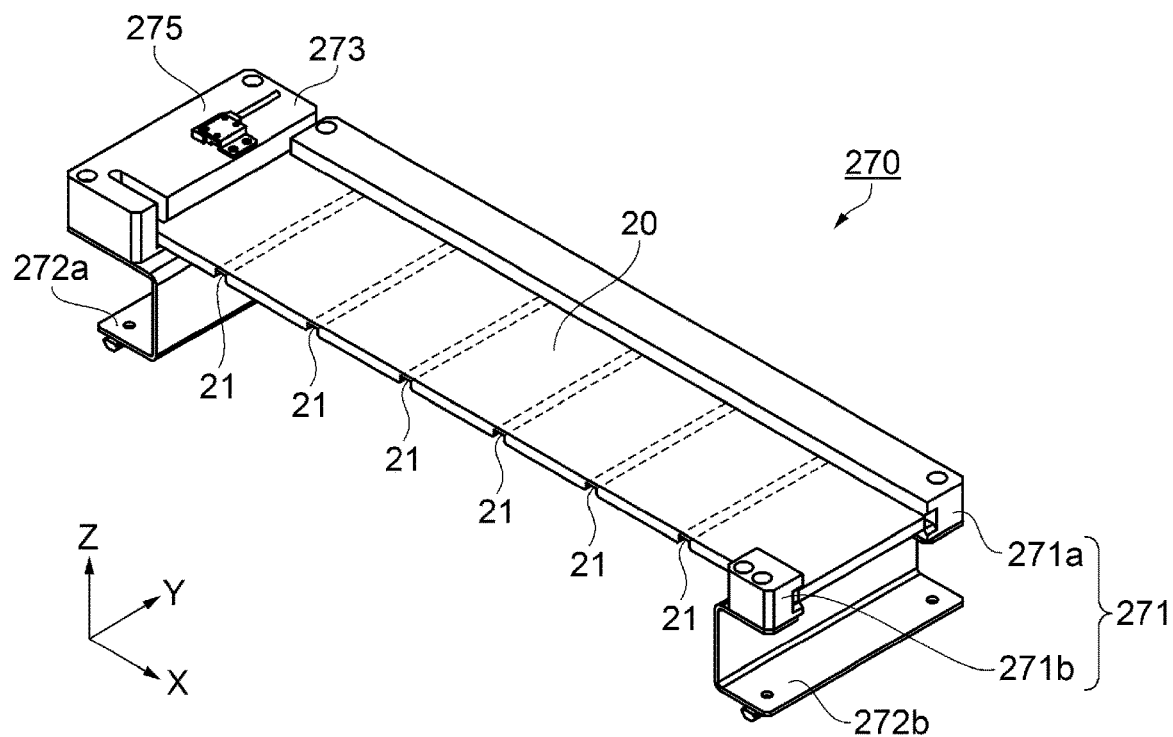

[Fig. 46]
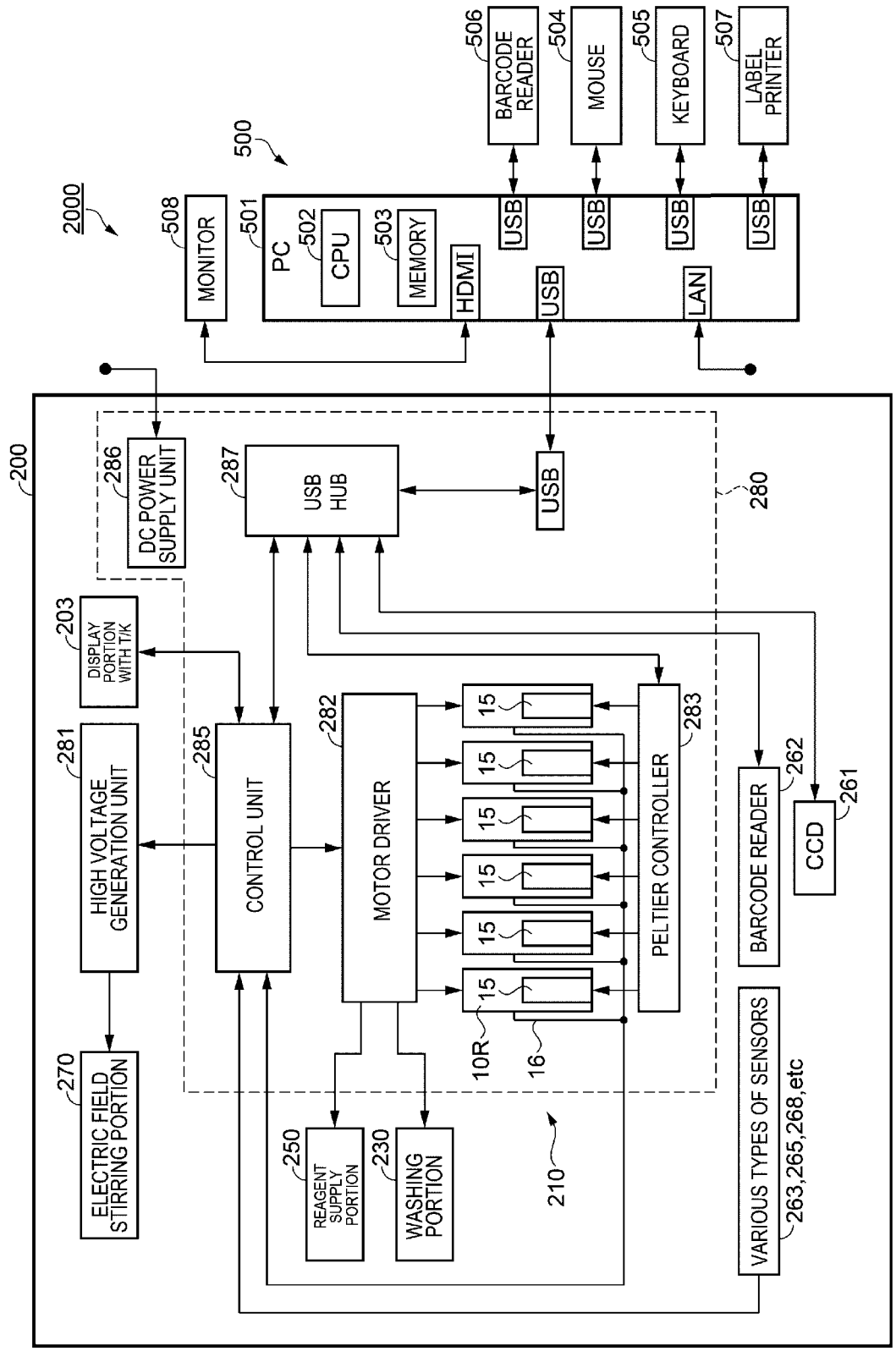

[Fig. 47]

(EXAMPLE 4)

| STEP NAME | USED REAGENT | OPERATION | TIME | |
|---|---|---|---|---|
| SLICING | PIG LIVER BLOCK | | | |
| FIXING | ACETONE | IMMERSION | 2 MIN | |
| WASHING | PBS-T | CONTINUOUS FLOW, SPRAYING AIR | 30 SEC | USING DEVICE |
| REMOVAL OF ENDOGENOUS PO | 3% AQUEOUS HYDROGEN PEROXIDE SOLUTION | LEAVING TO STAND IN 150 μL | 1 MIN | |
| WASHING | PBS-T | CONTINUOUS FLOW, SPRAYING AIR | 30 SEC | |
| PRIMARY ANTIBODY REACTION | PRIMARY ANTIBODY REAGENT | ELECTRIC FIELD STIRRING IN 150 μL | 5 MIN | |
| WASHING | PBS-T | CONTINUOUS FLOW, SPRAYING AIR | 30 SEC | |
| SECONDARY ANTIBODY REACTION | SECONDARY ANTIBODY REAGENT | ELECTRIC FIELD STIRRING IN 150 μL | 5 MIN | |
| WASHING | PBS-T | CONTINUOUS FLOW, SPRAYING AIR | 30 SEC | |
| COLOR DEVELOPMENT | DAB | LEAVING TO STAND IN 150 μL | 3 MIN | |
| WASHING | PURE WATER | CONTINUOUS FLOW, SPRAYING AIR | 2 MIN | |
| NUCLEAR STAINING | HEMATOXYLIN | LEAVING TO STAND IN 150 μL | 1 MIN | |
| WASHING | PURE WATER | CONTINUOUS FLOW, SPRAYING AIR | 2 MIN | |
| ENCAPSULATION | ENCAPSULATING AGENT | COVERING WITH COVER SLIP | 1 MIN | |
| ANALYSIS | — | IMAGE ANALYSIS, DIGITIZING DEPTH OF STAINING | 1 MIN | |
| | | TOTAL | ABOUT 25 MIN | |

[Fig. 48]
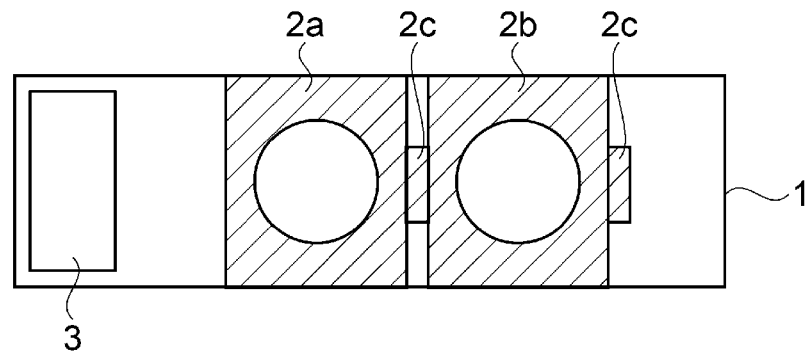
[Fig. 49]
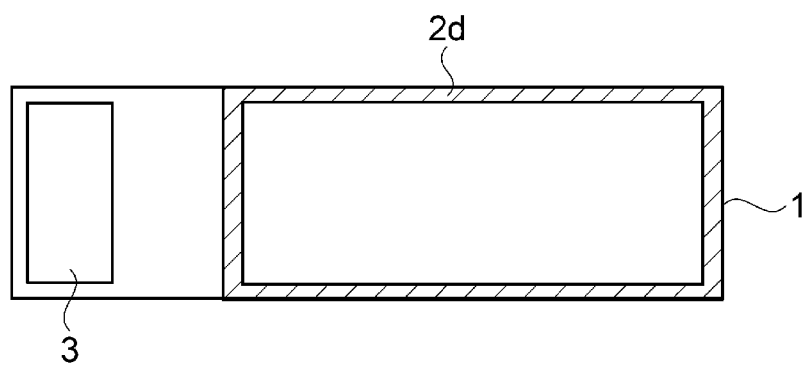
[Fig. 50]
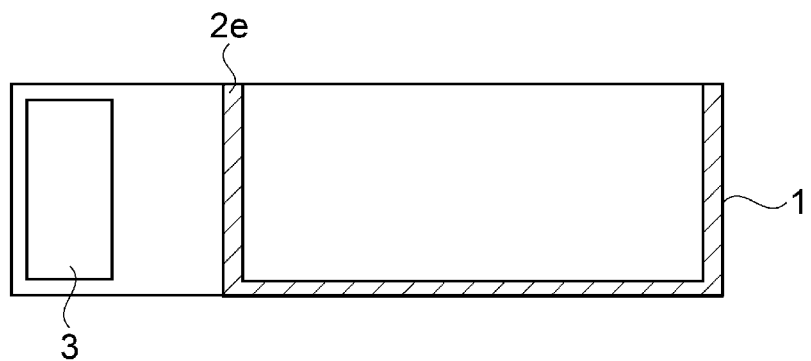

[Fig. 51]
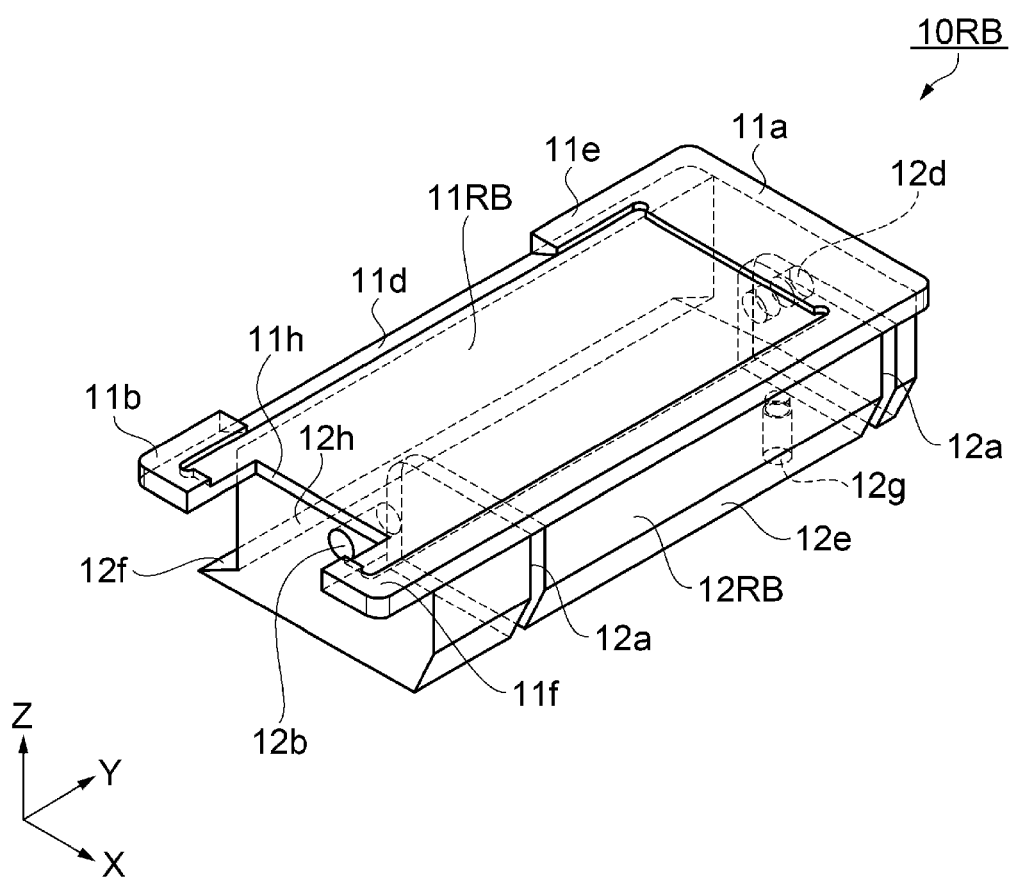

PATHOLOGICAL SPECIMEN PREPARATION DEVICE AND PATHOLOGICAL SPECIMEN PREPARATION SYSTEM

CROSS-REFERENCE TO RELATED APPLICATIONS

This application is a U.S. National Stage Application of International Application No. PCT/JP2017/031401, filed on Aug. 31, 2017, and published in Japanese as WO 2018/043655 A1 on Mar. 8, 2018, which claims priority to Japanese Patent Application No. 2017-158463, filed on Aug. 21, 2017 and Japanese Patent Application No. 2016-170564, filed on Sep. 1, 2016. The entire disclosures of the above applications are incorporated herein by reference.

BACKGROUND

Technical Field

The present invention relates to a pathological specimen preparation device and a pathological specimen preparation system.

Related Art

As a pathological specimen preparation device, for example, JP-2015-155811 discloses an automatic electric field immunohistological staining device including a sample mounting unit having a stage on which a substrate with a tissue specimen fixed thereto is mounted, a solution supply unit including a dropping member that drops a solution containing an antibody onto the tissue specimen on the substrate from a housing portion that houses the solution, an electric field stirring unit including an annular electrode on one side, and a washing unit including a discharge tube that discharges the solution dropped onto the tissue specimen and a supply tube that supplies a washing solution to the tissue specimen.

In the automatic electric field immunohistological staining device of JP-2015-155811, the discharge tube and the supply tube of the washing unit can be put into and taken out of a through-hole in the electrode on one side of the electric field stirring unit. Further, the discharge tube can discharge not only the solution dropped onto the tissue specimen, but also the washing solution supplied to the tissue specimen by the supply tube.

However, in the automatic electric field immunohistological staining device of JP-2015-155811 described above, the discharge tube is inserted into the through-hole of the electrode on one side at such a distance that the discharge tube does not come into contact with the tissue specimen on the substrate, and therefore, it is difficult to completely discharge the solution dropped onto the tissue specimen or the washing solution supplied thereto. If the solution containing the antibody or the washing solution remains, staining using a color developing agent may not be properly carried out.

Further, in JP-2015-155811 described above, it is necessary to collect the tissue specimen in a size capable of being fixed inside a water-repelling ring formed on the substrate, however, the tissue specimen sometimes does not fit inside the water-repelling ring depending on the way of collecting the tissue specimen. In such a case, there arises a problem that it becomes further difficult to perform sufficient electric field stirring of the solution dropped onto a necessary portion of the tissue specimen, or to perform reliable discharge of the solution and the washing solution by the discharge tube.

SUMMARY

The invention has been made for solving at least a part of the problems described above, and can be implemented as the following forms or application examples.

Application Example

A pathological specimen preparation device according to this application example includes a stage portion including a stage on which a substrate having a tissue specimen fixed thereto is mounted, a reagent supply portion capable of supplying a reagent to the substrate mounted on the stage, a washing portion capable of supplying a washing solution to the substrate mounted on the stage, an electric field stirring portion capable of stirring the reagent or the washing solution supplied to the substrate mounted on the stage by applying an electric field to the reagent or the washing solution, a control unit, a stage transport mechanism that moves the stage in a first direction in which the washing portion, the reagent supply portion, and the electric field stirring portion are sequentially disposed, and a stage tilting mechanism that tilts the stage in a second direction crossing the first direction when the stage is positioned in the washing portion, wherein the control unit drives and controls the stage transport mechanism according to a pathological specimen preparation protocol so as to move the stage on which the substrate is mounted in the first direction.

According to the configuration of this application example, the control unit drives and controls the stage transport mechanism according to the pathological specimen preparation protocol, so that the substrate having a tissue specimen fixed thereto can be disposed with respect to each of the washing portion, the reagent supply portion, and the electric field stirring portion disposed in the first direction. For example, the stage is positioned in the reagent supply portion so as to supply the reagent containing an antibody to the tissue specimen, and thereafter, the stage is positioned in the electric field stirring portion so as to stir the reagent, whereby an antigen-antibody reaction can be performed. Thereafter, the stage is positioned in the washing portion so as to supply the washing solution, whereby the tissue specimen after completion of the antigen-antibody reaction can be washed. In addition, when the stage is positioned in the washing portion, the stage is tilted in a second direction crossing the first direction by the stage tilting mechanism, and therefore, the supplied reagent or washing solution can be reliably discharged from the top of the substrate. That is, the pathological specimen preparation device capable of properly preparing a pathological specimen according to the pathological specimen preparation protocol can be provided.

In the pathological specimen preparation device according to the above-mentioned application example, it is preferred that the stage tilting mechanism tilts the stage by 60° or more in the second direction from a horizontal state.

According to this configuration, the supplied reagent or washing solution can be more reliably discharged from the top of the substrate.

In the pathological specimen preparation device according to the above-mentioned application example, it is preferred that the stage tilting mechanism has a support mechanism that pushes up the stage from the lower side and tilts the stage with the movement of the stage to the washing portion.

According to this configuration, the stage can be tilted in the second direction with a relatively simple configuration.

In the pathological specimen preparation device according to the above-mentioned application example, it is preferred that the stage portion includes the stage, the stage transport mechanism, and the stage tilting mechanism.

According to this configuration, the stage portion can be replaced including the stage transport mechanism and the stage tilting mechanism, and therefore, the maintainability of the stage portion is improved.

In the pathological specimen preparation device according to the above-mentioned application example, it is preferred that a plurality of the stage portions are arranged in parallel in the second direction, the reagent supply portion can supply the reagent to the substrate mounted on the stage of each of the plurality of the stage portions, the washing portion can supply the washing solution to the substrate mounted on the stage of each of the plurality of the stage portions, the electric field stirring portion is provided across the plurality of the stage portions in the second direction, and includes an electrode on one side capable of applying an electric field to the reagent or the washing solution supplied to the substrate mounted on the stage.

According to this configuration, the pathological specimen preparation device capable of simultaneously preparing a plurality of pathological specimens using, for example, a plurality of tissue specimens collected from the same subject or a plurality of tissue specimens collected from different subjects can be provided.

In the pathological specimen preparation device according to the above-mentioned application example, it is preferred that the reagent is filled in a cartridge capable of ejecting the reagent, the reagent supply portion includes a plurality of holding portions capable of attaching and detaching the cartridge, and a transport portion capable of transporting the plurality of holding portions in the second direction, and the control unit drives and controls the transport portion according to the pathological specimen preparation protocol so as to move at least one of the plurality of holding portions to a position opposed to the stage.

According to this configuration, a plurality of types of reagents can be independently supplied to the tissue specimens according to the pathological specimen preparation protocol. In other words, the pathological specimen preparation protocol using a plurality of types of reagents can be performed by one device.

In the pathological specimen preparation device according to the above-mentioned application example, it is preferred that the device further includes a barcode reader capable of reading a barcode given to the cartridge.

According to this configuration, the traceability of the reagent used when preparing the pathological specimen and the pathological specimen can be achieved.

In the pathological specimen preparation device according to the above-mentioned application example, it is preferred that the cartridge has a light transmissive housing portion capable of housing the reagent, and the device includes a residual amount detection sensor capable of optically detecting the presence or absence of the reagent in the housing portion.

According to this configuration, the presence or absence of the reagent in the cartridge can be detected by the residual amount detection sensor, and therefore, the pathological specimen preparation device capable of effectively utilizing the reagent can be provided.

In the pathological specimen preparation device according to the above-mentioned application example, it is preferred that the washing portion includes a nozzle, a plurality of washing solution tanks, and a valve capable of switching the connection destination of the nozzle to the plurality of washing solution tanks, and the control unit drives and controls the valve according to the pathological specimen preparation protocol so as to connect the nozzle to one of the plurality of washing solution tanks.

According to this configuration, different types of washing solutions can be stored in the plurality of washing solution tanks, and the tissue specimen can be washed by ejecting each of the different types of washing solutions from the nozzle.

In the pathological specimen preparation device according to the above-mentioned application example, it is preferred that pure water is filled in one of the plurality of washing solution tanks as the washing solution.

According to this configuration, the reagent supplied to the tissue specimen can be washed with pure water. That is, the washability of the tissue specimen is improved. Further, for example, in the case where the washing solution which generates a foreign substance such as a salt after drying is used, a supply path such as a nozzle may be blocked by the foreign substance, however, by washing the supply path of the washing solution with pure water, the foreign substance is removed, and therefore, stable supply of the washing solution can be realized.

In the pathological specimen preparation device according to the above-mentioned application example, it is preferred that the washing portion includes a nozzle connected to a gas supply unit through a valve, and the control unit controls the opening and closing of the valve according to the pathological specimen preparation protocol so as to spray a gas on the substrate mounted on the stage from the nozzle when the stage is positioned in the washing portion.

According to this configuration, the reagent or the washing solution supplied to the substrate mounted on the stage is discharged by tilting the stage by the stage tilting mechanism, and also a gas is sprayed on the substrate from the nozzle connected to a gas supply unit, and therefore, the reagent or the washing solution can be more reliably discharged.

In the pathological specimen preparation device according to the above-mentioned application example, it is preferred that the device further includes a waste liquid tank and a discharge flow path that discharges the reagent or the washing solution flowing down from the substrate on the tilted stage toward the waste liquid tank when the stage is positioned in the washing portion.

According to this configuration, the reagent or the washing solution flowing down from the substrate on the stage can be recovered in the waste liquid tank without leakage.

In the pathological specimen preparation device according to the above-mentioned application example, it is preferred that the waste liquid tank includes a first waste liquid tank and a second waste liquid tank, the discharge flow path includes a first discharge flow path toward the first waste liquid tank and a second discharge flow path toward the second waste liquid tank, the device further includes a flow path switching mechanism capable of allowing the reagent or the washing solution flowing down from the substrate on the tilted stage to flow in the first discharge flow path or the second discharge flow path, and the control unit controls the flow path switching mechanism depending on the type of the reagent or the washing solution according to the pathological specimen preparation protocol so as to switch the discharge destination of the reagent or the washing solution to the first discharge flow path or the second discharge flow path.

According to this configuration, in the pathological specimen preparation protocol, for example, even if a reagent which differs in handling in the waste liquid is used, the reagent can be reliably separated and recovered in the first waste liquid tank or the second waste liquid tank. In other words, as compared with the case where all the reagents are mixed and recovered in the waste liquid tank, the handling of the waste liquid can be managed separately for each reagent.

In the pathological specimen preparation device according to the above-mentioned application example, it is preferred that the device further includes an image capture portion capable of capturing an image of the substrate mounted on the stage.

According to this configuration, the image of the substrate having the tissue specimen fixed thereto can be captured by the image capture portion, and therefore, the information of the captured image of the substrate and the pathological specimen preparation protocol can be managed in association with each other. That is, the traceability in the pathological specimen preparation can be improved.

In the pathological specimen preparation device according to the above-mentioned application example, it is preferred that the device includes a display portion that can display information related to the pathological specimen preparation protocol and has an input unit associated with the operation of the pathological specimen preparation protocol.

According to this configuration, an operator can operate the pathological specimen preparation device while confirming the information related to the pathological specimen preparation protocol, and therefore can efficiently perform the operation as compared with the case where the operator operates the pathological specimen preparation device separately using a computer or the like having an input unit such as a keyboard.

Application Example

A pathological specimen preparation system according to this application example includes the pathological specimen preparation device according to the above-mentioned application example and a computer having a memory portion that stores a pathological specimen preparation protocol, wherein the computer drives and controls the pathological specimen preparation device according to the pathological specimen preparation protocol.

According to this application example, the pathological specimen preparation system capable of properly preparing a pathological specimen according to the pathological specimen preparation protocol can be provided. Further, not all the control functions are imparted to the pathological specimen preparation device, and some control functions can be left to the computer, and therefore, the pathological specimen preparation device can be simplified. Further, when a computer is integrated into a designated network, the preparation outcome and the preparation process of the pathological specimen can also be comprehensively managed.

In the pathological specimen preparation system according to the above-mentioned application example, it is preferred that a reagent is filled in a cartridge which can eject the reagent and is given a barcode, and the computer obtains the information of the reagent associated with the barcode of the cartridge and collates the information with the information of the reagent according to the pathological specimen preparation protocol.

According to this configuration, the management of the reagent designated by the pathological specimen preparation protocol can be ensured.

In the pathological specimen preparation system according to the above-mentioned application example, it is preferred that the reagent is ejected from the cartridge which has a light transmissive housing portion capable of housing the reagent, the pathological specimen preparation device includes a residual amount detection sensor capable of optically detecting the presence or absence of the reagent in the housing portion, and the computer detects the residual amount of the reagent with the residual amount detection sensor at least before starting the preparation of a pathological specimen according to the pathological specimen preparation protocol.

According to this configuration, the residual amount of the reagent in the cartridge can be detected by the residual amount detection sensor, and therefore, the pathological specimen preparation system capable of ensuring the management of the residual amount of the reagent in the cartridge so that when preparing a pathological specimen, for example, a problem such as interruption of the preparation due to a shortage of the reagent in the middle of the preparation does not occur can be provided. Further, by ensuring the management of the residual amount of the reagent in the cartridge, the accuracy of the replacement time for the cartridge or the inventory management thereof can be improved, and therefore, the cost associated with the inventory management of the cartridge can also be reduced.

In the pathological specimen preparation system according to the above-mentioned application example, it is preferred that the computer transports the substrate to the washing portion and allows pure water as the washing solution to be supplied to the substrate from the washing portion according to the pathological specimen preparation protocol when a standing time after the tissue specimen fixed to the substrate is allowed to develop a color and then washed reaches a predetermined time.

According to this configuration, even if the preparation of the pathological specimen is completed while an operator is away from the pathological specimen preparation system, pure water as the washing solution is supplied to the prepared pathological specimen as appropriate, and therefore, a problem such as a change in the color developed state due to drying of the pathological specimen can be prevented.

In the pathological specimen preparation system according to the above-mentioned application example, it is preferred that the computer obtains an image of the substrate and the tissue specimen fixed to the substrate, and performs an operation of associating the obtained image with the pathological specimen preparation protocol.

According to this configuration, the pathological specimen preparation protocol and the information of the pathological specimen prepared according to the pathological specimen preparation protocol can be managed in association with each other, and the traceability in the pathological specimen preparation can be improved.

BRIEF DESCRIPTION OF THE DRAWINGS

FIG. 1 is a perspective view showing a work having a tissue specimen fixed thereto.

FIG. 2 is a schematic view showing a step of preparing a pathological specimen.

FIG. 3 is a view illustrating a principle of an electric field stirring step.

FIG. 4 is a schematic perspective view showing a configuration of a pathological specimen preparation device of a first embodiment.

FIG. 5 is a schematic perspective view showing a configuration of a stage portion of the first embodiment.

FIG. 6 is a schematic perspective view showing a stage of the first embodiment.

FIG. 7 is a schematic perspective view showing a liquid discharge guide portion of the first embodiment.

FIG. 8 is a principal part perspective view illustrating a stage tilting mechanism of the first embodiment.

FIG. 9 is a principal part perspective view illustrating the stage tilting mechanism of the first embodiment.

FIG. 10 is a view showing a positional relationship between the tilted stage and the other configuration of the first embodiment.

FIG. 11 is a schematic perspective view showing a configuration of a washing portion of the first embodiment.

FIG. 12 is a schematic perspective view showing a configuration of a flow path switching mechanism of the first embodiment.

FIG. 13 is a schematic view showing a way of supplying the washing solution of the first embodiment.

FIG. 14 is a schematic view showing the way of supplying the washing solution of the first embodiment.

FIG. 15 is a schematic view showing the way of supplying the washing solution of the first embodiment.

FIG. 16 is a schematic perspective view showing a configuration of a reagent supply portion of the first embodiment.

FIG. 17 is a perspective view showing a cartridge of the first embodiment.

FIG. 18 is a schematic plan view for illustrating the movement of the reagent supply portion of the first embodiment.

FIG. 19 is a schematic perspective view showing a configuration of an electric field stirring portion of the first embodiment.

FIG. 20 is a schematic cross-sectional view showing the shape of an electrode of the electric field stirring portion of the first embodiment.

FIG. 21 is a schematic perspective view showing an exterior cover of the pathological specimen preparation device of the first embodiment.

FIG. 22 is a block diagram showing an electrical and mechanical configuration of a pathological specimen preparation system of the first embodiment.

FIG. 23 is a table showing a step of preparing a pathological specimen by immunohistochemical staining of Example 1.

FIG. 24 is a table showing a step of preparing a pathological specimen in immunohistochemical staining of Comparative Example 1.

FIG. 25 is a table showing a step of preparing a pathological specimen by immunohistochemical staining of Example 2.

FIG. 26 is a table showing a step of preparing a pathological specimen in immunohistochemical staining of Comparative Example 2.

FIG. 27 is a table showing a step of preparing a pathological specimen by in situ hybridization of Example 3.

FIG. 28 is a table showing a step of preparing a pathological specimen in in situ hybridization of Comparative Example 3.

FIG. 29 is a schematic perspective view showing an exterior of a pathological specimen preparation device of a second embodiment.

FIG. 30 is a schematic perspective view showing a configuration of the pathological specimen preparation device of the second embodiment.

FIG. 31 is a schematic perspective view showing a configuration of a stage portion of the second embodiment.

FIG. 32 is a schematic perspective view showing a stage of the second embodiment.

FIG. 33 is a schematic perspective view showing a liquid discharge guide portion of the second embodiment.

FIG. 34 is a schematic perspective view illustrating a stage tilting mechanism of the second embodiment.

FIG. 35 is a view showing a positional relationship between the tilted stage and the other configuration of the second embodiment.

FIG. 36 is a schematic perspective view showing a configuration of a washing portion of the second embodiment.

FIG. 37 is a schematic perspective view showing a configuration of a flow path switching mechanism of the second embodiment.

FIG. 38 is a piping system diagram showing a way of supplying the washing solution in the second embodiment.

FIG. 39 is a piping system diagram showing the way of supplying the washing solution in the second embodiment.

FIG. 40 is a piping system diagram showing the way of supplying the washing solution in the second embodiment.

FIG. 41 is a schematic perspective view showing a configuration of a reagent supply portion of the second embodiment.

FIG. 42 is a perspective view showing a cartridge of the second embodiment.

FIG. 43 is a schematic plan view showing the arrangement of the respective portions associated with the reagent supply portion of the second embodiment.

FIG. 44 is a schematic side view showing the arrangement of the respective portions associated with the reagent supply portion of the second embodiment.

FIG. 45 is a schematic perspective view showing a configuration of an electric field stirring portion of the second embodiment.

FIG. 46 is a block diagram showing an electrical and mechanical configuration of a pathological specimen preparation system of the second embodiment.

FIG. 47 is a table showing a step of preparing a pathological specimen by immunohistochemical staining of Example 4.

FIG. 48 is a schematic plan view showing a configuration of a substrate of a modification example.

FIG. 49 is a schematic plan view showing a configuration of a substrate of a modification example.

FIG. 50 is a schematic plan view showing a configuration of a substrate of a modification example.

FIG. 51 is a schematic perspective view showing a stage of a modification example

DETAILED DESCRIPTION

Hereinafter, embodiments embodying the invention will be described with reference to the drawings. Incidentally, the drawings to be used are displayed by appropriately enlarging or reducing the size so that portions to be described are in a recognizable state.

First Embodiment

<Method for Preparing Pathological Specimen>

First, basic steps in a method for preparing a pathological specimen of this embodiment will be described with reference to FIG. 1 to FIG. 3. FIG. 1 is a perspective view showing a work having a tissue specimen fixed thereto, FIG. 2 is a schematic view showing a step of preparing a pathological specimen, and FIG. 3 is a view illustrating a principle of an electric field stirring step.

From a pathological specimen to be prepared in a pathology department, important information related to a diagnosis, a prognosis, and selection of a medical treatment in a patient can be obtained. As a method for preparing a pathological specimen, an immunohistochemical staining method (IHC) of observing the expression level of a protein in a tissue or a cell or an in situ hybridization method (ISH) of observing the expression level of a gene in a tissue or a cell while observing the shape of the tissue or the cell as a tissue specimen, or the like is exemplified.

As shown in FIG. 1, a tissue specimen Ts to be used in the preparation of a pathological specimen is fixed to a substrate 1. As the substrate 1, a colorless and transparent microscope slide which is standardized in JIS R 3703:1998 and has a width of 26 mm, a length of 76 mm, and a thickness of 1.1 mm is used. On the substrate 1, in order to hold a solution such as a reagent to be supplied to the fixed tissue specimen Ts within a predetermined range, for example, a water-repellent ring 2 is formed. The tissue specimen Ts is, for example, a sliced tissue section and is fixed inside the water-repellent ring 2. The water-repellent ring 2 may be formed by applying a water repellent agent in a ring form to the substrate 1, or a ring-shaped sticker having water repellency may be adhered to the substrate 1. The water-repellent ring 2 may be formed so as to surround the tissue specimen Ts on the substrate 1 having the tissue specimen Ts fixed thereto. Incidentally, the shape of the water-repellent part is not limited to a circular shape, and may be a polygonal shape such as a quadrangular shape.

Further, in the substrate 1, a marking region 3 for discriminating the fixed tissue specimen Ts is provided on one end portion side in the longitudinal direction of the substrate 1. On the marking region 3, for example, a sticker on which the name, management number, or the like of the fixed tissue specimen Ts is written may be adhered, or a coating face on which the name, management number, or the like of the fixed tissue specimen Ts can be written may be formed.

The number of water-repellent rings 2 to be formed for the substrate 1 is not limited to one, and for example, two water-repellent rings 2 may be formed. A positive tissue specimen is fixed within one of the water-repellent rings 2, and a negative tissue specimen for comparison may be fixed within the other water-repellent ring 2. Hereinafter, the substrate 1 having the tissue specimen Ts fixed thereto is referred to as "substrate W".

In the method for preparing a pathological specimen such as IHC or ISH described above, examples of a common step include a washing step of applying a washing solution Cs to the substrate W and performing washing and a reaction step of applying a reagent Rs to the substrate W and allowing the tissue specimen Ts and the reagent Rs to react with each other as shown in FIG. 2. Examples of the reagent Rs include a primary antibody reagent and a secondary antibody reagent to be used in an antigen-antibody reaction step, and a color developing reagent to be used in a color development reaction step. The washing step is performed not only before such a reaction step, but also after the reaction step for removing the remaining excess reagent Rs. In the method for preparing a pathological specimen of this embodiment, in order to allow the preparation of a pathological specimen to efficiently proceed, an electric field stirring step of performing stirring by applying an electric field to a solution S such as the reagent Rs dropped onto the substrate W is adopted. The substrate W comes and goes to and from the washing step, the reaction step, and the electric field stirring step.

As will be described in detail later, in this embodiment, the preparation of a pathological specimen is performed using a pathological specimen preparation system including a pathological specimen preparation device. In the washing step, washing is performed by dropping a predetermined amount of the washing solution Cs onto the substrate W as a droplet from a nozzle 131. In the reaction step, a reaction is performed by dropping a predetermined amount of the reagent Rs onto the substrate W as a droplet from a cartridge 50 filled with the reagent Rs. In the electric field stirring step, the solution S is stirred by disposing the substrate W between a pair of electrodes 10 and 20 opposed to each other and generating an electric field between the pair of electrodes 10 and 20.

As shown in FIG. 3, in the electric field stirring step, the substrate W is mounted on the lower electrode 10 of the pair of electrodes 10 and 20 vertically opposed to each other. Between the lower electrode 10 and the upper electrode 20 opposed to each other with a predetermined gap therebetween, for example, a rectangular potential which changes between 0 kV and 4 kV is applied in a predetermined cycle so as to generate an electric field. By a Coulomb force generated with an increase in the potential, the solution S is drawn toward the upper electrode 20 side. The Coulomb force decreases with a decrease in the potential, and the solution S drawn toward the upper electrode 20 side falls by gravity. By repeating such deformation of the solution S, the solution S is stirred. Incidentally, in the pathological specimen preparation device, the lower electrode 10 on which the substrate W is mounted has a function as a stage on which the substrate W is mounted in the washing step and the reaction step, and therefore is referred to as "stage 10" in the following description.

In the above-mentioned step of preparing a pathological specimen, for example, the types of the washing solution Cs and the reagent Rs, and the conditions for the steps such as the conditions for the washing, the reaction, and the electric field stirring, etc. are set in advance and utilized as a pathological specimen preparation protocol.

<Pathological Specimen Preparation Device>

Next, an outline of a pathological specimen preparation device of this embodiment will be described with reference to FIG. 4. FIG. 4 is a schematic perspective view showing a configuration of the pathological specimen preparation device.

As shown in FIG. 4, a pathological specimen preparation device 100 of this embodiment includes four tanks 106, 107, 108, and 109, a stage portion 110, a washing portion 130, a reagent supply portion 150, an electric field stirring portion 170, a circuit unit 180, and a frame 105 that is a structure body in which these respective portions are disposed. The frame 105 has a substantially square first plate 101, a substantially square second plate 102, two rectangular third plates 103, and a plurality of support columns 104 for supporting these plates sequentially from the first plate 101 with a gap therebetween. The frame 105 is composed of, for example, aluminum.

When the pathological specimen preparation device 100 is used, the washing portion 130 comes to the near side with respect to an operator, and therefore, in the case where the washing portion 130 is placed on the near side, the right-left direction is referred to as "X direction", the front-rear direction is referred to as "Y direction", and the up-down direction is referred to as "Z direction", and a description will be given hereinbelow. Incidentally, in this embodiment, the Y direction corresponds to the first direction of the invention, and the X direction corresponds to the second direction crossing the first direction of the invention.

On the first plate 101 which is a lower stage of the frame 105, the four tanks 106, 108, 109, and 107 are disposed in this order side by side in the X direction on the front side of the Y direction. In the tank 106, a washing solution which is a buffer solution for preventing the tissue specimen Ts from drying or the like and for example, phosphate-buffered saline (PBS), Tris-buffered saline (TBS), standard saline citrate (SSC), or the like is stored. In the tank 107, pure water ($H_2O$) is stored as another washing solution. As the tanks 106 and 107, in consideration of chemical resistance, weight, or the like, for example, resin containers made of polyethylene, polypropylene, or the like are used. The tanks 106 and 107 are one example of the washing solution tank in the invention.

The tanks 108 and 109 disposed between the two tanks 106 and 107 are provided for storing the waste liquids of the washing solution Cs and the reagent Rs. The waste liquid of the washing solution Cs and the waste liquid of the reagent Rs may be discharged and stored in one tank, however, there is a reagent Rs containing a substance (color developing agent) having carcinogenicity such as the color developing reagent described above, and when it is mixed with other liquids, the amount of the waste liquid required to be subjected to a predetermined waste liquid treatment is increased. Therefore, in this embodiment, the device is configured to separately provide the tank 108 in which the waste liquid of the washing solution Cs and the waste liquid of the reagent Rs may be mixed and stored, and the tank 109 in which a waste liquid containing the color developing reagent is stored. As also the tanks 108 and 109, for example, resin containers made of polyethylene, polypropylene, or the like are used in the same manner as the tanks 106 and 107. The tanks 108 and 109 are one example of the waste liquid tank (a first waste liquid tank and a second waste liquid tank) in the invention. Incidentally, the number of tanks is not limited to four, and may be increased depending on the type or the like of the washing solution Cs to be used.

On the rear side in the Y direction in the first plate 101, the circuit unit 180 is disposed. The circuit unit 180 includes a power supply unit that supplies power to an electrical driving system included in the stage portion 110, the washing portion 130, the reagent supply portion 150, and the electric field stirring portion 170, a control unit associated with the control of the respective portions, and the like. The electrical configuration of the circuit unit 180 will be described in the below-mentioned pathological specimen preparation system.

On the second plate 102 positioned on the upper side in the Z direction of the first plate 101, the stage portion 110, two pumps for sending out and supplying the washing solution Cs from the tank 106 or the tank 107, and a flow path switching mechanism for switching a discharge flow path for sorting and discharging the waste liquid of the washing solution Cs or the reagent Rs to either the tank 108 or the tank 109 are disposed. The two pumps and the flow path switching mechanism will be described later.

The stage portion 110 includes the stage 10 on which the substrate W is mounted, a stage transport mechanism that moves the stage 10 in the Y direction, and a stage tilting mechanism that tilts the stage 10 in the X direction. On the second plate 102, a plurality of (in this embodiment, six) stage portions 110 extending in the Y direction are arranged in parallel in the X direction. The stage transport mechanism and the stage tilting mechanism will be described in detail later. Incidentally, the number of stage portions 110 is not limited to six.

The third plate 103 extending in the Y direction is supported by the support columns 104 at one end portion and the other end portion in the X direction and the Y direction so as to sandwich the plurality of (six) stage portions 110 arranged in parallel in the X direction.

The washing portion 130, the reagent supply portion 150, and the electric field stirring portion 170 extend over the two third plates 103 in the X direction and also are disposed on the third plates 103 in this order in the Y direction. The washing portion 130 has a plurality of (six) nozzles 131 corresponding to the number of stages 10, and is configured such that the washing solution Cs necessary for washing out of the two types of washing solutions Cs can be supplied to each of the plurality of (six) stages 10. The reagent supply portion 150 is configured such that the reagent Rs necessary for a reaction out of a plurality of types of reagents Rs can be supplied to each of the plurality of (six) stages 10. The electric field stirring portion 170 has the upper electrode 20 of the pair of electrodes 10 and 20 described above. The upper electrode 20 is disposed so as to extend in the X direction across the plurality of (six) stage portions 110.

Each stage portion 110 is configured such that the stage 10 is moved in the Y direction by the stage transport mechanism and is disposed corresponding to each of the washing portion 130, the reagent supply portion 150, and the electric field stirring portion 170.

According to such a pathological specimen preparation device 100, the preparation of a pathological specimen can be performed using the six substrates W at the maximum. Further, in the frame 105, the four tanks 106, 107, 108, and 109, the circuit unit 180, the stage portion 110, the washing portion 130, the reagent supply portion 150, and the electric field stirring portion 170 are disposed in a superimposed manner, and therefore, the pathological specimen preparation device 100 which has a small footprint (mounting area) and is small in size is realized. Hereinafter, the configurations and structures of the respective portions in the pathological specimen preparation device 100 will be described. Incidentally, the frame 105 capable of disposing the respective portions in a superimposed manner in this manner is not limited to the three-stage configuration having the first plate 101, the second plate 102, and the third plate 103, and may have a three- or more stage, for example, four-stage configuration.

<Stage Portion>

FIG. 5 is a schematic perspective view showing a configuration of the stage portion, FIG. 6 is a schematic perspective view showing the stage, FIG. 7 is a schematic perspective view showing a liquid discharge guide portion, and FIG. 8 and FIG. 9 are each a principal part perspective view illustrating the stage tilting mechanism.

As shown in FIG. 5, the stage portion 110 has the stage 10, a support frame 111, a motor 115, a linear guide 117, a first support portion 119, a second support portion 120, a liquid discharge guide portion 126, and the like.

As shown in FIG. 6, the stage 10 is a substantially rectangular parallelepiped body and is disposed so that the longitudinal direction is parallel to the Y direction. The stage 10 has an upper face 11 on which the substrate W is mounted, a notched portion 13 in which a part of the front right corner of the upper face 11 is notched, and an edge portion 14 provided along a long side portion on the left side of the upper face 11 and front and rear short side portions. The notched portion 13 is notched so that when the substrate W is set or reset with respect to the upper face 11 by grasping an end of the substrate W with forceps or the like, the forceps do not come into contact with the stage 10. That is, it is configured such that setting or resetting of the substrate W with respect to the stage 10 can be easily performed.

Further, the edge portion 14 has a tilted portion 14a which is tilted projecting to the outside from the long side portion on the left side of the edge portion 14. As will be described in detail later, the stage 10 is supported on the short side portion side by the second support portion 120 in a state of being rotatable in a given direction. Further, on a side face on the short side portion side of the stage 10, two screw holes 10b and 10c associated with the support of the stage 10 by the second support portion 120.

As shown in FIG. 5, the support frame 111 has an upper face portion 113 extending in the Y direction, a pair of leg portions 111a and 111b which support the upper face portion 113 at both ends in the Y direction, and a pair of bottom face portions 112a and 112b. The support frame 111 is configured such that the pair of leg portions 111a and 111b, the pair of bottom face portions 112a and 112b, and the upper face portion 113 are integrally formed by, for example, folding a SUS plate after performing contour machining. On a face on the lower side in the Z direction of the upper face portion 113, the linear guide 117 is provided so as to extend in the Y direction.

The motor 115 is, for example, a stepping motor, and is attached to the leg portion 111b positioned on the rear side in the Y direction of the pair of leg portions 111a and 111b so that a rotating shaft points upward in the Z direction. To the rotating shaft, a timing pulley 116b is attached. Another timing pulley 116a is pivotally supported in a rotatable manner on the lower front side in the Y direction of the upper face portion 113. A timing belt 118 is stretched over the two timing pulleys 116a and 116b. The first support portion 119 is fixed to a portion on the right side in the X direction of the stretched timing belt 118. When the motor 115 is driven, the timing belt 118 rotates, and the first support portion 119 fixed to the timing belt 118 can be moved to the front and rear sides in the Y direction.

The first support portion 119 has a T-shaped contour, and a quadratic prism-shaped support rod 121 extending in the Z direction is attached thereto. To the lower end of the support rod 121, a circular cylindrical rod 122 is attached in a rotatable manner through a miniature bearing. By forming the support rod 121 such that the upper end is larger than the other portion, the support rod 121 is incorporated in the first support portion 119 in a state where the support rod 121 can move only upward in the Z direction from the state where the upper end is caught by the first support portion 119 and the lower end protrudes downward from the first support portion 119.

Further, to the first support portion 119, a pair of guide portions 124 extending to the left side in the X direction is attached. The pair of guide portions 124 is attached to the first support portion 119 so as to sandwich the upper face portion 113 of the support frame 111 and the linear guide 117 in the Z direction. To the guide portion 124 on the lower side in the Z direction of the pair of guide portions 124, a slider 117a is attached. The slider 117a is fitted to the linear guide 117 so as to be movable in the Y direction along the linear guide 117. That is, when the motor 115 is driven, the first support portion 119 can be moved in the Y direction along the linear guide 117. The second support portion 120 is attached to the guide portion 124 on the upper side in the Z direction of the pair of guide portions 124.

The second support portion 120 has a side face portion 120a folded to the upper side in the Z direction on both end sides in the Y direction, and the stage 10 is sandwiched and supported along the Y direction between the side face portions 120a facing each other. Therefore, when the motor 115 is driven, the stage 10 can be moved in the Y direction along the linear guide 117 of the support frame 111.

That is, the stage transport mechanism of this embodiment includes at least the support frame 111, the motor 115, the two timing pulleys 116a and 116b, the linear guide 117, the slider 117a, the timing belt 118, the first support portion 119, the second support portion 120, and the pair of guide portions 124.

An L-shaped frame 114 is vertically provided at a corner on the rear side of the bottom face portion 112a on the front side in the Y direction of the pair of bottom face portions 112a and 112b of the support frame 111. In the L-shaped frame 114, an L-shaped long side portion 114b is disposed along the Y direction, and an upper end of the long side portion 114b is folded to the right side in the X direction, thereby forming an upper face portion 114a. Further, to the long side portion 114b, a substantially trapezoidal cam 125 is attached. Further, the cam 125 is attached at a position corresponding to the washing portion 130 in the pathological specimen preparation device 100 in the Y direction.

The liquid discharge guide portion 126 is provided on the left side in the X direction across the stretched timing belt 118 with respect to the cam 125. As shown in FIG. 7, the liquid discharge guide portion 126 is a gutter having a substantially pentagonal contour similar to a baseball home base when viewed from the X direction, and a flexible tube 127 is attached to the lower end thereof. Further, the liquid discharge guide portion 126 has a protruding portion 123 protruding to the right side in the X direction. The protruding portion 123 has a first protruding portion 123a extending to the right side in the X direction and a second protruding portion 123b tilted by about 60° with respect to the first protruding portion 123a. A gap 123c is provided between the first protruding portion 123a and the second protruding portion 123b.

As shown in FIG. 5, the first protruding portion 123a is attached to the upper face portion 113 of the support frame 111 on the upper side in the Z direction of the cam 125. That is, the liquid discharge guide portion 126 is attached at a position corresponding to the washing portion 130 in the pathological specimen preparation device 100 in the same manner as the cam 125. For example, even if the washing solution supplied from the washing portion 130 leaks in the first protruding portion 123a, the washing solution can be discharged from the gap 123c by the liquid discharge guide portion 126. The liquid discharge guide portion 126 forms a part of the discharge flow path that discharges the reagent or the washing solution flowing down from the substrate on the tilted stage of the invention toward the waste liquid tank.

To the leg portion 111a on the front side in the Y direction of the pair of leg portions 111a and 111b of the support frame 111, a microswitch 128 is attached. The microswitch 128 is provided at a position where it comes into contact with the first support portion 119 when the first support portion 119 moves to the front side in the Y direction by driving the motor 115. The microswitch 128 is provided for detecting the position of the first support portion 119, that is, the stage 10 that moves in the Y direction. When the microswitch 128 is brought into an on state by the contact of the first support portion 119 with the microswitch 128, the motor 115 is stopped. That is, the stage 10 is stopped on the front side in the Y direction. In this embodiment, the position where the first support portion 119 comes into contact with the microswitch 128 is the starting point of the movement of the stage 10, and the substrate W is set or reset with respect to the stopped stage 10 (see FIG. 2).

Next, the stage tilting mechanism of this embodiment will be described with reference to FIG. 8 to FIG. 9.

As shown in FIG. 8, the stage 10 is supported on the guide portion 124 of the first support portion 119 through the second support portion 120. In the side face portion 120a of the second support portion 120, a shaft portion 120b which pivotally supports the stage 10 in a rotatable manner is provided. On the side face on the short-side side of the stage 10, a locking portion 17 that locks a spring 18 on one side is provided, and on the inside of the side face portion 120a of the second support portion 120, a locking portion 120c that locks the spring 18 on the other side is provided. According to this, by the spring 18, the stage 10 is biased downward in the Z direction, and is in a state where the rotation is stopped by a stopper 124a vertically provided in the guide portion 124.

The cam 125 is attached to the long side portion 114b so that a bottom face 125a of the cam 125 faces the upper face portion 114a of the L-shaped frame 114. Further, the cam 125 has a substantially trapezoidal shape in which an inclined plane on the rear side in the Y direction has a smaller tilt angle than an inclined plane on the front side. The cam 125 is generally configured such that the front side in the Y direction is biased upward in the Z direction so that an end portion of the inclined plane on the rear side comes into contact with the upper face portion 114a of the L-shaped frame 114. That is, the cam 125 is in a state where a gap is formed between the end portion of the inclined plane on the front side and the upper face portion 114a. When the motor 115 is driven and the first support portion 119 moves to the rear side in the Y direction from the starting point, the rod 122 at the lower end of the support rod 121 penetrates in the gap and slips through between the upper face portion 114a and the cam 125. That is, in the movement of the stage 10 from the starting point to the rear side in the Y direction, the movement of the support rod 121 to the upper side in the Z direction does not occur.

On the other hand, as shown in FIG. 9, when the motor 115 is driven and the first support portion 119 moves to the starting point from the rear side in the Y direction, the rod 122 at the lower end of the support rod 121 is transported onto an inclined plane 125c on the rear side of the cam 125. In that case, the support rod 121 is positioned on the lower side of the stage 10, and therefore, an upper end 121a of the support rod 121 pushes up a bottom face 12 of the stage 10. On the other hand, the stage 10 is biased downward in the Z direction by the spring 18 as described above, and therefore, the support rod 121 coming into contact with the bottom face 12 of the stage 10 pushes down the cam 125. The bottom face 125a of the cam 125 is fixed in contact with the upper face portion 114a of the L-shaped frame 114. By the movement of the first support portion 119, the rod 122 rides on the upper face 125b from the inclined plane 125c on the rear side of the cam 125, whereby the support rod 121 pushes up the bottom face 12 of the stage 10 further upward in the Z direction. According to this, the stage 10 rotates to the left side in the X direction around the shaft portion 120b provided in the side face portion 120a of the second support portion 120. That is, the substrate W mounted on the upper face 11 of the stage 10 is tilted to the left side in the X direction. Incidentally, as shown in FIG. 8 and FIG. 9, in the guide portion 124 on the upper side of the pair of guide portions 124, the stopper 124a having a rod-like shape is provided as described above. When the bottom face 12 is in contact with a tip portion of the stopper 124a, in other words, when the bottom face 12 of the stage 10 is not pushed up by the support rod 121, the posture of the upper face 11 of the stage 10 is in a horizontal state. The stopper 124a adjusts the horizontal state of the stage 10, and therefore is fixed in a state where the length when the stopper 124a is attached to the guide portion 124 can be adjusted.

That is, the stage tilting mechanism of this embodiment includes at least the L-shaped frame 114, the support rod 121, the cam 125, and the second support portion 120, and these are an example of the support mechanism according to the invention. Since a dedicated driving portion, for example, a motor, a piston, or the like for tilting the stage 10 is not included, the stage 10 can be tilted with a simple configuration.

FIG. 10 is a view showing a positional relationship between the tilted stage and the other configuration. More specifically, FIG. 10 is a view when viewing the tilted stage 10 from the Y direction.

In this embodiment, by the above-mentioned stage tilting mechanism, the upper face 11 of the stage 10 is tilted to the left side in the X direction from the horizontal state. When the stage 10 is tilted, the tilted portion 14a of the edge portion 14 of the stage 10 is configured to stop with a small gap between the tilted portion 14a and the second protruding portion 123b in the liquid discharge guide portion 126. The tilt angle θ of the upper face 11 of the stage 10 is preferably 60° or more from the viewpoint of easily and reliably discharging the reagent Rs or the washing solution Cs supplied to the substrate W from the top of the substrate W. Further, the relative position of the nozzle 131 to the stage 10 is adjusted so that when the stage 10 is tilted, the washing solution Cs ejected from the nozzle 131 of the washing portion 130 falls on the water-repellent ring 2 on the substrate W. In the washing portion 130, the substrate W mounted on the upper face 11 of the stage 10 is tilted by 60° from the horizontal state, and therefore, the reagent Rs or the washing solution Cs supplied to the substrate W is discharged from the substrate W through the liquid discharge guide portion 126.

Further, when the length in the Y direction of the stage 10 is denoted by L1 as shown in FIG. 6, the length in the Y direction of the first protruding portion 123a of the liquid discharge guide portion 126 is denoted by L2 as shown in FIG. 7, and the length in the Y direction of the upper face 125b of the cam 125 is denoted by L3 as shown in FIG. 9, L1, L2, and L3 satisfy the following numerical formula (1).

$$L2 \geq L1 + L3 \tag{1}$$

According to the stage tilting mechanism of this embodiment, the stage 10 can be moved in the Y direction within the range of the length of L3 in a state where the rod 122 at the lower end of the support rod 121 rides on the upper face 125b of the cam 125, and the upper end 121a of the support rod 121 pushes up the bottom face 12 so as to tilt the stage 10. The device is configured such that at this time, the reagent Rs or the washing solution Cs supplied to the substrate W is reliably discharged to the liquid discharge guide portion 126. The number of tissue specimens Ts disposed on the substrate W is not limited to one as shown in FIG. 1, and a plurality of tissue specimens Ts are disposed. Further, also the size of the tissue specimen Ts is not always uniform. That is, the respective portions are configured such that the reagent Rs or the washing solution Cs supplied can be reliably discharged in accordance with the state of the tissue specimen Ts disposed on the substrate W.

Incidentally, the tilt angle θ of the stage 10 is determined by to what extent the bottom face 12 of the stage 10 is pushed up by the support rod 121. In this embodiment, as shown in FIG. 9, the tilt angle θ can be adjusted by adjusting the height h from the upper face portion 114*a* of the L-shaped frame 114 to the upper face 125*b* of the cam 125 when the rod 122 provided at the lower end of the support rod 121 rides on the upper face 125*b* of the cam 125.

<Washing Portion>

Next, the washing portion 130 of this embodiment will be described with reference to FIG. 11 and FIG. 12. FIG. 11 is a schematic perspective view showing a configuration of the washing portion, and FIG. 12 is a schematic perspective view showing a configuration of the flow path switching mechanism.

As shown in FIG. 11, the washing portion 130 has a plurality of (six) T-shaped nozzles 131, a valve group 132 and a valve group 133 each including a plurality of valves that are paired up with each other, two valves 134 and 135 for switching the washing solution, and a support plate 136 that supports the plurality of nozzles 131.

The support plate 136 has a rectangular shape and is supported by the support columns so as to extend across the two third plates 103 of the pathological specimen preparation device 100 such that the long side direction is parallel to the X direction as described above (see FIG. 4). In the support plate 136, a plurality of (six) holes 136*a*, 136*b*, 136*c*, 136*d*, 136*e*, and 136*f* are provided at equal intervals in the X direction. These holes 136*a*, 136*b*, 136*c*, 136*d*, 136*e*, and 136*f* are provided in accordance with the number and the positions of the stage portions 110 (stages 10) arranged in the X direction. In these holes 136*a*, 136*b*, 136*c*, 136*d*, 136*e*, and 136*f*, the T-shaped nozzles 131 are inserted, respectively, and therefore, the plurality of nozzles 131 are also given reference numerals from the left side in the X direction and called nozzles 131*a*, 131*b*, 131*c*, 131*d*, 131*e*, and 131*f*.

The valve group 132 and the valve group 133 also include a plurality of valves provided in accordance with the number of nozzles 131. The valve group 132 has a plurality of (six) valves 132*a*, 132*b*, 132*c*, 132*d*, 132*e*, and 132*f* arranged in the Y direction. The valve group 133 also has a plurality of (six) valves 133*a*, 133*b*, 133*c*, 133*d*, 133*e*, and 133*f* arranged in the Y direction. The valve group 132 and the valve group 133 are disposed separately on the two third plates 130 of the pathological specimen preparation device 100 so as to face each other with the support plate 136 interposed therebetween (see FIG. 4).

The valve group 132 and the valve group 133, and the valves 134 and 135 are electromagnetic valves whose opening and closing can be electrically controlled, and the opening and closing are controlled by a control unit included in the circuit unit 180. More specifically, by pushing a rod from the lower side in the Z direction in an opening/closing portion which is provided on the upper side in the Z direction and in which a through-hole is provided, and pressing and squashing a flexible tube inserted into the through-hole with the rod, a liquid flow path in the tube can be closed. When the pressing of the tube is released by lowering the rod, the liquid flow path in the tube can be opened.

For example, as shown by the broken line in FIG. 11, a flexible tube is connected to one end of the nozzle 131*a* through the valve 132*a*. Similarly, a flexible tube is connected to the other end of the nozzle 131*a* through the valve 133*a*. The connection of a tube to another nozzle 131 through another valve is also performed in the same manner. In the valve 134 on one side of the two valves 134 and 135 for switching the washing solution, a tube passing through the valve group 132 is inserted, and in the valve 135 on the other side, a tube passing through the valve group 133 is inserted. The two valves 134 and 135 for switching the washing solution are connected to different washing solution tanks through a pump. According to this, two types of washing solutions can be ejected from each of the plurality of nozzles 131*a*, 131*b*, 131*c*, 131*d*, 131*e*, and 131*f*. A detailed method of supplying the washing solution will be described later.

Incidentally, in the support plate 136 of the washing portion 130, a barcode reader 162 is attached to a place where the barcode reader 162 does not interfere with the placement of the plurality of nozzles 131*a*, 131*b*, 131*c*, 131*d*, 131*e*, and 131*f*. This barcode reader 162 is associated with the reagent supply portion 150 and will be described in detail later.

As shown in FIG. 12, the flow path switching mechanism 140 of this embodiment has a first discharge flow path 141 having a first discharge port 141*a*, a second discharge flow path 142 having a second discharge port 142*a*, a rotating shaft 143, and a motor 144.

The first discharge flow path 141 and the second discharge flow path 142 are each a gutter having a substantially pentagonal contour, and are disposed such that the second discharge flow path 142 is superimposed on the first discharge flow path 141 in a state where the long side portions are both parallel to the X direction and also are shifted from each other in the Y direction. In this manner, by superimposing the first discharge flow path 141 and the second discharge flow path 142, the first discharge port 141*a* and the second discharge port 142*a* are also disposed at positions shifted from each other in the X direction and the Y direction. More specifically, in the pathological specimen preparation device 100, the first discharge port 141*a* is positioned on the upper side in the Z direction of the tank 108, and the second discharge port 142*a* is positioned on the upper side in the Z direction of the tank 109.

The rotating shaft 143 is disposed so as to extend in the X direction along the borderline between the superimposed first discharge flow path 141 and the second discharge flow path 142. One end of the rotating shaft 143 is pivotally supported in a rotatable manner, and the other end is connected to the motor 144.

In the rotating shaft 143, a plurality of (six) holes 143*a*, 143*b*, 143*c*, 143*d*, 143*e*, and 143*f* are provided at equal intervals in the X direction. These holes 143*a*, 143*b*, 143*c*, 143*d*, 143*e*, and 143*f* are provided in accordance with the number and the positions of the stage portions 110 arranged in the X direction. More specifically, the flexible tube 127 connected to the liquid discharge guide portion 126 of the leftmost stage portion 110 of the plurality of stage portions 110 arranged in the X direction is inserted through the hole 143*a* so as to protrude downward from the rotating shaft 143. When this tube 127 is denoted by "tube 127*a*", the tubes 127*b*, 127*c*, 127*d*, 127*e*, and 127*f* in the other stage portions 110 are also inserted into the corresponding holes 143b, 143c, 143d, 143e, and 143f similarly.

By rotating the motor 144 within a predetermined shaft angle range, the positions of the tips of the tubes 127a, 127b, 127c, 127d, 127e, and 127f protruding downward from the rotating shaft 143 are apportioned to the first discharge flow path 141 side and the second discharge flow path 142 side in the Y direction. That is, the flow path of a liquid that moves along the tubes 127a, 127b, 127c, 127d, 127e, and 127f and is discharged can be switched to the first discharge flow path 141 and the second discharge flow path 142. Such a flow path switching mechanism 140 is disposed on the second plate 102 of the frame 105 (see FIG. 4).

Next, a specific way of supplying and discharging the washing solution will be described with reference to FIG. 13 to FIG. 15. FIG. 13 to FIG. 15 are each a schematic view showing a way of supplying the washing solution. More specifically, FIG. 13 shows a way of supplying the washing solution other than pure water, FIG. 14 shows a way of supplying pure water, and FIG. 15 shows a method of washing the supply flow path of the washing solution with pure water. Incidentally, in FIG. 13 to FIG. 15, since the pumps P1 and P2 and the tanks 106 and 107 for the washing solutions are shown, the arrangement of the nozzles 131a, 131b, 131c, 131d, 131e, and 131f is in the opposite direction to the actual arrangement in the washing portion 130. Further, the same also applies to the arrangement of the valve groups 132 and 133 associated with the nozzles 131a, 131b, 131c, 131d, 131e, and 131f.

As shown in FIG. 13, a tube 138 passing through the valve group 132 is connected to one end of each of the T-shaped nozzles 131a, 131b, 131c, 131d, 131e, and 131f, and a tube 137 passing through the valve group 133 is connected to the other end. The tube 137 is connected to the pump P1 through the valve 135 for switching the washing solution. The tube 138 is connected to the pump P2 and is also connected to the tube 137 through the valve 134 for switching the washing solution. In the tank 106, the washing solution other than pure water is stored, and it is sent to the tube 137 by the pump P1. In the tank 107, pure water is stored, and it is sent to the tube 138 by the pump P2. The pumps P1 and P2 may adopt, for example, a system that sucks and sends the washing solution such as a rotary pump, or a system such as a compressor that pumps the washing solution by pressurizing the tanks 106 and 107.

When all the valves 132a, 132b, 132c, 132d, 132e, and 132f of the valve group 132 and the valve 134 are closed, and all the valves 133a, 133b, 133c, 133d, 133e, and 133f of the valve group 133 and the valve 135 are opened, and the pump P1 is operated, the washing solution stored in the tank 106 can be supplied from all the nozzles 131a, 131b, 131c, 131d, 131e, and 131f.

As shown in FIG. 14, when all the valves 132a, 132b, 132c, 132d, 132e, and 132f of the valve group 132 are opened, and all the valves 133a, 133b, 133c, 133d, 133e, and 133f of the valve group 133, and the valve 134 and the valve 135 are closed, and the pump P2 is operated, pure water stored in the tank 107 can be supplied from all the nozzles 131a, 131b, 131c, 131d, 131e, and 131f.

Further, as shown in FIG. 15, when all the valves 132a, 132b, 132c, 132d, 132e, and 132f of the valve group 132 and the valve 134 are opened, and also all the valves 133a, 133b, 133c, 133d, 133e, and 133f of the valve group 133 are opened, and the valve 135 is closed, and the pump P2 is operated, pure water stored in the tank 107 can be supplied from all the nozzles 131a, 131b, 131c, 131d, 131e, and 131f through the tube 137 and the tube 138. In other words, the supply flow path of the washing solution associated with all the nozzles 131a, 131b, 131c, 131d, 131e, and 131f can be washed with pure water.

Further, in FIG. 13, the washing solution supplied from all the nozzles 131a, 131b, 131c, 131d, 131e, and 131f is supplied to the substrate W positioned in the washing portion 130 in the pathological specimen preparation device 100. In the case where the substrate W is not mounted on all the stages 10 of the plurality of stage portions 110, when as many substrates W as prepared are mounted sequentially from the left side in the X direction, the washing solution can be supplied to the respective substrates W by opening and closing the valves corresponding to the stage portions 110 on which the substrates W are mounted. Further, when the stage 10 is moved to the starting point from the rear side in the Y direction and disposed at a position corresponding to the washing portion 130 by driving the motor 115 of the stage portion 110, the stage 10 can be tilted by the stage tilting mechanism, and therefore, the reagent Rs dropped onto the substrate W mounted on the stage 10 or the washing solution Cs supplied thereto can be discharged through the liquid discharge guide portion 126. Further, in the case where a carcinogenetic substance is contained in the reagent Rs, by driving the motor 144 of the flow path switching mechanism 140, the washing solution Cs containing the reagent Rs is allowed to flow through the second discharge flow path 142 and can be stored in the tank 109. In the case where a carcinogenetic substance is not contained in the reagent Rs, by driving the motor 144 of the flow path switching mechanism 140, the washing solution Cs containing the reagent Rs is allowed to flow through the first discharge flow path 141 and can be stored in the tank 108.

<Reagent Supply Portion>

Next, the reagent supply portion 150 will be described with reference to FIG. 16 to FIG. 18. FIG. 16 is a schematic perspective view showing a configuration of the reagent supply portion, FIG. 17 is a perspective view showing the cartridge, and FIG. 18 is a schematic plan view for illustrating the movement of the reagent supply portion.

As shown in FIG. 16, the reagent supply portion 150 is a device that supplies the reagent Rs filled in the cartridge 50 to the substrate W mounted on the stage 10 of the stage portion 110. The reagent supply portion 150 has a support frame 151, a plurality of cartridge holders 155 as holding portions capable of attaching and detaching the cartridge 50, a timing belt 156, a pair of timing pulleys 154a and 154b, a motor 157, and an electric pusher 158.

The support frame 151 is a structure body that supports the pair of timing pulleys 154a and 154b, the motor 157, and the electric pusher 158, and has a pier portion 152 that is vertically provided so as to extend in the X direction across the two third plates 103 of the pathological specimen preparation device 100, and an upper face portion 153 opposed to the pier portion 152 in the Z direction. Between the pier portion 152 and the upper face portion 153, the pair of timing pulleys 154a and 154b are provided on both end sides in the X direction. On the upper face portion 153, the motor 157 is disposed. The timing pulley 154a on one side (on the right side in the X direction) of the pair of timing pulleys 154a and 154b is pivotally supported in a rotatable manner between the pier portion 152 and the upper face portion 153. The timing pulley 154b on the other side (on the left side in the X direction) is connected to the motor 157, and the rotation thereof is electrically controlled. The motor 157 is, for example, a stepping motor.

The timing belt 156 is stretched between the pair of timing pulleys 154a and 154b. To the timing belt 156, a plurality of (nine) cartridge holders 155 are attached. In this embodiment, two cartridges 50 can be attached to and detached from one cartridge holder 155, and therefore, it is configured such that a total of 18 cartridges 50 can be attached to the plurality of (nine) cartridge holders 155. By driving the motor 157, the plurality of (nine) cartridge holders 155 attached to the timing belt 156 can be moved freely in the X direction. In this embodiment, a configuration including the pair of timing pulleys 154a and 154b, the timing belt 156, and the motor 157 is an example of the transport portion of the invention.

The upper face portion 153 is attached to the pier portion 152 so as to project to the rear side in the Y direction. In a part of the upper face portion 153 projecting from the pier portion 152, a plurality of (six) electric pushers 158 are provided. The electric pusher 158 includes a motor 158a, a male screw 158b, and a support column 158c for the male screw 158b. The motor 158a is, for example, a linear stepping motor, and screws with the male screw 158b and allows the male screw 158b to move up and down in the Z direction. According to this, the electric pusher 158 can pressurize the cartridge 50 attached to the cartridge holder 155 from the upper side to the lower side in the Z direction.

To the timing belt 156, not only the cartridge holder 155, but also a CCD 161 as an image capture portion in the invention is attached through a support member.

Here, the cartridge 50 capable of ejecting the reagent Rs will be described with reference to FIG. 17. As shown in FIG. 17, the cartridge 50 has a first case 51 filled with the reagent Rs, a second case 52 having a cylindrical shape provided with a nozzle portion 52a on the bottom face, and a lid portion 53 of the first case 51. On the side closer to a housing port on a side face of the second case 52, a rectangular opening portion 52b is provided. Further, on the side closer to a bottom portion of the side face on which the opening portion 52b is provided, a locking portion 52c is provided. Also on a side face of the first case 51, a locking portion 51b is provided.

The first case 51 has a housing portion 51a capable of storing the reagent Rs, and a communication portion communicating with the housing portion 51a and capable of being connected to the nozzle portion 52a of the second case 52. A predetermined amount of the reagent Rs is injected into the housing portion 51a from the housing port of the first case 51, and the first case 51 is covered with the lid portion 53. Thereafter, when the first case 51 is inserted and pushed in the second case 52 from the housing port, the locking portion 51b of the first case 51 is locked in the opening portion 52b of the second case 52, whereby the first case 51 is fitted in the second case 52. According to this, it is configured such that water or the like hardly penetrates in the cartridge 50 from the outside.

It is configured such that when the lid portion 53 is pressed so as to push down the first case 51 with respect to the second case 52 after the reagent Rs is injected into the first case 51 and the cartridge 50 is brought into an airtight state, a predetermined amount of the reagent Rs can be ejected from the nozzle portion 52a through the communication portion.

As shown in FIG. 16, in the cartridge holder 155, quadrangular holes 155a and 155b are provided, and as shown in FIG. 17, on the side face of the second case 52 of the cartridge 50, the locking portion 52c is provided. Therefore, by inserting the cartridge 50 into the cartridge holder 155, either one of the two holes 155a and 155b and the locking portion 52c are locked to each other, and therefore, the second case 52 can be fixed so as not to move by attaching the cartridge 50 to the cartridge holder 155.

As shown in FIG. 18, by driving the motor 157 and moving the timing belt 156 in the X direction, the cartridge 50 attached to the cartridge holder 155 can be moved to a position overlapped with the electric pusher 158. By the electric pusher 158, the lid portion 53 of the cartridge 50 is pressed, and the reagent Rs is ejected from the nozzle portion 52a of the cartridge 50 as described above. At this time, by moving the stage 10 to a position opposed to the reagent supply portion 150 by the stage portion 110 in advance, a predetermined amount of the reagent Rs can be accurately dropped onto the tissue specimen Ts on the substrate W mounted on the stage 10.

As described above, to the timing belt 156, the CCD 161 as the image capture portion is attached. Therefore, by driving the motor 157, the CCD 161 can be moved freely in the X direction. Accordingly, in the plurality of stage portions 110 arranged in the X direction, an image of the substrate W mounted on each of the stages 10 can be captured by the CCD 161. By capturing the image of the substrate W by the CCD 161, the state of the tissue specimen Ts fixed to the substrate W, or the information related to the tissue specimen Ts written in the marking region 3 can be obtained as the image.

Further, when the cartridge holder 155 is moved by driving the motor 157, the cartridge 50 can be opposed to the barcode reader 162 attached to the support plate 136 of the washing portion 130 described above. By giving a barcode associated with the information of the housed reagent Rs to the side face of the cartridge 50 opposed to the barcode reader 162, the barcode can be read by the barcode reader 162. Incidentally, the barcode to be given to the cartridge 50 is a one-dimensional barcode or a two-dimensional barcode, and as the barcode reader 162, a device which can read these barcodes is selected.

<Electric Field Stirring Portion>

Next, the electric field stirring portion 170 will be described with reference to FIG. 19 and FIG. 20. FIG. 19 is a schematic perspective view showing a configuration of the electric field stirring portion, and FIG. 20 is a schematic cross-sectional view showing the shape of an electrode of the electric field stirring portion.

As shown in FIG. 19, the electric field stirring portion 170 has an upper electrode 20 and a support frame 171. The upper electrode 20 has a rectangular shape in which one side portion is longer than the other side portion. The support frame 171 is provided for stretching the long and narrow upper electrode 20 over the two third plates 103 of the pathological specimen preparation device 100 (see FIG. 4). The support frame 171 has a pair of leg portions 172a and 172b opposed to each other with a gap therebetween in the X direction and a pair of guide portions 173a and 173b fixed to the pair of leg portions 172a and 172b and opposed to each other with a gap therebetween in the Y direction. Each of the guide portions 173a and 173b of the pair is configured to have a groove capable of inserting the upper electrode 20 therein from the right side in the X direction. On the left ends of the pair of guide portions 173a and 173b, a support plate 174 is stretched over in the Y direction, and on the support plate 174, a microswitch 175 is provided. The microswitch 175 is provided for detecting whether the left end in the X direction of the upper electrode 20 is disposed at a predetermined position when the upper electrode 20 is inserted along the pair of guide portions 173a and 173b. That is, the plate-shaped upper electrode 20 can be attached at a predetermined position and also can be inserted and removed with respect to the support frame 171.

As shown in FIG. 20, on a face opposed to the stage 10 (that is, the lower electrode 10) of the upper electrode 20, a groove 21 is provided. The groove 21 is formed so as to extend in the short side direction of the upper electrode 20, that is, in the Y direction when the upper electrode 20 is set in the support frame 171 and cross the upper electrode 20. When an electric field is generated between the stage 10 and the upper electrode 20, and a Coulomb force is allowed to act on the solution S given to the substrate W, the solution S is deformed and stirred. In this embodiment, an interelectrode distance d between the stage 10 and the upper electrode 20 is constant. In other words, the interelectrode distance d cannot be made variable. When the solution S deformed during electric field stirring comes into contact with the upper electrode 20, an electrical short circuit occurs between the stage 10 and the upper electrode 20, and electric field stirring may be stopped. By forming such a groove 21 in the upper electrode 20, the solution S and the upper electrode 20 can be prevented from coming into contact with each other during electric field stirring. Further, the direction of the Coulomb force acting on the solution S becomes a direction toward the edge portion of the groove 21 and changes as compared with the case where the groove 21 is not provided, and therefore, the solution S can be more effectively stirred. Therefore, it is necessary to reliably determine the position in the X direction of the upper electrode 20 so that the groove 21 formed in the upper electrode 20 is opposed to the central portion in the X direction of the stage 10 on which the substrate W having the solution S formed thereon is mounted. Due to this, it is important to detect the position of the upper electrode 20 by the above-mentioned microswitch 175. In this embodiment, it is configured such that unless the upper electrode 20 comes into contact with the microswitch 175 and is brought into an on state, an electric field is not generated between the stage 10 and the upper electrode 20.

<Exterior Cover>

Next, the exterior cover of the pathological specimen preparation device 100 will be described with reference to FIG. 21. FIG. 21 is a schematic perspective view showing the exterior cover of the pathological specimen preparation device.

As shown in FIG. 21, an exterior cover 190 of the pathological specimen preparation device 100 is configured to be able to protect the pathological specimen preparation device 100 by separating the device from the surrounding environment. However, the four tanks 106, 107, 108, and 109 and the circuit unit 180 disposed on the first plate 101 as the lower stage in the frame 105 are not covered and are in a state of being exposed to the surroundings. That is, the four tanks 106, 107, 108, and 109 are put into a state of being able to be set or reset, and the circuit unit 180 having a heat generation source such as a power supply unit is put into a state of being able to dissipate heat to the surroundings.

More specifically, the exterior cover 190 has a front face plate 191 that covers a middle front face portion of the pathological specimen preparation device 100, a side face plate 192 that covers the side face in the X direction, a middle face plate 193 that covers a middle portion in the Z direction, and an upper face plate 194 that covers an upper portion in the Z direction. Further, the exterior cover 190 has a first opening and closing portion 195 that openably and closably covers a step portion between the front face plate 191 and the middle face plate 193, and a second opening and closing portion 196 that openably and closably covers a step portion between the middle face plate 193 and the upper face plate 194. Further, the exterior cover 190 has a side face plate 197 that is configured to be openable and closable so that the upper electrode 20 can be set or reset in the electric field stirring portion 170 of the pathological specimen preparation device 100, and a rear plate (illustration is omitted in FIG. 21) that covers a rear portion in the Y direction of the pathological specimen preparation device 100.

The front face plate 191 has a width capable of covering a portion from the second plate 102 to the third plate 103 of the frame 105. By opening the first opening and closing portion 195, the substrate W can be set or reset on the stage 10 of the stage portion 110. Further, by opening the second opening and closing portion 196, the cartridge 50 can be set or reset in the reagent supply portion 150.

As a member to be used for the exterior cover 190, for example, a resin plate of transparent polyethylene terephthalate (PET) or the like can be exemplified. Further, in order to prevent the radiation of an unnecessary electromagnetic wave to the outside from the electric field stirring portion 170, the circuit unit 180, or the like, it is preferred to provide an electromagnetic shield that can shield an electromagnetic wave on the resin plate.

<Pathological Specimen Preparation System>

Next, an outline of a pathological specimen preparation system of this embodiment will be described with reference to FIG. 22. FIG. 22 is a block diagram showing an electrical and mechanical configuration of the pathological specimen preparation system.

As shown in FIG. 22, a pathological specimen preparation system 1000 of this embodiment includes the pathological specimen preparation device 100, for example, a desktop computer 500, and peripheral devices connected to the computer 500.

The pathological specimen preparation device 100 has the stage portion 110, the washing portion 130, the reagent supply portion 150, and the electric field stirring portion 170 as described above. Further, the pathological specimen preparation device 100 includes a motor driver 181, a high voltage generation unit 182, an I/O 183, a Peltier controller 184, a control unit 185, a DC power supply unit 186, a USB hub 187, the CCD 161 as the image capture portion, and the barcode reader 162.

The motor driver 181 is a circuit board on which a circuit that drives and controls a motor included in each of the stage portion 110, the washing portion 130, and the reagent supply portion 150 is mounted. The high voltage generation unit 182 is a device that generates a potential which periodically changes as described above and applies the potential to the pair of electrodes 10 and 20 of the electric field stirring portion 170. To the stage 10 of the stage portion 110, a Peltier element 15 as a heating element for heating the stage 10 and a temperature sensor 16 that detects the temperature of the stage 10 are attached. The Peltier controller 184 is connected to the control unit 185 through the USB hub 187. The temperature sensor 16 is connected to the control unit 185 through the I/O 183. The Peltier controller 184 controls the temperature of the Peltier element 15 by controlling an electric current flowing in the Peltier element 15 based on a control signal from the control unit 185. Incidentally, the Peltier controller 184 of this embodiment includes a microcomputer associated with the control of the temperature of the Peltier element 15, however, the microcomputer may be configured to be included in the control unit 185.

The CCD 161 and the barcode reader 162 are connected to the control unit 185 through the USB hub 187. The CCD 161 is provided so as to be able to capture an image of the substrate W mounted on the stage 10 as described above. The control unit 185 can obtain the information of the tissue specimen Ts fixed to the substrate W from the information of the image of the substrate W captured by the CCD 161.

The barcode reader 162 is provided so as to be able to read a barcode given to the cartridge 50 mounted on the reagent supply portion 150 as described above. The control unit 185 can obtain the information of the reagent Rs filled in the cartridge 50 from the barcode read by the barcode reader 162.

The circuit unit 180 includes at least the motor driver 181, the high voltage generation unit 182, the I/O 183, the Peltier controller 184, the control unit 185, the DC power supply unit 186, and the USB hub 187. The DC power supply unit 186 generates a DC voltage required as a power supply for the respective portions of the circuit unit 180 from an AC power supply of 100 V supplied from the outside, and supplies the DC voltage.

Further, the control unit 185 is connected to the computer 500 through the USB hub 187 and a USB terminal. The computer 500 has a main body 501 including a CPU 502, a memory 503 as a memory portion, and terminals (HDMI (registered trademark), LAN, and USB) for achieving connection to various types of peripheral devices. To a USB terminal, a mouse 504 or a keyboard 505 associated with an input operation to the computer 500 is connected. Further, to another USB terminal, another barcode reader 506 different from the barcode reader 162 included in the pathological specimen preparation device 100, or a label printer 507 is connected. To an HDMI terminal, a monitor 508 is connected. The monitor 508 may be a display device that displays various types of information sent from the computer 500 or may function as both a display device and an input device. To a LAN terminal, for example, a network associated with the information management of the pathology department is connected.

The barcode reader 506 is mainly used for reading a barcode given to a reagent container such as a bottle in which the reagent Rs is housed. The computer 500 obtains the information of the reagent Rs from the barcode read and can print a barcode label to be adhered to the cartridge 50 filled with the reagent Rs using the label printer 507.

In the memory 503 of the computer 500, various types of pathological specimen preparation protocols associated with the above-mentioned method for preparing a pathological specimen are stored. The memory 503 in which the pathological specimen preparation protocols are stored may be an internal storage device such as a ROM, a RAM, or an HDD, or an external storage device to be used by being connected to a USB terminal.

An operator designates the pathological specimen preparation protocol stored in the computer 500, and drives and controls the pathological specimen preparation device 100 by the computer 500, and thus can prepare a pathological specimen. Further, by actually reading the barcode of the cartridge 50 attached to the reagent supply portion 150 with the barcode reader 162, the computer 500 can collate the information of the reagent Rs filled in the cartridge 50 with the information of the reagent Rs in the designated pathological specimen preparation protocol. According to this, management as to whether or not the reagent Rs to be used in the preparation of the pathological specimen is properly applied can be ensured.

Further, the computer 500 obtains an image of the substrate W captured by the CCD 161 and can perform an operation of associating the image with the designated pathological specimen preparation protocol. According to this, the traceability of the pathological specimen prepared according to the designated pathological specimen preparation protocol can be established. That is, the traceability of the pathological specimen can be improved as compared with the visual confirmation by an operator.

Further, by connecting the computer 500 to the network of the pathology department, a series of information related to the preparation of the pathological specimen can be shared and managed. Incidentally, the configuration of the pathological specimen preparation system 1000 is not limited thereto, and the system may include, for example, another device to be used for a pathological diagnosis such as a device that performs an image analysis of a stained state of a tissue or a cell. Further, the system preferably includes an uninterruptible power supply (UPS) capable of coping with a power failure.

Next, the effects of Examples will be specifically described by showing Examples of preparation of various types of pathological specimens using the pathological specimen preparation system 1000 including the pathological specimen preparation device 100, and Comparative Examples in which the pathological specimen preparation system 1000 is not used.

<Immunohistochemical Staining (IHC) Using Frozen Section in Example 1 and Comparative Example 1>

FIG. 23 is a table showing a step of preparing a pathological specimen by immunohistochemical staining of Example 1, and FIG. 24 is a table showing a step of preparing a pathological specimen in immunohistochemical staining of Comparative Example 1.

Example 1

As shown in FIG. 23, a step of preparing a pathological specimen by IHC of Example 1 has a first step of fixing a sliced tissue specimen Ts to the substrate W, a second step of washing the fixed tissue specimen Ts, a third step of removing endogenous PO (peroxidase) of the tissue specimen Ts, a fourth step of washing the tissue specimen Ts from which endogenous PO is removed, a fifth step of performing a primary antibody reaction, a sixth step of washing the tissue specimen Ts subjected to the primary antibody reaction treatment, a seventh step of performing a secondary antibody reaction, an eighth step of washing the tissue specimen Ts subjected to the secondary antibody reaction treatment, a ninth step of allowing the washed tissue specimen Ts to develop a color, a tenth step of washing the tissue specimen Ts allowed to develop a color, an eleventh step of subjecting the washed tissue specimen Ts to nuclear staining, a twelfth step of washing the tissue specimen Ts subjected to nuclear staining, a thirteenth step of encapsulating the washed tissue specimen Ts, and a fourteenth step of digitizing the depth of staining by performing an image analysis of the encapsulated tissue specimen Ts. These steps are stored in the memory 503 of the computer 500 as the pathological specimen preparation protocol on the premise that the pathological specimen preparation system 1000 is used. The computer 500 sends a control signal according to the pathological specimen preparation protocol to the control unit 185 of the pathological specimen preparation device 100 in the respective steps from the second step to the twelfth step, and the control unit 185 drives and controls the pathological specimen preparation device 100 so as to perform the treatments in the second step to the twelfth step.

In the first step of Example 1, as the tissue specimen Ts, a frozen section obtained by slicing a pig liver block is disposed inside the water-repellent ring 2 of the substrate 1, and thereafter the substrate 1 is immersed in acetone for 2 minutes. By doing this, the frozen section is adhered and fixed to the substrate 1. That is, the substrate W having the tissue specimen Ts fixed thereto is obtained. Then, the process proceeds to the second step.

In the second step of Example 1, the substrate W is mounted on the stage 10 of the pathological specimen preparation device 100. The control unit 185 drives and controls the stage transport mechanism (motor 115) so as to transport the stage 10 from the starting point to the washing portion 130 again after once passing through the washing portion 130. In the washing portion 130, the control unit 185 drives and controls the pump P1 and the associated valves so as to eject the washing solution Cs stored in the tank 106 from the nozzle 131 and allowing the washing solution Cs to continuously flow for 30 seconds. As the washing solution Cs, PBS-T (PBS containing Tween 20 which is a nonionic surfactant having a blocking action) is used. In the washing portion 130, washing is performed by supplying PBS-T to the substrate W in a state where the stage 10 is tilted by the stage tilting mechanism. PBS-T used for washing goes through the liquid discharge guide portion 126 from the tilted substrate W, and is guided to the first discharge flow path 141 by the flow path switching mechanism 140 and discharged and stored in the tank 108. Then, the process proceeds to the third step.

In the third step of Example 1, the control unit 185 drives and controls the stage transport mechanism (motor 115) so as to transport the stage 10 from the washing portion 130 to the reagent supply portion 150. In the reagent supply portion 150, a reagent (a 3 vol % aqueous hydrogen peroxide solution) for removing endogenous PO is selected according to the pathological specimen preparation protocol. The control unit 185 drives and controls the reagent supply portion 150 (motor 157) so as to transport the cartridge 50 filled with the reagent (3 vol % aqueous hydrogen peroxide solution) to face the substrate W. Then, the control unit 185 drives and controls the electric pusher 158 so as to drop the reagent (3 vol % aqueous hydrogen peroxide solution) onto the substrate W from the cartridge 50. The dropping amount of the reagent (3 vol % aqueous hydrogen peroxide solution) in this case is, for example, 150 µL (microliters) although it depends on the size of the water-repellent ring 2. After a predetermined amount of the reagent (3 vol % aqueous hydrogen peroxide solution) is supplied to the substrate W, the substrate W is left to stand there for 1 minute, whereby endogenous PO is removed from the tissue specimen Ts (endogenous PO is blocked). Then, the process proceeds to the fourth step.

In the fourth step of Example 1, the control unit 185 drives and controls the stage transport mechanism (motor 115) so as to transport the stage 10 from the reagent supply portion 150 to the washing portion 130. In the washing portion 130, washing with PBS-T is performed in the same manner as in the second step. Then, the process proceeds to the fifth step.

In the fifth step of Example 1, the control unit 185 drives and controls the stage transport mechanism (motor 115) so as to transport the stage 10 from the washing portion 130 to the reagent supply portion 150. In the reagent supply portion 150, a primary antibody reagent (Hep-Par1 which binds to a protein contained in hepatocytes) is selected according to the pathological specimen preparation protocol. The control unit 185 drives and controls the reagent supply portion 150 (motor 157) so as to transport the cartridge 50 filled with the primary antibody reagent to face the substrate W. Then, the control unit 185 drives and controls the electric pusher 158 so as to drop, for example, 150 µL of the primary antibody reagent onto the substrate W from the cartridge 50. Thereafter, the control unit 185 drives and controls the stage transport mechanism (motor 115) so as to transport the stage 10 from the reagent supply portion 150 to the electric field stirring portion 170. In the electric field stirring portion 170, the control unit 185 generates an electric field between the pair of electrodes 10 and 20 and stirs the solution S of the primary antibody reagent supplied to the substrate W. A time required for the electric field stirring is 5 minutes. Then, the process proceeds to the sixth step.

In the sixth step of Example 1, the control unit 185 drives and controls the stage transport mechanism (motor 115) so as to transport the stage 10 from the electric field stirring portion 170 to the washing portion 130. In the washing portion 130, washing with PBS-T is performed in the same manner as in the second step. Then, the process proceeds to the seventh step.

In the seventh step of Example 1, the control unit 185 drives and controls the stage transport mechanism (motor 115) so as to transport the stage 10 from the washing portion 130 to the reagent supply portion 150. In the reagent supply portion 150, a secondary antibody reagent (EnVision+Dual Link which is a sensitizing reagent using a dextran polymer and peroxidase, manufactured by Dako Co., Ltd.) is selected according to the pathological specimen preparation protocol. The control unit 185 drives and controls the reagent supply portion 150 (motor 157) so as to transport the cartridge 50 filled with the secondary antibody reagent to face the substrate W. Then, the control unit 185 drives and controls the electric pusher 158 so as to drop, for example, 150 µL of the secondary antibody reagent onto the substrate W from the cartridge 50. Thereafter, the control unit 185 drives and controls the stage transport mechanism (motor 115) so as to transport the stage 10 from the reagent supply portion 150 to the electric field stirring portion 170. In the electric field stirring portion 170, the control unit 185 generates an electric field between the pair of electrodes 10 and 20 and stirs the solution S of the secondary antibody reagent supplied to the substrate W. A time required for the electric field stirring is 5 minutes. Then, the process proceeds to the eighth step.

In the eighth step of Example 1, the control unit 185 drives and controls the stage transport mechanism (motor 115) so as to transport the stage 10 from the electric field stirring portion 170 to the washing portion 130. In the washing portion 130, washing with PBS-T is performed in the same manner as in the second step. Then, the process proceeds to the ninth step.

In the ninth step of Example 1, the control unit 185 drives and controls the stage transport mechanism (motor 115) so as to transport the stage 10 from the washing portion 130 to the reagent supply portion 150. In the reagent supply portion 150, a reagent (3,3'-diaminobenzidine (DAB)) for causing color development is selected according to the pathological specimen preparation protocol. The control unit 185 drives and controls the reagent supply portion 150 (motor 157) so as to transport the cartridge 50 filled with the reagent (DAB) to face the substrate W. Then, the control unit 185 drives and controls the electric pusher 158 so as to drop the reagent (DAB) onto the substrate W from the cartridge 50. The dropping amount of the reagent (DAB) in this case is, for example, 150 µL. After a predetermined amount of the reagent (DAB) is supplied to the substrate W, the substrate W is left to stand there for 3 minutes so as to allow the tissue specimen Ts and the reagent (DAB) to react with each other and develop a color. Then, the process proceeds to the tenth step.

In the tenth step of Example 1, the control unit 185 drives and controls the stage transport mechanism (motor 115) so as to transport the stage 10 from the reagent supply portion 150 to the washing portion 130. In the washing portion 130, the control unit 185 drives and controls the pump P2 and the associated valves so as to eject pure water stored in the tank 107 from the nozzle 131 and allow pure water to continuously flow for 2 minutes. In the washing portion 130, washing is performed by supplying pure water to the substrate W in a state where the control unit 185 drives and controls the stage tilting mechanism so as to tilt the stage 10. Pure water used for washing contains the reagent (DAB) containing a carcinogenic substance, and therefore, pure water goes through the liquid discharge guide portion 126 from the tilted substrate W, and is guided to the second discharge flow path 142 by the flow path switching mechanism 140 and discharged and stored in the tank 109. Then, the process proceeds to the eleventh step.

In the eleventh step of Example 1, the control unit 185 drives and controls the stage transport mechanism (motor 115) so as to transport the stage 10 from the washing portion 130 to the reagent supply portion 150. In the reagent supply portion 150, a reagent (hematoxylin) for causing nuclear staining (counterstaining) is selected according to the pathological specimen preparation protocol. The control unit 185 drives and controls the reagent supply portion 150 (motor 157) so as to transport the cartridge 50 filled with the reagent (hematoxylin) to face the substrate W. Then, the control unit 185 drives and controls the electric pusher 158 so as to drop the reagent (hematoxylin) onto the substrate W from the cartridge 50. The dropping amount of the reagent (hematoxylin) in this case is, for example, 150 µL. After a predetermined amount of the reagent (hematoxylin) is supplied to the substrate W, the substrate W is left to stand there for 1 minute so as to allow the tissue specimen Ts and the reagent (hematoxylin) to react with each other, thereby performing nuclear staining (counterstaining). Then, the process proceeds to the twelfth step.

In the twelfth step of Example 1, the control unit 185 drives and controls the stage transport mechanism (motor 115) so as to transport the stage 10 from the reagent supply portion 150 to the washing portion 130. In the washing portion 130, the control unit 185 drives and controls the pump P2 and the associated valves so as to eject pure water stored in the tank 107 from the nozzle 131 and allow pure water to continuously flow for 2 minutes. In the washing portion 130, washing is performed by supplying pure water to the substrate W in a state where the control unit 185 drives and controls the stage tilting mechanism so as to tilt the stage 10. Pure water containing the reagent (hematoxylin) goes through the liquid discharge guide portion 126 from the tilted substrate W, and is guided to the first discharge flow path 141 by the flow path switching mechanism 140 and discharged and stored in the tank 108. Then, the control unit 185 drives and controls the stage transport mechanism (motor 115) so as to transport the stage 10 from the washing portion 130 to the starting point. Then, the process proceeds to the thirteenth step.

In the thirteenth step of Example 1, the substrate W is taken out from the stage 10, and in order to prevent dryness of the washed tissue specimen Ts, an encapsulation treatment in which a non-water soluble encapsulating agent is dropped onto the substrate W and the tissue specimen Ts is covered with a cover slip is performed. A time required for the thirteenth step is about 1 minute. Then, the process proceeds to the fourteenth step.

In the fourteenth step of Example 1, by using an image analysis device including an image capture portion, an image of the tissue specimen Ts subjected to the encapsulation treatment is captured, and an image analysis is performed, and then, the depth of staining is digitized. A time required for the fourteenth step is about 1 minute. Incidentally, a pathological diagnosis is performed by preparing a tissue specimen Ts with a positive finding and a tissue specimen Ts with a negative finding, and digitizing the depth of staining based on an image analysis of each of the specimens, followed by comparison.

By going through the above-mentioned steps, the preparation of the pathological specimen by IHC of Example 1 is completed. A time required for the preparation of the pathological specimen of Example 1 was about 25 minutes.

Comparative Example 1

A step of preparing a pathological specimen by IHC of Comparative Example 1 also has the first step of preparing the substrate W having a tissue specimen Ts fixed thereto to the fourteenth step in the same manner as in Example 1 as shown in FIG. 24. However, the first step to the fourteenth step are performed manually without using the pathological specimen preparation system 1000. The pathological specimen preparation protocol in this case is different from that of Example 1. Hereinafter, the operation contents of the respective steps will be specifically described. Incidentally, if at least the second step to the twelfth step of Comparative Example 1 can be reproduced, the preparation of the pathological specimen of Comparative Example 1 may be performed using another pathological specimen preparation device.

A first step (fixing a tissue specimen Ts) of Comparative Example 1 is the same as the first step of Example 1, and the substrate 1 in which a frozen section obtained from a serial section of the same pig liver block as in Example 1 as the tissue specimen Ts is disposed inside the water-repellent ring 2 is immersed in acetone for 2 minutes, whereby the substrate W having the tissue specimen Ts fixed thereto is obtained. Then, the process proceeds to the second step.

In the second step (washing) of Comparative Example 1, three tanks storing PBS-T as the washing solution Cs are prepared, and the substrate W is sequentially immersed in the three tanks for 10 seconds each, thereby washing is performed. That is, a time required for the washing in the second step is 30 seconds. Then, the process proceeds to the third step.

In the third step (step of blocking endogenous PO) of Comparative Example 1, the substrate W is immersed in a 3 vol % aqueous hydrogen peroxide solution for 1 minute, whereby endogenous PO is removed from the tissue specimen Ts. Then, the process proceeds to the fourth step.

In the fourth step (washing) of Comparative Example 1, washing is performed in the same manner as in the second step of Comparative Example 1. That is, a time required for the washing in the fourth step is 30 seconds. Then, the process proceeds to the fifth step.

In the fifth step (primary antibody reaction) of Comparative Example 1, for example, 150 µL of a primary antibody reagent (Hep-Par1) at the same concentration as in Example 1 is dropped onto the washed tissue specimen Ts on the substrate W. As a method of dropping the primary antibody reagent in this case, a method using a micropipette or the like is exemplified. After the primary antibody reagent is dropped, the substrate W is left to stand for 30 minutes, thereby performing a primary antibody reaction. Then, the process proceeds to the sixth step.

In the sixth step (washing) of Comparative Example 1, washing is performed in the same manner as in the second step of Comparative Example 1. That is, a time required for the washing in the sixth step is 30 seconds. Then, the process proceeds to the seventh step.

In the seventh step (secondary antibody reaction) of Comparative Example 1, for example, 150 µL of a secondary antibody reagent (EnVision+Dual Link) at the same concentration as in Example 1 is dropped onto the washed tissue specimen Ts on the substrate W. As a method of dropping the secondary antibody reagent, also a method using a micropipette or the like is exemplified in the same manner as the method of dropping the primary antibody reagent. After the secondary antibody reagent is dropped, the substrate W is left to stand for 30 minutes, thereby performing a secondary antibody reaction. Then, the process proceeds to the eighth step.

In the eighth step (washing) of Comparative Example 1, washing is performed in the same manner as in the second step of Comparative Example 1. That is, a time required for the washing in the eighth step is 30 seconds. Then, the process proceeds to the ninth step.

In the ninth step (color development reaction) of Comparative Example 1, for example, 150 µL of a color developing reagent (DAB) at the same concentration as in Example 1 is dropped onto the washed tissue specimen Ts on the substrate W. As a method of dropping the color developing reagent (DAB), also a method using a micropipette or the like is exemplified. After the color developing reagent (DAB) is dropped, the substrate W is left to stand for 3 minutes, thereby performing a color development reaction. Then, the process proceeds to the tenth step.

In the tenth step (washing) of Comparative Example 1, running water washing is performed by continuously pouring pure water for 2 minutes on the substrate W after completion of the color development reaction. Then, the process proceeds to the eleventh step.

In the eleventh step (nuclear staining) of Comparative Example 1, for example, 150 µL of a counterstaining reagent (hematoxylin) at the same concentration as in Example 1 is dropped onto the washed tissue specimen Ts on the substrate W. As a method of dropping hematoxylin, also a method using a micropipette or the like is exemplified. After hematoxylin is dropped, the substrate W is left to stand for 1 minute, thereby performing a nuclear staining reaction. Then, the process proceeds to the twelfth step.

In the twelfth step (washing) of Comparative Example 1, running water washing is performed by continuously pouring pure water for 2 minutes on the substrate W after completion of the nuclear staining reaction. The thirteenth step (encapsulation) and the fourteenth step (analysis) of Comparative Example 1 are the same as those of Example 1. By going through the above-mentioned steps, the preparation of the pathological specimen by IHC of Comparative Example 1 is completed. A time required for the preparation of the pathological specimen of Comparative Example 1 was about 75 minutes, and it took three times or more longer than about 25 minutes in Example 1. There was almost no difference in staining results between Example 1 and Comparative Example 1. In Example 1, by performing electric field stirring in the fifth step (primary antibody reaction) and the seventh step (secondary antibody reaction), the reaction time could be significantly reduced.

IHC using a frozen section is favorably used, for example, in the case where a pathological diagnosis is performed by collecting a tissue during surgery. When surgery is stopped on the way while performing a pathological diagnosis, a burden may be imposed on a patient. Therefore, a time required for the preparation of a pathological specimen is preferably as short as possible.

<Immunohistochemical Staining (IHC) Using Paraffin-Embedded Section in Example 2 and Comparative Example 2>

FIG. 25 is a table showing a step of preparing a pathological specimen by immunohistochemical staining of Example 2, and FIG. 26 is a table showing a step of preparing a pathological specimen in immunohistochemical staining of Comparative Example 2. The use of a paraffin-embedded section is superior to the case where a frozen section is used in that by embedding a collected tissue in paraffin, the tissue can be stored over a long period of time, and a pathological specimen can be repeatedly prepared. On the other hand, when a pathological specimen is actually prepared, water in the tissue replaced with paraffin is restored to the original state, and therefore, a deparaffinization treatment and an antigen activation treatment are needed. In these treatment steps, heating is needed. First, preparation of a pathological specimen by IHC using a paraffin-embedded section of Example 2 will be described.

Example 2

As shown in FIG. 25, a method for preparing a pathological specimen of Example 2 has a first step of subjecting a paraffin-embedded section to a deparaffinization treatment, a second step of washing the tissue specimen Ts subjected to the deparaffinization treatment, a third step of subjecting the washed tissue specimen Ts to an antigen activation treatment, a fourth step of washing the tissue specimen Ts subjected to the antigen activation treatment, a fifth step of removing endogenous PO in the tissue specimen Ts, a sixth step of washing the tissue specimen Ts from which endogenous PO is removed, a seventh step of performing a primary antibody reaction, an eighth step of washing the tissue specimen Ts subjected to the primary antibody reaction treatment, a ninth step of performing a secondary antibody reaction, a tenth step of washing the tissue specimen Ts subjected to the secondary antibody reaction treatment, an eleventh step of allowing the washed tissue specimen Ts to develop a color, a twelfth step of washing the tissue specimen Ts allowed to develop a color, a thirteenth step of subjecting the washed tissue specimen Ts to nuclear staining, a fourteenth step of washing the tissue specimen Ts subjected to nuclear staining, a fifteenth step of clearing the washed tissue specimen Ts, a sixteenth step of encapsulating the cleared tissue specimen Ts, and a seventeenth step of digitizing the depth of staining by performing an image analysis of the encapsulated tissue specimen Ts. These steps are stored in the memory 503 of the computer 500 as the pathological specimen preparation protocol on the premise that the pathological specimen preparation system 1000 is used. The computer 500 sends a control signal according to the pathological specimen preparation protocol to the control unit 185 of the pathological specimen preparation device 100 in the respective steps from the first step to the fourteenth step, and the control unit 185 drives and controls the pathological specimen preparation device 100 so as to perform the treatments in the respective steps.

In the first step of Example 2, as the tissue specimen Ts, a paraffin-embedded section of a pig liver block is disposed inside the water-repellent ring 2 of the substrate 1, and thereafter the substrate 1 is mounted on the stage 10 of the stage portion 110. The control unit 185 drives and controls the stage transport mechanism (motor 115) so as to transport the stage 10 from the starting point to the reagent supply portion 150. In the reagent supply portion 150, a reagent (a deparaffinization solution, for example, EZ buffer (10×) (Roche; 950-102)) to be used for a deparaffinization treatment is selected according to the pathological specimen preparation protocol. The control unit 185 drives and controls the reagent supply portion 150 (motor 157) so as to transport the cartridge 50 filled with the reagent (deparaffinization solution) to face the substrate 1. Then, the control unit 185 drives and controls the electric pusher 158 so as to drop the reagent (deparaffinization solution) onto the substrate 1 from the cartridge 50. The dropping amount of the reagent (deparaffinization solution) in this case is, for example, 200 µL. After a predetermined amount of the reagent (deparaffinization solution) is supplied to the substrate 1, the control unit 185 controls the Peltier controller 184 so as to allow an electric current to flow in the Peltier element 15 and heat the stage 10 to about 75° C. Then, the substrate 1 is left to stand there for 1 minute so as to allow the tissue specimen Ts and the reagent (deparaffinization solution) to react with each other, thereby performing a deparaffinization treatment. After the substrate 1 is left to stand for 1 minute, the control unit 185 drives and controls the stage transport mechanism (motor 115) so as to transport the stage 10 from the reagent supply portion 150 to the washing portion 130. In the washing portion 130, a waste liquid treatment in which the stage 10 is tilted by the stage tilting mechanism so that the reagent (deparaffinization solution) goes through the liquid discharge guide portion 126 from the top of the substrate 1, and is discharged to the tank 108 from the first discharge flow path 141 is performed. In the first step, such a deparaffinization treatment and a waste liquid treatment are repeatedly performed three times. Then, the process proceeds to the second step.

In the second step of Example 2, after completion of the waste liquid treatment, in the washing portion 130, the control unit 185 drives and controls the pump P1 and the associated valves so as to eject the washing solution (PBS-T) stored in the tank 106 from the nozzle 131 and allow the washing solution to continuously flow for 30 seconds. In the washing portion 130, washing is performed by supplying PBS-T to the substrate 1 in a state where the stage 10 is tilted by the stage tilting mechanism. PBS-T used for washing goes through the liquid discharge guide portion 126 from the tilted substrate 1, and is guided to the first discharge flow path 141 by the flow path switching mechanism 140 and discharged to the tank 108. By going through the first step and the second step, the paraffin-embedded section is subjected to the deparaffinization treatment, whereby the substrate W in which the tissue specimen Ts is fixed to the substrate 1 is obtained. Incidentally, during this process, the control unit 185 detects the output from the temperature sensor 16 attached to the stage 10 and controls the Peltier controller 184 so as to maintain the temperature of the stage 10 at 75° C. Then, the process proceeds to the third step.

In the third step of Example 2, the control unit 185 drives and controls the stage transport mechanism (motor 115) so as to transport the stage 10 from the washing portion 130 to the reagent supply portion 150. In the reagent supply portion 150, a reagent (activation solution) to be used for the antigen activation treatment is selected according to the pathological specimen preparation protocol. The control unit 185 drives and controls the reagent supply portion 150 (motor 157) so as to transport the cartridge 50 filled with the reagent (activation solution) to face the substrate W. Then, the control unit 185 drives and controls the electric pusher 158 so as to drop the reagent (activation solution) onto the substrate W from the cartridge 50. The dropping amount of the reagent (hematoxylin) in this case is, for example, 200 µL. After a predetermined amount of the reagent (activation solution) is supplied to the substrate W, the control unit 185 controls the Peltier controller 184 so as to raise the temperature of the stage 10 from 75° C. to 95° C. Subsequently, the control unit 185 drives and controls the reagent supply portion 150 (motor 157) so as to transport the cartridge 50 filled with an oil (liquid paraffin) as a reagent to face the substrate W. Then, the control unit 185 drives and controls the electric pusher 158 so as to drop the oil onto the substrate W from the cartridge 50. The dropping amount of the oil in this case is, for example, 200 µL. That is, by covering the activation solution with the oil, the evaporation of the activation solution by heating is prevented. Then, the substrate W is left to stand there for 40 minutes so as to allow the tissue specimen Ts and the reagent (activation solution) to react with each other, thereby performing an antigen activation treatment. After the substrate W is left to stand for 40 minutes, the control unit 185 controls the Peltier controller 184 so as to stop the application of an electric current to the Peltier element 15, and the stage 10 is naturally cooled by being left to stand for 20 minutes. Incidentally, the direction of the electric current flowing in the Peltier element 15 is reversed by the Peltier controller 184, and the stage 10 may be cooled by the Peltier element 15. Then, the process proceeds to the fourth step.

In the fourth step of Example 2, the control unit 185 drives and controls the stage transport mechanism (motor 115) so as to transport the stage 10 from the reagent supply portion 150 to the washing portion 130. In the washing portion 130, in the same manner as in the above-mentioned second step, the control unit 185 drives and controls the pump P1 and the associated valves so as to eject the washing solution (PBS-T) stored in the tank 106 from the nozzle 131 and allow the washing solution to continuously flow for 30 seconds, whereby washing is performed. Incidentally, the washing solution (PBS-T) is discharged to the tank 108. Then, the process proceeds to the fifth step.

In the fifth step of Example 2, the control unit 185 drives and controls the stage transport mechanism (motor 115) so as to transport the stage 10 from the washing portion 130 to the reagent supply portion 150. In the reagent supply portion 150, according to the pathological specimen preparation protocol, the control unit 185 drives and controls the reagent supply portion 150 (motor 157) so as to transport the cartridge 50 filled with a reagent (a 3 vol % aqueous hydrogen peroxide solution) for removing endogenous PO to face the substrate W. Then, the control unit 185 drives and controls the electric pusher 158 so as to drop the reagent (3 vol % aqueous hydrogen peroxide solution) onto the substrate W from the cartridge 50. The dropping amount of the reagent (3 vol % aqueous hydrogen peroxide solution) in this case is, for example, 200 µL. After a predetermined amount of the reagent (3 vol % aqueous hydrogen peroxide solution) is supplied to the substrate W, the substrate W is left to stand there for 1 minute, whereby endogenous PO is removed from the tissue specimen Ts (endogenous PO is blocked). Then, the process proceeds to the sixth step.

In the sixth step of Example 2, the control unit 185 drives and controls the stage transport mechanism (motor 115) so as to transport the stage 10 from the reagent supply portion 150 to the washing portion 130. In the washing portion 130, washing with PBS-T is performed in the same manner as in the second step. Then, the process proceeds to the seventh step.

In the seventh step of Example 2, the control unit 185 drives and controls the stage transport mechanism (motor 115) so as to transport the stage 10 from the washing portion 130 to the reagent supply portion 150. In the reagent supply portion 150, according to the pathological specimen preparation protocol, the control unit 185 drives and controls the reagent supply portion 150 (motor 157) so as to transport the cartridge 50 filled with a primary antibody reagent (Hep-Par1) to face the substrate W. Then, the control unit 185 drives and controls the electric pusher 158 so as to drop, for example, 200 µL of the primary antibody reagent onto the substrate W from the cartridge 50. Thereafter, the control unit 185 drives and controls the stage transport mechanism (motor 115) so as to transport the stage 10 to the electric field stirring portion 170. In the electric field stirring portion 170, the control unit 185 generates an electric field between the pair of electrodes 10 and 20 and stirs the solution S of the primary antibody reagent supplied to the substrate W. A time required for the electric field stirring in this case is 10 minutes. Then, the process proceeds to the eighth step.

In the eighth step of Example 2, the control unit 185 drives and controls the stage transport mechanism (motor 115) so as to transport the stage 10 from the electric field stirring portion 170 to the washing portion 130. In the washing portion 130, washing with PBS-T is performed in the same manner as in the second step. Then, the process proceeds to the ninth step.

In the ninth step of Example 2, the control unit 185 drives and controls the stage transport mechanism (motor 115) so as to transport the stage 10 from the washing portion 130 to the reagent supply portion 150. In the reagent supply portion 150, according to the pathological specimen preparation protocol, the control unit 185 drives and controls the reagent supply portion 150 (motor 157) so as to transport the cartridge 50 filled with a secondary antibody reagent (En-Vision+Dual Link) to face the substrate W. Then, the control unit 185 drives and controls the electric pusher 158 so as to drop, for example, 200 µL of the secondary antibody reagent onto the substrate W from the cartridge 50. Thereafter, the control unit 185 drives and controls the stage transport mechanism (motor 115) so as to transport the stage 10 to the electric field stirring portion 170. In the electric field stirring portion 170, the control unit 185 generates an electric field between the pair of electrodes 10 and 20 and stirs the solution S of the secondary antibody reagent supplied to the substrate W. A time required for the electric field stirring in this case is 7 minutes. Then, the process proceeds to the tenth step.

In the tenth step of Example 2, the control unit 185 drives and controls the stage transport mechanism (motor 115) so as to transport the stage 10 from the electric field stirring portion 170 to the washing portion 130. In the washing portion 130, washing with PBS-T is performed in the same manner as in the second step. Then, the process proceeds to the eleventh step.

In the eleventh step of Example 2, the control unit 185 drives and controls the stage transport mechanism (motor 115) so as to transport the stage 10 from the washing portion 130 to the reagent supply portion 150. In the reagent supply portion 150, according to the pathological specimen preparation protocol, the control unit 185 drives and controls the reagent supply portion 150 (motor 157) so as to transport the cartridge 50 filled with a reagent (DAB) for causing color development to face the substrate W. Then, the control unit 185 drives and controls the electric pusher 158 so as to drop the reagent (DAB) onto the substrate W from the cartridge 50. The dropping amount of the reagent (DAB) in this case is, for example, 200 µL. After a predetermined amount of the reagent (DAB) is supplied to the substrate W, the substrate W is left to stand there for 3 minutes so as to allow the tissue specimen Ts and the reagent (DAB) to react with each other and develop a color. Then, the process proceeds to the twelfth step.

In the twelfth step of Example 2, the control unit 185 drives and controls the stage transport mechanism (motor 115) so as to transport the stage 10 from the reagent supply portion 150 to the washing portion 130. In the washing portion 130, the control unit 185 drives and controls the pump P2 and the associated valves so as to eject pure water stored in the tank 107 from the nozzle 131 and allow pure water to continuously flow for 2 minutes. In the washing portion 130, washing is performed by supplying pure water to the substrate W in a state where the control unit 185 drives and controls the stage tilting mechanism so as to tilt the stage 10. Pure water which contains the reagent (DAB) containing a carcinogenic substance goes through the liquid discharge guide portion 126 from the tilted substrate W, and is guided to the second discharge flow path 142 by the flow path switching mechanism 140 and discharged to the tank 109. Then, the process proceeds to the thirteenth step.

In the thirteenth step of Example 2, the control unit 185 drives and controls the stage transport mechanism (motor 115) so as to transport the stage 10 from the washing portion 130 to the reagent supply portion 150. In the reagent supply portion 150, according to the pathological specimen preparation protocol, the control unit 185 drives and controls the reagent supply portion 150 (motor 157) so as to transport the cartridge 50 filled with a reagent (hematoxylin) for causing nuclear staining (counterstaining) to face the substrate W. Then, the control unit 185 drives and controls the electric pusher 158 so as to drop the reagent (hematoxylin) onto the substrate W from the cartridge 50. The dropping amount of the reagent (hematoxylin) in this case is, for example, 200 µL. After a predetermined amount of the reagent (hematoxylin) is supplied to the substrate W, the substrate W is left to stand there for 1 minute so as to allow the tissue specimen Ts and the reagent (hematoxylin) to react with each other, thereby performing nuclear staining (counterstaining). Then, the process proceeds to the fourteenth step.

In the fourteenth step of Example 2, the control unit 185 drives and controls the stage transport mechanism (motor 115) so as to transport the stage 10 from the reagent supply portion 150 to the washing portion 130. In the washing portion 130, the control unit 185 drives and controls the pump P2 and the associated valves so as to eject pure water stored in the tank 107 from the nozzle 131 and allow pure water to continuously flow for 2 minutes. In the washing portion 130, washing is performed by supplying pure water to the substrate W in a state where the stage 10 is tilted by the stage tilting mechanism. Pure water containing the reagent (hematoxylin) goes through the liquid discharge guide portion 126 from the tilted substrate W, and is guided to the first discharge flow path 141 by the flow path switching mechanism 140 and discharged and stored in the tank 108. Then, the control unit 185 drives and controls the stage transport mechanism (motor 115) so as to transport the stage 10 from the washing portion 130 to the starting point. Then, the process proceeds to the fifteenth step. Incidentally, the treatments up to the fourteenth step are performed using the pathological specimen preparation device 100.

In the fifteenth step of Example 2, the substrate W is taken out from the stage 10, and in order to further improve the contrast ratio in the staining of the tissue specimen Ts subjected to the nuclear staining, a dehydration treatment in which water is removed from the tissue specimen Ts using ethanol, and a clearing treatment in which the transparency of the tissue specimen Ts is improved by replacing ethanol with xylene are performed. More specifically, five tanks storing anhydrous ethanol (99.5 vol % or more) and also five tanks storing xylene are prepared, and the substrate W is sequentially immersed in a total of ten tanks from anhydrous ethanol for 10 seconds each. Therefore, a time required for the immersion is 100 seconds. Then, the process proceeds to the sixteenth step. Incidentally, in the dehydration treatment, five tanks containing ethanol in which the concentration is changed stepwise from 75 vol % to 99.5 vol % or more may be used.

In the sixteenth step of Example 2, in order to prevent dryness of the tissue specimen Ts subjected to the clearing treatment, an encapsulation treatment in which a non-water soluble encapsulating agent is dropped onto the substrate W and the tissue specimen Ts is covered with a cover slip is performed. A time required for the encapsulation treatment is about 1 minute. Then, the process proceeds to the seventeenth step.

In the seventeenth step of Example 2, by using an image analysis device including an image capture portion, an image of the tissue specimen Ts subjected to the clearing treatment is captured, and an image analysis is performed, and then, the depth of staining is digitized. A time required for the image analysis is about 1 minute. Incidentally, a pathological diagnosis is performed by preparing a tissue specimen Ts with a positive finding and a tissue specimen Ts with a negative finding, and digitizing the depth of staining based on an image analysis of each of the specimens, followed by comparison.

A time required for the preparation of the pathological specimen of Example 2 (from the first step to the seventeenth step) was about 96 minutes.

Comparative Example 2

As shown in FIG. 26, a step of preparing a pathological specimen by IHC of Comparative Example 2 also has the first step of performing a deparaffinization treatment to the seventeenth step of performing an analysis in the same manner as in Example 2. However, the first step to the seventeenth step are performed manually without using the pathological specimen preparation system 1000. The pathological specimen preparation protocol in this case is different from that of Example 2. Hereinafter, the operation contents of the respective steps will be specifically described. Incidentally, if at least the first step to the fourteenth step of Comparative Example 2 can be reproduced, the preparation of the pathological specimen of Comparative Example 2 may be performed using another pathological specimen preparation device.

In the first step (deparaffinization treatment) of Comparative Example 2, a treatment of immersing the substrate 1 in which a paraffin-embedded section obtained from a serial section of the same pig liver block as in Example 2 as the tissue specimen Ts is disposed inside the water-repellent ring 2 in three tanks storing xylene for 3 minutes each, and a treatment of immersing the substrate 1 in five tanks storing ethanol for 1 minute each are performed. A time required for the first step is 14 minutes (9 minutes+5 minutes). Then, the process proceeds to the second step.

In the second step (washing) of Comparative Example 2, three tanks storing PBS-T are prepared, and the substrate W is sequentially immersed in the three tanks for 10 seconds each, thereby washing is performed. That is, a time required for the washing in the second step is 30 seconds. By doing this, the substrate W having the tissue specimen Ts fixed thereto is obtained. Then, the process proceeds to the third step.

In the third step (antigen activation treatment) of Comparative Example 2, the substrate W having the tissue specimen Ts fixed thereto is immersed in an activation solution heated to 95° C. for 40 minutes. Then, the substrate W is taken out from the activation solution and naturally cooled by being left to stand at room temperature for 20 minutes. Then, the process proceeds to the fourth step.

In the fourth step (washing) of Comparative Example 2, in the same manner as in the above-mentioned second step, washing is performed by sequentially immersing the substrate W in three tanks housing PBS-T for 10 seconds each. Then, the process proceeds to the fifth step.

In the fifth step (step of blocking endogenous PO) of Comparative Example 2, the substrate W is immersed in a 3 vol % aqueous hydrogen peroxide solution for 5 minutes, whereby endogenous PO is removed from the tissue specimen Ts. Then, the process proceeds to the sixth step.

In the sixth step (washing) of Comparative Example 2, in the same manner as in the above-mentioned second step, washing is performed by sequentially immersing the substrate W in three tanks storing PBS-T for 10 seconds each. Then, the process proceeds to the seventh step.

In the seventh step (primary antibody reaction) of Comparative Example 2, for example, 200 μL of a primary antibody reagent (Hep-Par1) at the same concentration as in Example 2 is dropped onto the washed tissue specimen Ts on the substrate W using, for example, a micropipette or the like. After the primary antibody reagent is dropped, the substrate W is left to stand for 30 minutes, thereby performing a primary antibody reaction. Then, the process proceeds to the eighth step.

In the eighth step (washing) of Comparative Example 2, in the same manner as in the above-mentioned second step, washing is performed by sequentially immersing the substrate W in three tanks housing PBS-T for 10 seconds each. Then, the process proceeds to the ninth step.

In the ninth step (secondary antibody reaction) of Comparative Example 2, for example, 200 μL of a secondary antibody reagent (EnVision+Dual Link) at the same concentration as in Example 2 is dropped onto the washed tissue specimen Ts on the substrate W using, for example, a micropipette or the like. After the secondary antibody reagent is dropped, the substrate W is left to stand for 30 minutes, thereby performing a secondary antibody reaction. Then, the process proceeds to the tenth step.

In the tenth step (washing) of Comparative Example 2, in the same manner as in the above-mentioned second step, washing is performed by sequentially immersing the substrate W in three tanks storing PBS-T for 10 seconds each. Then, the process proceeds to the eleventh step.

In the eleventh step (color development reaction) of Comparative Example 2, for example, 200 μL of a color developing reagent (DAB) at the same concentration as in Example 2 is dropped onto the washed tissue specimen Ts on the substrate W using, for example, a micropipette or the like. After the color developing reagent (DAB) is dropped, the substrate W is left to stand for 3 minutes, thereby performing a color development reaction. Then, the process proceeds to the twelfth step.

In the twelfth step (washing) of Comparative Example 2, running water washing is performed by continuously pouring pure water for 2 minutes on the substrate W after completion of the color development reaction. Then, the process proceeds to the thirteenth step.

In the thirteenth step (nuclear staining) of Comparative Example 2, for example, 200 µL of a counterstaining reagent (hematoxylin) at the same concentration as in Example 2 is dropped onto the washed tissue specimen Ts on the substrate W using, for example, a micropipette or the like. After hematoxylin is dropped, the substrate W is left to stand for 1 minute, thereby performing a nuclear staining reaction. Then, the process proceeds to the fourteenth step.

In the fourteenth step (washing) of Comparative Example 2, running water washing is performed by continuously pouring pure water for 2 minutes on the substrate W after completion of the nuclear staining reaction. Then, the process proceeds to the fifteenth step. The fifteenth step (clearing), the sixteenth step (encapsulation), and the seventeenth step (analysis) are the same as in the above-mentioned Example 2. By going through the above-mentioned steps, the preparation of the pathological specimen by IHC of Comparative Example 2 is completed. A time required for the preparation of the pathological specimen of Comparative Example 2 was about 154 minutes, and it took 58 minutes (approximately 1 hour) longer than about 96 minutes in Example 2. There was almost no difference in staining results between Example 2 and Comparative Example 2. In Example 2, by using the pathological specimen preparation system 1000 (pathological specimen preparation device 100) in the first step to the fourteenth step, the operation time could be reduced.

<In Situ Hybridization (ISH) in Example 3 and Comparative Example 3>

FIG. 27 is a table showing a step of preparing a pathological specimen by in situ hybridization of Example 3, and FIG. 28 is a table showing a step of preparing a pathological specimen in in situ hybridization of Comparative Example 3. In the case where gene expression in a tissue or a cell is examined, while immunohistochemical staining (IHC) mainly detects the distribution or the amount of a specific protein, in situ hybridization detects mRNA (messenger RNA). In the detection of mRNA, specific binding (hybridization) between single-stranded nucleic acid molecules by complementary base sequences is utilized. A nucleic acid molecule to be used in the detection is called "probe". The probe to be used as a reagent is relatively expensive, and therefore, one of the important matters is to save the used amount of the probe by reducing the size or the thickness of the tissue specimen Ts.

Example 3

As shown in FIG. 27, a method for preparing a pathological specimen by ISH of Example 3 is a method using a paraffin-embedded section and has a first step of performing a deparaffinization treatment, a second step of washing the tissue specimen Ts subjected to the deparaffinization treatment, a third step of removing endogenous PO in the washed tissue specimen Ts, a fourth step of washing the tissue specimen Ts from which endogenous PO is removed, a fifth step of subjecting the tissue specimen Ts to a thermal denaturation treatment, a sixth step of performing hybridization, a seventh step of washing the tissue specimen Ts subjected to hybridization, an eighth step of performing a primary antibody reaction, a ninth step of washing the tissue specimen Ts subjected to the primary antibody reaction treatment, a tenth step of performing a secondary antibody reaction, an eleventh step of washing the tissue specimen Ts subjected to the secondary antibody reaction treatment, a twelfth step of allowing the washed tissue specimen Ts to develop a color, a thirteenth step of washing the tissue specimen Ts allowed to develop a color, a fourteenth step of subjecting the washed tissue specimen Ts to nuclear staining, a fifteenth step of washing the tissue specimen Ts subjected to nuclear staining, a sixteenth step of clearing the washed tissue specimen Ts, a seventeenth step of encapsulating the cleared tissue specimen Ts, and an eighteenth step of digitizing the depth of staining by performing an image analysis of the encapsulated tissue specimen Ts. These steps are stored in the memory 503 of the computer 500 as the pathological specimen preparation protocol on the premise that the pathological specimen preparation system 1000 is used. The computer 500 sends a control signal according to the pathological specimen preparation protocol to the control unit 185 of the pathological specimen preparation device 100 in the respective steps from the fifth step to the fifteenth step, and the control unit 185 drives and controls the pathological specimen preparation device 100 so as to perform the treatments in the respective steps.

The first step (deparaffinization treatment), the second step (washing), the third step (removal of endogenous PO), and the fourth step (washing) of Example 3 are the same as the first step (deparaffinization treatment), the second step (washing), the fifth step (removal of endogenous PO), and the sixth step (washing) of Example 2 described above. Incidentally, the fifth step (thermal denaturation treatment) of Example 3 is a step of performing a heat treatment for separating a double-stranded nucleic acid in a cell in the tissue specimen Ts into single strands. Hereinafter, a description will be given from the fifth step different from Example 2.

In the fifth step (thermal denaturation treatment) of Example 3, the substrate W having the tissue specimen Ts from which endogenous PO is removed fixed thereto is mounted on the stage 10 of the pathological specimen preparation device 100. The control unit 185 drives and controls the stage transport mechanism (motor 115) so as to transport the stage 10 from the starting point to the reagent supply portion 150. In the reagent supply portion 150, according to the pathological specimen preparation protocol, the control unit 185 drives and controls the reagent supply portion 150 (motor 157) so as to transport the cartridge 50 filled with a reagent (probe) to face the substrate W. Then, the control unit 185 drives and controls the electric pusher 158 so as to drop the reagent (probe) onto the substrate W from the cartridge 50. The dropping amount of the reagent (probe) in this case is, for example, 10 µL. Subsequently, the control unit 185 drives and controls the reagent supply portion 150 (motor 157) so as to transport the cartridge 50 filled with an oil (liquid paraffin) as a reagent to face the substrate W. Then, the control unit 185 drives and controls the electric pusher 158 so as to drop the oil onto the substrate W from the cartridge 50. The dropping amount of the oil in this case is, for example, 40 µL. That is, by covering the probe with the oil, the evaporation of the probe by heating is prevented. Further, in order to efficiently perform electric field stirring thereafter, the oil is further added to the reagent (probe) so as to increase the volume of the solution S during electric field stirring. The control unit 185 controls the Peltier controller 184 so as to allow an electric current to flow in the Peltier element 15, thereby heating the stage 10 to 95° C., and then, the stage 10 is left to stand for about 10 minutes. Thereafter, the application of an electric current to the Peltier element 15 is stopped to allow the stage 10 to naturally cool for 20 minutes. Then, the process proceeds to the sixth step.

In the sixth step (hybridization) of Example 3, the control unit 185 drives and controls the stage transport mechanism (motor 115) so as to transport the stage 10 from the reagent supply portion 150 to the electric field stirring portion 170. In the electric field stirring portion 170, the control unit 185 controls the Peltier controller 184 so as to allow an electric current to flow in the Peltier element 15, thereby heating the stage 10 to 37° C. and also generates an electric field between the pair of electrodes 10 and 20, thereby stirring the solution S containing the probe and the oil by the electric field. A time required for the electric field stirring is 180 minutes. By doing this, the tissue specimen Ts subjected to the thermal denaturation treatment (that is, the single-stranded nucleic acid) and the reagent (probe) are allowed to react with each other, thereby performing hybridization (complementary binding reaction). Then, the process proceeds to the seventh step.

In the seventh (washing) step of Example 3, the control unit 185 drives and controls the stage transport mechanism (motor 115) so as to transport the stage 10 from the electric field stirring portion 170 to the washing portion 130. In the washing portion 130, in the same manner as in the second step of Comparative Example 2 described above, the control unit 185 drives and controls the pump P1 and the associated valves so as to eject the washing solution (PBS-T) stored in the tank 106 from the nozzle 131 and allow the washing solution to continuously flow for 30 seconds, whereby washing is performed. Incidentally, the washing solution (PBS-T) is discharged to the tank 108. Then, the process proceeds to the eighth step.

In the eighth step (primary antibody reaction) of Example 3, the control unit 185 drives and controls the stage transport mechanism (motor 115) so as to transport the stage 10 from the washing portion 130 to the reagent supply portion 150. In the reagent supply portion 150, according to the pathological specimen preparation protocol, the control unit 185 drives and controls the reagent supply portion 150 (motor 157) so as to transport the cartridge 50 filled with a primary antibody reagent (Hep-Par1) to face the substrate W. Then, the control unit 185 drives and controls the electric pusher 158 so as to drop, for example, 30 µL of the primary antibody reagent onto the substrate W from the cartridge 50. Subsequently, the control unit 185 drives and controls the reagent supply portion 150 (motor 157) so as to transport the cartridge 50 filled with an oil (liquid paraffin) as a reagent to face the substrate W. Then, the control unit 185 drives and controls the electric pusher 158 so as to drop the oil onto the substrate W from the cartridge 50. The dropping amount of the oil in this case is, for example, 30 µL. That is, by covering the primary antibody reagent with the oil, the evaporation of the primary antibody reagent is prevented. Further, in order to efficiently perform electric field stirring thereafter, the oil is further added to the primary antibody reagent so as to increase the volume of the solution S during electric field stirring. Thereafter, the control unit 185 drives and controls the stage transport mechanism (motor 115) so as to transport the stage 10 from the reagent supply portion 150 to the electric field stirring portion 170. In the electric field stirring portion 170, the control unit 185 generates an electric field between the pair of electrodes 10 and 20 and stirs the solution S containing the primary antibody reagent and the oil supplied to the substrate W. A time required for the electric field stirring in this case is 5 minutes. Then, the process proceeds to the ninth step.

In the ninth step (washing) of Example 3, the control unit 185 drives and controls the stage transport mechanism (motor 115) so as to transport the stage 10 from the electric field stirring portion 170 to the washing portion 130. In the washing portion 130, in the same manner as in the above-mentioned seventh step (washing), continuous flow washing with PBS-T is performed. Then, the process proceeds to the tenth step.

In the tenth step (secondary antibody reaction) of Example 3, the control unit 185 drives and controls the stage transport mechanism (motor 115) so as to transport the stage 10 from the washing portion 130 to the reagent supply portion 150. In the reagent supply portion 150, according to the pathological specimen preparation protocol, the control unit 185 drives and controls the reagent supply portion 150 (motor 157) so as to transport the cartridge 50 filled with a secondary antibody reagent (EnVision+Dual Link) to face the substrate W. Then, the control unit 185 drives and controls the electric pusher 158 so as to drop, for example, 30 µL of the secondary antibody reagent onto the substrate W from the cartridge 50. Subsequently, the control unit 185 drives and controls the reagent supply portion 150 (motor 157) so as to transport the cartridge 50 filled with an oil (liquid paraffin) as a reagent to face the substrate W. Then, the control unit 185 drives and controls the electric pusher 158 so as to drop the oil onto the substrate W from the cartridge 50. The dropping amount of the oil in this case is, for example, 30 µL. That is, by covering the secondary antibody reagent with the oil, the evaporation of the secondary antibody reagent is prevented. Further, in order to efficiently perform electric field stirring thereafter, the oil is further added to the secondary antibody reagent so as to increase the volume of the solution S during electric field stirring. Thereafter, the control unit 185 drives and controls the stage transport mechanism (motor 115) so as to transport the stage 10 from the reagent supply portion 150 to the electric field stirring portion 170. In the electric field stirring portion 170, the control unit 185 generates an electric field between the pair of electrodes 10 and 20 and stirs the solution S containing the secondary antibody reagent and the oil supplied to the substrate W. A time required for the electric field stirring in this case is 5 minutes. Then, the process proceeds to the eleventh step.

In the eleventh step (washing) of Example 3, the control unit 185 drives and controls the stage transport mechanism (motor 115) so as to transport the stage 10 from the electric field stirring portion 170 to the washing portion 130. In the washing portion 130, in the same manner as in the above-mentioned seventh step (washing), continuous flow washing with PBS-T is performed. Then, the process proceeds to the twelfth step.

In the twelfth step (color development) of Example 3, the control unit 185 drives and controls the stage transport mechanism (motor 115) so as to transport the stage 10 from the washing portion 130 to the reagent supply portion 150. In the reagent supply portion 150, according to the pathological specimen preparation protocol, the control unit 185 drives and controls the reagent supply portion 150 (motor 157) so as to transport the cartridge 50 filled with a reagent (DAB) for causing color development to face the substrate W. Then, the control unit 185 drives and controls the electric pusher 158 so as to drop the reagent (DAB) onto the substrate W from the cartridge 50. The dropping amount of the reagent (DAB) in this case is, for example, 60 µL. After a predetermined amount of the reagent (DAB) is supplied to the substrate W, the substrate W is left to stand there for 3 minutes so as to allow the tissue specimen Ts and the reagent (DAB) to react with each other and develop a color. Then, the process proceeds to the thirteenth step.

In the thirteenth step (washing) of Example 3, the control unit 185 drives and controls the stage transport mechanism (motor 115) so as to transport the stage 10 from the reagent supply portion 150 to the washing portion 130. In the washing portion 130, the control unit 185 drives and controls the pump P2 and the associated valves so as to eject pure water stored in the tank 107 from the nozzle 131 and allow pure water to continuously flow for 2 minutes. In the washing portion 130, washing is performed by supplying pure water to the substrate W in a state where the control unit 185 drives and controls the stage tilting mechanism so as to tilt the stage 10. Pure water which contains the reagent (DAB) containing a carcinogenic substance goes through the liquid discharge guide portion 126 from the tilted substrate W, and is guided to the second discharge flow path 142 by the flow path switching mechanism 140 and discharged to the tank 109. Then, the process proceeds to the fourteenth step.

In the fourteenth step (nuclear staining) of Example 3, the control unit 185 drives and controls the stage transport mechanism (motor 115) so as to transport the stage 10 from the washing portion 130 to the reagent supply portion 150. In the reagent supply portion 150, according to the pathological specimen preparation protocol, the control unit 185 drives and controls the reagent supply portion 150 (motor 157) so as to transport the cartridge 50 filled with a reagent (hematoxylin) for causing nuclear staining (counterstaining) to face the substrate W. Then, the control unit 185 drives and controls the electric pusher 158 so as to drop the reagent (hematoxylin) onto the substrate W from the cartridge 50. The dropping amount of the reagent (hematoxylin) in this case is, for example, 100 µL. After a predetermined amount of the reagent (hematoxylin) is supplied to the substrate W, the substrate W is left to stand there for 1 minute so as to allow the tissue specimen Ts and the reagent (hematoxylin) to react with each other, thereby performing nuclear staining (counterstaining). Then, the process proceeds to the fifteenth step.

In the fifteenth step (washing) of Example 3, the control unit 185 drives and controls the stage transport mechanism (motor 115) so as to transport the stage 10 from the reagent supply portion 150 to the washing portion 130. In the washing portion 130, the control unit 185 drives and controls the pump P2 and the associated valves so as to eject pure water stored in the tank 107 from the nozzle 131 and allow pure water to continuously flow for 2 minutes. In the washing portion 130, washing is performed by supplying pure water to the substrate W in a state where the stage 10 is tilted by the stage tilting mechanism. Pure water containing the reagent (hematoxylin) goes through the liquid discharge guide portion 126 from the tilted substrate W, and is guided to the first discharge flow path 141 by the flow path switching mechanism 140 and discharged and stored in the tank 108. Then, the control unit 185 drives and controls the stage transport mechanism (motor 115) so as to transport the stage 10 from the washing portion 130 to the starting point. Then, the process proceeds to the sixteenth step. Incidentally, the treatments in the fifth step to the fifteenth step are performed using the pathological specimen preparation device 100.

The sixteenth step (clearing), the seventeenth step (encapsulation), and the eighteenth step (analysis) of Example 3 are the same as the fifteenth step (clearing), the sixteenth step (encapsulation), and the seventeenth step (analysis) in the above-mentioned Example 2 or Comparative Example 2.

A time required for the preparation of the pathological specimen (the first step to the eighteenth step) of Example 3 was about 254 minutes.

Comparative Example 3

As shown in FIG. 28, a step of preparing a pathological specimen by ISH of Comparative Example 3 also has the first step of performing a deparaffinization treatment to the eighteenth step of performing an analysis in the same manner as in Example 3. The first step to the fourth step and the sixteenth step to the eighteenth step of Comparative Example 3 are the same as those of Example 3. The fifth step to the fifteenth step are performed manually without using the pathological specimen preparation system 1000. The pathological specimen preparation protocol in this case is different from that of Example 3. Hereinafter, with respect to the steps different from those of Example 3, the operation contents will be specifically described. Incidentally, if at least the fifth step to the fifteenth step of Comparative Example 3 can be reproduced, the preparation of the pathological specimen of Comparative Example 3 may be performed using another pathological specimen preparation device. Further, as the tissue specimen Ts of Comparative Example 3, a paraffin-embedded section obtained from a serial section of the same pig liver block as in Example 3 is used.

In the fifth step (thermal denaturation treatment) of Comparative Example 3, for example, 10 µL of a reagent (probe) at the same concentration as in Example 3 is dropped onto the tissue specimen Ts fixed to the substrate W. Subsequently, for example, 40 µL of an oil is dropped thereon so as to cover the probe with the oil. The substrate W is heated to 95° C. in a state where the probe is covered with the oil, and then left to stand for 10 minutes, thereby performing a thermal denaturation treatment. Thereafter, the substrate W is naturally cooled to room temperature by being left to stand for 20 minutes. Incidentally, as a method of dropping the probe or the oil, for example, a micropipette is used. Then, the process proceeds to the sixth step.

In the sixth step (hybridization) of Comparative Example 3, the substrate W is heated to 37° C., and then left to stand for 720 minutes, thereby performing hybridization. Then, the process proceeds to the seventh step.

In the seventh step (washing) of Comparative Example 3, washing is performed by allowing PBS-T as the washing solution to continuously flow onto the substrate W for 30 seconds. Then, the process proceeds to the eighth step.

In the eighth step (primary antibody reaction) of Comparative Example 3, for example, 30 µL of a primary antibody reagent (Hep-Par1) at the same concentration as in Example 3 is dropped onto the washed tissue specimen Ts on the substrate W using, for example, a micropipette or the like. Subsequently, for example, 30 µL of an oil is dropped thereon. After the primary antibody reagent is covered with the oil, the substrate W is left to stand for 20 minutes, thereby performing a primary antibody reaction. Then, the process proceeds to the ninth step.

In the ninth step (washing) of Comparative Example 3, washing is performed by allowing PBS-T to continuously flow onto the substrate W for 30 seconds in the same manner as in the above-mentioned seventh step (washing). Then, the process proceeds to the tenth step.

In the tenth step (secondary antibody reaction) of Comparative Example 3, for example, 30 µL of a secondary antibody reagent (EnVision+Dual Link) at the same concentration as in Example 3 is dropped onto the washed tissue specimen Ts on the substrate W using, for example, a micropipette or the like. Subsequently, for example, 30 µL of an oil is dropped thereon. After the secondary antibody reagent is covered with the oil, the substrate W is left to stand for 20 minutes, thereby performing a secondary antibody reaction. Then, the process proceeds to the eleventh step.

In the eleventh step (washing) of Comparative Example 3, washing is performed by allowing PBS-T to continuously flow onto the substrate W for 30 seconds in the same manner as in the above-mentioned seventh step (washing). Then, the process proceeds to the twelfth step.

In the twelfth step (color development reaction) of Comparative Example 3, for example, 60 µL of a color developing reagent (DAB) at the same concentration as in Example 3 is dropped onto the washed tissue specimen Ts on the substrate W using, for example, a micropipette or the like. After the color developing reagent (DAB) is dropped, the substrate W is left to stand for 3 minutes, thereby performing a color development reaction. Then, the process proceeds to the thirteenth step.

In the thirteenth step (washing) of Comparative Example 3, running water washing is performed by continuously pouring pure water for 2 minutes on the substrate W after completion of the color development reaction. Then, the process proceeds to the fourteenth step.

In the fourteenth step (nuclear staining) of Comparative Example 3, for example, 100 µL of a counterstaining reagent (hematoxylin) at the same concentration as in Example 3 is dropped onto the washed tissue specimen Ts on the substrate W using, for example, a micropipette or the like. After hematoxylin is dropped, the substrate W is left to stand for 1 minute, thereby performing a nuclear staining reaction. Then, the process proceeds to the fifteenth step.

In the fifteenth step (washing) of Comparative Example 3, running water washing is performed by continuously pouring pure water for 2 minutes on the substrate W after completion of the nuclear staining reaction. Then, the process proceeds to the sixteenth step. The sixteenth step (clearing), the seventeenth step (encapsulation), and the eighteenth step (analysis) of Comparative Example 3 are the same as those of the above-mentioned Example 3. By going through the above-mentioned steps, the preparation of the pathological specimen by ISH of Comparative Example 3 is completed. A time required for the preparation of the pathological specimen of Comparative Example 3 was about 824 minutes, and it took 570 minutes (approximately 9.5 hours) longer than about 254 minutes in Example 3. There was almost no difference in staining results between Example 3 and Comparative Example 3. In Example 3, by using the pathological specimen preparation system 1000 (pathological specimen preparation device 100) in the fifth step to the fifteenth step, the operation time could be reduced.

According to the pathological specimen preparation device 100 and the pathological specimen preparation system 1000 including the pathological specimen preparation device 100 of the above-mentioned embodiment, the following effects can be obtained.

(1) The pathological specimen preparation device 100 has a plurality of stage portions 110, and therefore, a pathological specimen can be prepared by using six substrates W each having the tissue specimen Ts fixed thereto at the maximum.

(2) The stage portion 110 includes the stage transport mechanism and the stage tilting mechanism and is disposed on the second plate 102 of the frame 105, and therefore, for example, when a problem occurs in the stage portion 110, maintenance such as replacement of the stage portion 110 in a state of including the stage transport mechanism and the stage tilting mechanism can be performed.

(3) The stage tilting mechanism is configured such that by the movement of transporting the stage 10 to the washing portion 130 toward the starting point in the Y direction by the stage transport mechanism, the support rod 121 which rides on the cam 125 pushes up the bottom face 12 of the stage 10 from the lower side, thereby tilting the stage 10. Therefore, a dedicated driving system such as a motor for tilting the stage 10 is not needed, and thus, a simple device configuration can be achieved.

(4) By the stage tilting mechanism, the upper face 11 of the stage 10 is tilted by 60° or more from a horizontal state in the washing portion 130, and therefore, the reagent Rs or the washing solution Cs supplied to the substrate W or the washing solution Cs containing the reagent Rs can be reliably discharged from the substrate W. In other words, a pathological specimen can be properly prepared by reducing or preventing the effect of the reagent Rs or the washing solution Cs or the washing solution Cs containing the reagent Rs remaining on the substrate W on various types of treatments in the preparation of the pathological specimen.

(5) The pathological specimen preparation device 100 can discharge the reagent Rs or the washing solution Cs or the washing solution Cs containing the reagent Rs discharged from the substrate W to either the tank 108 or the tank 109 serving as a waste liquid tank by the liquid discharge guide portion 126 provided in the stage portion 110 and the flow path switching mechanism 140 disposed on the second plate 102. In other words, in the case where the waste liquid treatment differs depending on the type of the liquid to be discharged, a specific liquid can be sorted and discharged and stored in a specific tank.

(6) The electric field stirring portion 170 is included, and therefore, a time required for the primary antibody reaction or the secondary antibody reaction, or the hybridization in the preparation of a pathological specimen can be reduced. Incidentally, the step to which electric field stirring can be applied is not limited to the primary antibody reaction, the secondary antibody reaction, or the hybridization, and electric field stirring may be applied to the color development reaction or the washing step. According to this, the treatment time can be further reduced.

(7) To the stage 10, the Peltier element 15 and the temperature sensor 16 are attached. Further, the pathological specimen preparation device 100 includes the Peltier controller 184. Therefore, the device can also properly cope with the preparation of a pathological specimen which requires heating of the substrate W as in the case of a deparaffinization treatment, a thermal denaturation treatment, or hybridization.

(8) The pathological specimen preparation system 1000 includes not only the barcode reader 162 provided in the pathological specimen preparation device 100, but also the barcode reader 506 connected to the computer 500. Therefore, according to the pathological specimen preparation protocol, the management of the reagent Rs filled in the cartridge 50 or the management of the cartridge 50, that is, the reagent Rs to be used in the step of preparing a pathological specimen can be reliably performed. Further, the CCD 161 as the image capture portion is provided in the reagent supply portion 150 of the pathological specimen preparation device 100, so that an image of the substrate W can be captured. Therefore, the tissue specimen Ts fixed to the substrate W or the information of the tissue specimen Ts written in the marking region 3 can be obtained as an image and managed. That is, it is possible to realize high traceability in association of the tissue specimen Ts with the pathological specimen preparation protocol (including the information of the reagent Rs, the washing solution Cs, and the like) in the step of preparing the pathological specimen.

Second Embodiment

<Pathological Specimen Preparation Device>

Next, an outline of a pathological specimen preparation device of a second embodiment will be described with reference to FIG. 29 and FIG. 30. FIG. 29 is a schematic perspective view showing an external appearance of the pathological specimen preparation device of the second embodiment, and FIG. 30 is a schematic perspective view showing a configuration of the pathological specimen preparation device 100 of the second embodiment. The pathological specimen preparation device of the second embodiment basically has the same configuration as that of the pathological specimen preparation device of the first embodiment, but is configured such that an improvement is made so as to enhance the operability when preparing a pathological specimen, the dischargeability of the reagent Rs or the washing solution Cs, the management of the residual amount of the reagent Rs in the cartridge, and the like. Incidentally, the same components as those of the pathological specimen preparation device 100 of the above-mentioned first embodiment are given the same reference numerals, and a detailed description thereof is omitted.

As shown in FIG. 29, a pathological specimen preparation device 200 of this embodiment has a main body portion 201 including an exterior cover 290 which covers the periphery. The exterior cover 290 has a front face plate 291 which is positioned in a front face lower part of the main body portion 201, and to which a power supply switch 202 is attached, a first opening/closing portion 293 which is positioned in a front face upper part, an upper face plate 294, and a pair of side face plates 296. The first opening/closing portion 293 is surrounded by the front face plate 291, the upper face plate 294, and the pair of side face plates 296 and openably and closably covers an opening portion 292.

In the front face plate 291, an opening 291a capable of setting or resetting the below-mentioned four tanks 205 to 208 is provided.

On one of the side face plates 296 in the pair, a second opening/closing portion 297 which opens and closes an opening portion capable of setting or resetting an upper electrode 20 of the below-mentioned electric field stirring portion 270 (see FIG. 30) is provided. Further, on the rear lower side of the pair of side face plates 296, a notched portion 296a is provided. According to this, the device is configured such that even if the main body portion 201 is, for example, disposed so as to be pressed against the wall face, a cord such as a power supply cord can be let out through the notched portion 296a. Incidentally, although not shown in FIG. 29, the exterior cover 290 has a rear face plate which covers the rear face on the upper side of the notched portion 296a.

The first opening/closing portion 293 of the exterior cover 290 is formed using, for example, a resin material such as ABS, and the front face plate 291, the upper face plate 294, the side face plates 296, and the rear face plate are formed using, for example, a steel plate to which plating, coating, or the like is applied. Further, in order to prevent the radiation of an unnecessary electromagnetic wave to the outside from the below-mentioned electric field stirring portion 270, circuit unit 280, high voltage generation portion 281 (see FIG. 30), or the like, it is preferred to provide an electro-magnetic shield that can shield an electromagnetic wave on the first opening/closing portion 293 made of a resin.

The pathological specimen preparation device 200 of this embodiment has a display portion 203 having a light transmissive T/K (touch key) as an input unit enabling an input operation to the device. The display portion 203 is, for example, a liquid crystal display device, and is attached to a pair of pivotable arm portions 295 provided on the upper face plate 294. According to this, the device is configured such that an operator can move the display portion 203 to an arbitrary position between the front side position overlapped with the first opening/closing portion 293 and the position above the upper face plate 294.

Also in this embodiment, the face on the side capable of facing the display portion 203 of the pathological specimen preparation device 200 is referred to as "front face", the right-left direction is referred to as "X direction", the front-rear direction is referred to as "Y direction", and the up-down direction is referred to as "Z direction" in the same manner as in the first embodiment, and a description will be given hereinbelow. Incidentally, the Y direction corresponds to the first direction of the invention, and the X direction corresponds to the second direction crossing the first direction of the invention.

As shown in FIG. 30, the pathological specimen preparation device 200 of this embodiment includes four tanks 205 to 208, a stage portion 210, a washing portion 230, a reagent supply portion 250, an electric field stirring portion 270, a circuit unit 280, a high voltage generation portion 281, and a frame 204 that is a structure body in which these respective portions are disposed. The frame 204 has a first frame 204a, a second frame 204b, a third frame 204c, and a fourth frame 204d, which are frames constituting a stage portion for disposing the above-mentioned respective portions, in this order from the lower side in the Z direction. The frame 204 is composed of, for example, aluminum.

On the first frame 204a which is the lowermost stage of the frame 204, the four tanks 205, 206, 207, and 208 are disposed in this order side by side in the X direction on the front side of the Y direction. In other words, a tank receiving portion capable of disposing the four tanks 205 to 208 side by side in the X direction is attached to the first frame 204a.

In the tank 205, a washing solution which is a buffer solution for preventing the tissue specimen Ts from drying or the like and for example, phosphate-buffered saline (PBS), Tris-buffered saline (TBS), standard saline citrate (SSC), or the like is stored. In the tank 206, pure water ($H_2O$) is stored as another washing solution. The tanks 205 and 206 are one example of the washing solution tank in the invention.

The tank 207 and the tank 208 are provided for storing the waste liquids of the washing solution Cs and the reagent Rs. The tanks 207 and 208 are one example of the waste liquid tank (a first waste liquid tank and a second waste liquid tank) in the invention. The volume of each of the tanks 205, 206, and 208 is, for example, 3 L (liters), and the volume of the tank 207 is, for example, 5 L, which is about twice as large as the volume of the other tanks. As the tanks 205 to 208, in consideration of chemical resistance, weight, or the like, for example, resin containers made of polyethylene, polypropylene, or the like are used.

As described in the above-mentioned first embodiment, there is a reagent Rs containing a substance (color developing agent) having carcinogenicity such as a color developing reagent, and when it is mixed with other liquids, the amount of the waste liquid required to be subjected to a predetermined waste liquid treatment is increased. Therefore, also in this embodiment, the device is configured to separately provide the tank 207 in which the waste liquid of the washing solution Cs and the waste liquid of the reagent Rs may be mixed and stored, and the tank 208 in which a waste liquid containing a color developing reagent is stored. Then, in this embodiment, the volume of the tank 207 is increased with respect to the four tanks 106 to 109 of the pathological specimen preparation device 100 of the above-mentioned first embodiment. This is configured such that even if the used amount of mainly the washing solution Cs, that is, the amount of the waste liquid is increased according to the type of the pathological specimen preparation protocol, the device can cope with the increase. Incidentally, the volumes of all the tanks 205 to 208 may be made the same or may be made different as needed. Further, the number of tanks for storing the washing solution Cs or the waste liquid is not limited to four.

Further, in this embodiment, a residual amount detection sensor 265 (not shown in FIG. 30) that detects the residual amount of each of various types of solutions (the washing solutions including pure water and the waste liquid) stored in the tanks 205 to 208 is provided corresponding to each of the tanks 205 to 208. As described above, in the case where the tanks 205 to 208 are constituted by using transparent or semi-transparent resin containers, as the residual amount detection sensor 265, a non-contact optical sensor can be used. The practical use of the residual amount detection sensor 265 will be described later.

On the rear side in the Y direction in the first frame 204a, the circuit unit 280 is disposed. The circuit unit 280 includes a power supply unit that supplies power to an electrical driving system included in the stage portion 210, the washing portion 230, and the reagent supply portion 250, a control unit associated with the control of the respective portions, and the like. The electrical configuration of the circuit unit 280 will be described in the below-mentioned pathological specimen preparation system. Incidentally, the high voltage generation portion 281 that supplies a high voltage to the electric field stirring portion 270 is attached to the fourth frame 204d on the upper side of the electric field stirring portion 270. By disposing the high voltage generation portion 281 near the electric field stirring portion 270 in this manner, the device is configured such that a wiring to which a high voltage is applied can be further shortened as compared with the above-mentioned first embodiment.

In the second frame 204b positioned above the first frame 204a in the Z direction, two pumps for sending out and supplying the washing solution Cs from the tank 205 or the tank 206, and a flow path switching mechanism 240 (see FIG. 37) for switching a discharge flow path for sorting and discharging the waste liquid of the washing solution Cs or the reagent Rs to the tank 207 or the tank 208 are disposed. The two pumps and the flow path switching mechanism 240 will be described later.

The stage portion 210 includes a stage 10R on which a substrate W is mounted, a stage transport mechanism that moves the stage 10R in the Y direction, and a stage tilting mechanism that tilts the stage 10R in the X direction. In the third frame 204c, a plurality of (in this embodiment, six) stage portions 210 extending in the Y direction are arranged in parallel in the X direction. The stage transport mechanism and the stage tilting mechanism will be described in detail later. Incidentally, the number of stage portions 210 is not limited to six. The respective stage portions 210 are separately disposed with respect to the third frame 204c, and therefore can be subjected to maintenance separately.

The washing portion 230, the reagent supply portion 250, and the electric field stirring portion 270 are disposed in the third frame 204c in this order in the Y direction. The washing portion 230 has a plurality of (six) nozzles corresponding to the number of stages 10R, and is configured such that the washing solution Cs necessary for washing out of the two types of washing solutions Cs can be supplied to each of the plurality of stages 10R. Further, the washing portion 230 is connected to a gas supply unit, has a plurality of (six) nozzles corresponding to the number of stages 10R, and is configured such that a gas can be sprayed on each of the plurality of stages 10R from the nozzle. That is, the washing portion 230 has two nozzles with respect to one stage 10R, that is, 12 nozzles in total. The reagent supply portion 250 is configured such that the reagent Rs necessary for a reaction out of a plurality of types of reagents Rs can be supplied to each of the plurality of (six) stages 10R. The electric field stirring portion 270 has an upper electrode 20 of a pair of electrodes. The upper electrode 20 is disposed so as to extend in the X direction across the plurality of (six) stage portions 210.

Each stage portion 210 is configured such that the stage 10R is moved in the Y direction by the stage transport mechanism and is disposed corresponding to each of the washing portion 230, the reagent supply portion 250, and the electric field stirring portion 270.

According to such a pathological specimen preparation device 200, a pathological specimen can be prepared by disposing the six substrates W at the maximum on the stages 10R, respectively. Further, in the frame 204, the four tanks 205 to 208, the circuit unit 280, the stage portion 210, the washing portion 230, the reagent supply portion 250, the electric field stirring portion 270, and the high voltage generation portion 281 are disposed in a superimposed manner, and therefore, the pathological specimen preparation device 200 which has a small footprint (mounting area) and is small in size is realized. Hereinafter, the configurations and structures of the respective portions in the pathological specimen preparation device 200 will be described. Incidentally, the frame 204 capable of disposing the respective portions in a superimposed manner in this manner is not limited to the four-stage configuration having the first frame 204a, the second frame 204b, the third frame 204c, and the fourth frame 204d, and may have a four- or more stage, for example, five-stage configuration.

<Stage Portion>

Next, the stage portion 210 will be described with reference to FIG. 31 to FIG. 33. FIG. 31 is a schematic perspective view showing a configuration of the stage portion of the second embodiment, FIG. 32 is a schematic perspective view showing the stage of the second embodiment, and FIG. 33 is a schematic perspective view showing the liquid discharge guide portion of the second embodiment.

As shown in FIG. 31, the stage portion 210 has the stage 10R, a support frame 211, a motor 215, a linear guide 217, a first stage support portion 221, a second stage support portion 223, a liquid discharge guide portion 226, and the like.

The support frame 211 has an upper face portion 211a extending in the Y direction, a pair of leg portions 211b and 211c which support the upper face portion 211a at both ends in the Y direction, and a side portion 211d which supports the upper face portion 211a at a middle position in the Y direction. The support frame 211 is configured such that the upper face portion 211a, the pair of leg portions 211b and 211c, and the side portion 211d are integrally formed by, for example, folding a SUS plate after performing contour machining. On a face on the lower side in the Z direction of the upper face portion 211a, the linear guide 217 is provided so as to extend in the Y direction.

The motor 215 is, for example, a stepping motor, and is attached to the leg portion 211c on one side positioned on the rear side in the Y direction of the pair of leg portions 211b and 211c so that a rotating shaft points upward in the Z direction. To the rotating shaft, a timing pulley 216b is attached. Another timing pulley 216a is pivotally supported in a rotatable manner by the leg portion 211b on the other side. A timing belt 218 is stretched over the two timing pulleys 216a and 216b. The first stage support portion 221 is fixed to a portion on the right side in the X direction of the stretched timing belt 218. When the motor 215 is driven, the timing belt 218 rotates, and the first stage support portion 221 fixed to the timing belt 218 can be moved to the front and rear sides in the Y direction.

The side portion 211d which supports the upper face portion 211a of the support frame 211 at a middle position in the Y direction is provided at a position closer to the leg portion 211b on the other side of the pair of leg portions 211b and 211c. The liquid discharge guide portion 226 is provided along the upper face portion 211a at a position where the side portion 211d is provided.

As shown in FIG. 32, the stage 10R is a substantially rectangular parallelepiped body and is disposed so that the longitudinal direction is parallel to the Y direction. The stage 10R has a mounting portion 11R on which the substrate W is mounted and a pedestal 12R which supports the mounting portion 11R from the lower side. The mounting portion 11R has a guide portion 11a and a guide portion 11b for mounting the substrate W at a predetermined position in the X direction and the Y direction. The guide portion 11a is provided on the right-side side in the X direction and a rear end side in the Y direction of the mounting portion 11R. The guide portion 11b is provided at the front left corner of the mounting portion 11R. On the left-side side in the X direction of the mounting portion 11R, a tilted portion 11d is provided, and on the guide portion 11a side of the tilted portion 11d, another guide portion 11e which is independent in an island shape is provided. The mounting portion 11R has a notched portion 11c in which the front right corner is notched, and also the pedestal 12R has a notched portion 12c in which the front right corner is notched similarly. These notched portions 11c and 12c are notched so that when the substrate W is set or reset with respect to the mounting portion 11R by grasping an end of the substrate W with, for example, forceps or the like, the forceps do not come into contact with the stage 10R. That is, it is configured such that setting or resetting of the substrate W with respect to the stage 10R can be easily performed. Incidentally, the mounting portion 11R functions as a lower electrode of a pair of electrodes in the below-mentioned electric field stirring portion 270, and is formed using, for example, aluminum. On the other hand, the pedestal 12R is formed using, for example, a resin or the like having an insulation property.

The pedestal 12R is formed so as to cut into in the X direction with a predetermined width, and has a pair of groove portions 12a opposed to each other in the Y direction. Further, two screw holes 12b and 12d are formed in the Y direction with respect to the pair of groove portions 12a. The pedestal 12R has an inclined plane 12e with a chamfered lower end on the right side in the X direction and a tilted portion 12f which is tilted projecting to the outside from the lower end on the opposite side in the X direction to the inclined plane 12e.

As shown in FIG. 31, the stage 10R is supported rotatably in a given direction from a horizontal state by the second stage support portion 223. More specifically, a pair of arm portions 223a and 223b of the second stage support portion 223 is inserted in the pair of groove portions 12a of the pedestal 12R. On the tip side of each of the arm portions 223a and 223b of the pair, a hole corresponding to each of the screw holes 12b and 12d provided in the pedestal 12R is formed. By inserting a shaft into each of the screw holes 12b and 12d, and allowing the shaft to pass through the holes formed in the pair of arm portions 223a and 223b, the pedestal 12R is supported by the second stage support portion 223 in a state of being rotatable around the shaft. In the above-mentioned first embodiment, the stage 10 is supported in a rotatable state on the side face on the outer side in the Y direction of the stage 10, however, in this embodiment, the stage 10R is supported rotatably by inserting the pair of arm portions 223a and 223b of the second stage support portion 223 in the pair of groove portions 12a of the pedestal 12R. According to this, the notched portion 11c of the mounting portion 11R and the notched portion 12c of the pedestal 12R described above can be made larger than the notched portion 13 of the stage 10 of the first embodiment described above. Therefore, the workability of setting or resetting of the substrate W with respect to the stage 10R is further improved.

The linear guide 217 is provided directly under the upper face portion 211a of the support frame 211. To the linear guide 217, a slider 217a (see FIG. 34) is attached. Further, the slider 217a is fixed to the second stage support portion 223. Further, the second stage support portion 223 is fixed to the first stage support portion 221 attached to the timing belt 218. That is, it is configured such that when the timing belt 218 is moved by driving the motor 215, the stage 10R supported by the first stage support portion 221 and the second stage support portion 223 can be moved in the Y direction along the linear guide 217. That is, the stage transport mechanism in this embodiment includes at least the motor 215 serving as a driving source, the timing pulleys 216a and 216b, the linear guide 217, the slider 217a, the timing belt 218, the first stage support portion 221, and the second stage support portion 223.

Incidentally, a sensor 228 is attached on the front side in the Y direction of the upper face portion 211a of the support frame 211. The sensor 228 plays a role in detecting the position of the first stage support portion 221 which is fixed to the timing belt 218 and moves in the Y direction, and stopping the motor 215. The position of the stage 10R when the sensor 228 stops the motor 215 is the starting point in the Y direction. When the stage 10R is positioned at the starting point, setting or resetting of the substrate W with respect to the stage 10R is performed.

As shown in FIG. 33, the liquid discharge guide portion 226 of this embodiment is a gutter having a substantially pentagonal contour similar to a baseball home base when viewed from the X direction, and a flexible tube is attached to a connection portion 227 protruding toward the lower end thereof. Further, the liquid discharge guide portion 226 has a protruding portion 226d protruding in the X direction and capable of screwing to the upper face portion 211a of the support frame 211. The protruding portion 226d is provided with a guide portion 226b whose shape including the side face portion 226a is an L shape when viewed from the Y direction. The edge of the guide portion 226b extends upward in the Z direction from the protruding portion 226d. The length L2 in the Y direction of the guide portion 226b is longer than the length L1 (see FIG. 32) in the Y direction of the stage 10R. The position where the liquid discharge guide portion 226 is attached to the upper face portion 211a of the support frame 211 corresponds to the washing position in the Y direction. That is, it is configured such that even if the substrate W mounted on the stage 10R is washed with the washing solution Cs at the washing position by moving the stage 10R back and forth in the Y direction, the washing solution Cs discharged from the top of the stage 10R can be received by the liquid discharge guide portion 226.

Next, the stage tilting mechanism of this embodiment will be described with reference to FIG. 34 and FIG. 35. FIG. 34 is a schematic perspective view illustrating the stage tilting mechanism of the second embodiment and FIG. 35 is a view showing a positional relationship between the tilted stage and the other configuration of the second embodiment. Incidentally, FIG. 35 is a view when viewing the tilted stage 10R from the Y direction.

As shown in FIG. 34, on the side portion 211d of the support frame 211, a wall face 211e which is vertically provided on the lower side of the timing belt 218, a flat plate 214 which is in contact with the wall face 211e and extends in the Y direction, and a pair of tilted portions 211f and 211g which are tilted in mutually different directions on the front side and the rear side in the Y direction of the wall face 211e are provided. Further, on the wall face 211e, a pair of guide plates 214a and 214b which face the pair of tilted portions 211f and 211g is provided on the front side and the rear side in the Y direction of the flat plate 214. Each of the guide plates 214a and 214b of the pair is supported by the wall face 211e in a state of being rotatable with the flat plate 214 side as a fulcrum.

The tip on the front side of the guide plate 214a on one side on the front side in the Y direction of the pair of guide plates 214a and 214b is biased upward in the Z direction by a spring 211h stretched between the guide plate 214a and the wall face 211e. The tip on the rear side of the guide plate 214b on the other side is biased downward in the Z direction by a spring 211i stretched between the guide plate 214b and the wall face 211e. Therefore, in a state of being biased by each of the springs 211h and 211i, the guide plate 214a on one side is tilted in a nearly horizontal state and is continuous with the flat plate 214. The guide plate 214b on the other side is continuous with the flat plate 214 in a state of being tilted to the rear side in the Y direction.

A lever 222 is pivotally supported in a rotatable manner by the first stage support portion 221 attached to the timing belt 218. The lever 222 has a first arm 222a extending downward in the Z direction and a second arm 222b extending upward after extending in the Y direction continuous with the first arm 222a, and has a substantially T-shaped contour when viewed from the X direction. To a tip portion 222c of the first arm 222a, a rod is attached in a rotatable state through a miniature bearing. Similarly, also to a tip portion 222d on the upper side of the second arm 222b, a rod is attached in a rotatable state.

An end portion 222e of a portion extending in the Y direction in the second arm 222b of the lever 222 is pivotally supported with respect to the first stage support portion 221. Therefore, as shown in FIG. 31, for example, when the stage 10R is positioned at the starting point in the Y direction, by bringing the portion extending in the Y direction of the second arm 222b into contact with a screw 221a fixed to the first stage support portion 221, the lever 222 is in a state where the rotation thereof around the end portion 222e is stopped. At this time, the tip portion 222d on the upper side of the second arm 222b of the lever 222 is in contact with the bottom face of the pedestal 12R of the stage 10R. When the motor 215 is driven from this state and the stage 10R is moved from the starting point to the rear side in the Y direction, the tip portion 222c of the first arm 222a of the lever 222 passes through the lower side of the guide plate 214a and the flat plate 214, flips up the guide plate 214b on the rear side, and moves to the motor 215 side.

When the stage 10R having moved to the rear side in the Y direction is moved to the front side toward the starting point again by driving and controlling the rotation of the motor 215, the tip portion 222c of the first arm 222a of the lever 222 is guided to the tilted portion 211g, comes into contact with the guide plate 214b on the rear side, and rides on the flat plate 214. According to this, the lever 222 pivots counterclockwise around the end portion 222e, and the tip portion 222d of the second arm 222b pushes up the bottom face of the pedestal 12R. The stage 10R in which the bottom face of the pedestal 12R is pushed up is tilted to the liquid discharge guide portion 226 in the X direction.

Further, when the stage 10R is moved toward the starting point, the tip portion 222c of the first arm 222a of the lever 222 comes into contact with the tilted portion 211f on the front side from the flat plate 214 and pushes down the guide plate 214a on the front side. In that case, the tip portion 222c of the first arm 222a comes off from the guide plate 214a and moves to the front side, and therefore, the lever 222 rotates clockwise around the end portion 222e and comes into contact with the screw 221a of the first stage support portion 221, and the rotation thereof is stopped. According to this, the action of pushing up the bottom face of the pedestal 12R by the tip portion 222d on the upper side of the second arm 222b of the lever 222 is released. In a hole 12g provided in the bottom face of the pedestal 12R, a locking portion 12h is fitted, and between the locking portion 12h and the second stage support portion 223, a spring 223d is stretched. The second stage support portion 223 has a contact portion 223e vertically provided in the Z direction below the pedestal 12R. When the action of pushing up the bottom face of the pedestal 12R by the tip portion 222d on the upper side of the second arm 222b of the lever 222 is released, the pedestal 12R is drawn by the stretched spring 223d and comes into contact with the contact portion 223e. According to this, the rotation of the stage 10R supported by the second stage support portion 222 is stopped, and the mounting portion 11R of the stage 10R is brought into a horizontal state.

That is, the stage tilting mechanism of this embodiment that tilts the stage 10R to the liquid discharge guide portion 226 side in the X direction includes the pair of tilted portions 211f and 211g, the flat plate 214, the pair of guide plates 214a and 214b, the first stage support portion 221, and the lever 222. The flat plate 214, the pair of guide plates 214a and 214b, the pair of tilted portions 211f and 211g, the first stage support portion 221, and the lever 222 are one example of the support mechanism in the stage tilting mechanism of the invention.

Incidentally, the sensor 228 is attached to the front side in the Y direction of the upper face portion 211a of the support frame 211. Further, a detection plate 221b is attached to the end portion 222e of the lever 222 pivotally supported by the first stage support portion 221. The sensor 228 is of a portal type, and it is configured such that by inserting the detection plate 221b into a portal-type detection portion with the movement of the first stage support portion 221 in the Y direction, the starting point of the stage 10R is detected by the sensor 228.

As shown in FIG. 35, by the stage tilting mechanism of this embodiment, the stage 10R is tilted to the liquid discharge guide portion 226 side. Further, the stage 10R is tilted so that the above-mentioned tilted portion 12f of the pedestal 12R is stopped in a state of being in contact with the guide portion 226b of the liquid discharge guide portion 226 or just before the tilted portion 12f comes into contact with the guide portion 226b. The tilt angle of the stage 10R at this time is an angle formed by the tilted substrate W mounted on the stage 10R and the horizontal plane and is set within the range of 45° to 60°. More specifically, by adjusting the attaching position of the flat plate 214 on the wall face 211e of the side portion 211d, and the shape of the lever 222 (that is, the length from the end portion 222e of the lever 222 to the tip portion 222c of the first arm 222a, and the length from the end portion 222e of the lever 222 to the tip portion 222d of the second arm 222b) shown in FIG. 34, the tilt angle of the stage 10R can be adjusted.

By tilting the stage 10R as described above, when the washing solution Cs is ejected to the substrate W from a nozzle 231 positioned above the stage 10R, the washing solution Cs moves along the surface of the substrate W and flows down within the guide portion 226b of the liquid discharge guide portion 226. Further, even if the washing solution Cs goes around the mounting portion 11R and flows on the side face of the pedestal 12R, the washing solution Cs moves along the tilted portion 12f provided in the pedestal 12R and flows down within the guide portion 226b. Further, in this embodiment, it is configured such that another nozzle 234 is disposed above the stage 10R, and air is sprayed onto the substrate W from the nozzle 234. Therefore, by spraying air on the surface of the tilted substrate W from the nozzle 234, the washing solution Cs ejected from the nozzle 231 can be completely discharged to the liquid discharge guide portion 226.

In this embodiment, not only is the stage 10 tilted as in the first embodiment, but also the nozzle 234 which ejects a gas (air) to the stage 10R is provided, and therefore, even if the tilt angle of the stage 10R is smaller than 60°, the washing solution Cs can be reliably discharged from the top of the substrate W. Hereinafter, a configuration of the washing portion 230 having the nozzle 231 and the nozzle 234 will be described in detail.

<Washing Portion>

The washing portion 230 of this embodiment will be described with reference to FIG. 36 to FIG. 40. FIG. 36 is a schematic perspective view showing a configuration of the washing portion of the second embodiment, FIG. 37 is a schematic perspective view showing a configuration of the flow path switching mechanism of the second embodiment, and FIG. 38 to FIG. 40 are each a piping system diagram showing a way of supplying the washing solution in the second embodiment.

As shown in FIG. 36, the washing portion 230 has a plurality of (six) nozzles 231 for ejecting the washing solution Cs, a plurality of (six) nozzles 234 for spraying air, a valve group 232 and a valve group 233, each including a plurality of valves, and a support plate 204e which supports the plurality of nozzles 231 and the plurality of nozzles 234.

The support plate 204e has a rectangular shape and is supported by the third frame 204c in the frame 204 of the pathological specimen preparation device 200 described above such that the long side direction is parallel to the X direction (see FIG. 30). In the support plate 204e, the plurality of nozzles 231 and the plurality of nozzles 234 are disposed at equal intervals in the X direction. The plurality of nozzles 231 are given reference numerals in the order from the right side in the X direction and called nozzles 231a, 231b, 231c, 231d, 231e, and 231f. Similarly, the plurality of nozzles 234 are given reference numerals in the order from the right side in the X direction and called nozzles 234a, 234b, 234c, 234d, 234e, and 234f. These nozzles 231 and 234 are provided in accordance with the respective stages 10R of the stage portions 210. In the X direction, the nozzles 234 are disposed so as to be slightly shifted to the left side with respect to the nozzles 231.

The valve group 232 and the valve group 233 include a plurality of valves provided in accordance with the number of nozzles 231. The valve group 232 has a plurality of (six) valves 232a, 232b, 232c, 232d, 232e, and 232f arranged in the Y direction. The valve group 233 also has a plurality of (six) valves 233a, 233b, 233c, 233d, 233e, and 233f arranged in the Y direction. The valve group 232 and the valve group 233 are disposed separately in the third frame 204c of the pathological specimen preparation device 200 so as to face each other with the support plate 204e interposed therebetween (see FIG. 30).

The valve group 232 and the valve group 233 are electromagnetic valves whose opening and closing can be electrically controlled, and the opening and closing are controlled by a control unit included in the below-mentioned circuit unit 280. More specifically, the electromagnetic valve has a portal-type opening and closing portion, and by lowering the opening and closing portion so as to press and squash a flexible tube inserted into the opening and closing portion, a liquid flow path in the tube can be closed. When the pressing of the tube is released by lifting the opening and closing portion, the liquid flow path in the tube can be opened.

For example, as shown by the solid line in FIG. 36, a flexible tube is connected to the nozzle 231a through the valve 232a and the valve 232b. Similarly, a flexible tube is connected to the nozzle 231b through the valve 232c and the valve 232d. Similarly, a flexible tube is connected to the nozzle 231c through the valve 232e and the valve 232f. Similarly, a flexible tube is connected to the nozzle 231f through the valve 233a and the valve 233b. Similarly, a flexible tube is connected to the nozzle 231e through the valve 233c and the valve 233d. Similarly, a flexible tube is connected to the nozzle 231d through the valve 233e and the valve 233f. By achieving connection in this manner, the length of the flexible tube from the valve to the nozzle 231 can be made substantially the same for each nozzle 231. That is, the pressure loss when supplying the washing solution Cs to the respective nozzles 231 is equalized for each nozzle 231, and thus, a variation in the supply amount of the washing solution Cs can be suppressed.

To a piping system associated with the valves 232a, 232c, and 232e, and the valves 233a, 233c, and 233e, pure water (H$_2$O) as the other washing solution Cs is supplied, and to a piping system associated with the valves 232b, 232d, and 232f, and the valves 233b, 233d, and 233f, the washing solution Cs is supplied. By controlling the opening and closing of each valve, two types of washing solutions Cs can be ejected from each of the plurality of nozzles 231a, 231b, 231c, 231d, 231e, and 231f. A detailed method of supplying the washing solution Cs will be described later.

Each of the other plurality of nozzles 234a, 234b, 234c, 234d, 234e, and 234f supported by the support plate 204e is connected to a gas supply unit through a valve 235. As the gas supply unit in this embodiment, for example, a small-sized pressure pump capable of compressing and sending air is exemplified. The valve 235 is also an electromagnetic valve, and the opening and closing thereof are controlled by a control unit provided in the circuit unit 280.

The washing portion 230 has a flow path switching mechanism for discharging the washing solution Cs ejected from the nozzle 231 to either the tank 207 or the tank 208 as a waste liquid.

As shown in FIG. 37, the flow path switching mechanism 240 of this embodiment is configured to include a pair of leg portions 241a and 241b, a waste liquid receiving portion 242, a motor 245, and a branch flow path 246.

The pair of leg portions 241a and 241b is attached to the third frame 204c of the frame 204 described above so as to face each other in the X direction. The waste liquid receiving portion 242 has a long and narrow gutter-like shape and is disposed along the X direction by being supported on the both end sides of an opening so that the opening becomes horizontal by the pair of leg portions 241a and 241b.

Although not shown in FIG. 37, in the waste liquid receiving portion 242 having a gutter-like shape, the tip of the tube attached to the connection portion 227 of the liquid discharge guide portion 226 provided in each of the plurality of stage portions 210 described above hangs down.

The waste liquid receiving portion 242 having a gutter-like shape is formed such that the depth and the width on the right side in the X direction are deeper and wider than on the left side. A discharge port 242a is provided directed downward in the Z direction in a bottom portion on the right side in the X direction of the waste liquid receiving portion 242. To the discharge port 242a, a flexible tube 243 is attached.

The branch flow path 246 is disposed on the lower side of the discharge port 242a in the Z direction. The branch flow path 246 also has a gutter-like shape and is provided with openings (illustration is omitted in FIG. 37) on both ends in the X direction in a bottom portion. Further, in the bottom portion of the branch flow path 246, inclined planes inclined toward the respective two openings are provided. The inclined plane portion of the branch flow path 246 is supported by a side portion 241c from the lower side.

The side portion 241c that supports the branch flow path 246 from the lower side has a wall face vertically provided in the Z direction, and the motor 245 is attached to the wall face so that the rotating shaft is parallel to the Y direction. The motor 245 is, for example, a stepping motor, and to the rotating shaft of the motor 245, a tube holder 244 that holds the tip side of the tube 243 extending downward in the Z direction in the branch flow path 246 is attached. While the motor 245 is stopped, the tip of the tube 243 held by the tube holder 244 is positioned at the boundary between the two inclined planes in the bottom portion of the branch flow path 246.

The opening on one side on the left side in the X direction of the two openings provided in the bottom portion of the branch flow path 246 is positioned above an inlet port 207a of the tank 207. The opening on the other side on the right side in the X direction of the two openings is positioned above an inlet port 208a of the tank 208. Although illustration is omitted in FIG. 37, the tube connected to one of the two openings is inserted into the inlet port 207a of the tank 207, and the tube connected to the other opening is inserted into the inlet port 208a of the tank 208.

As described above, when the washing solution Cs is ejected from the nozzle 231 to the substrate W mounted on the stage 10R in a state where the stage 10R is tilted by the stage tilting mechanism at the washing position, the washing solution Cs flows in the liquid discharge guide portion 226 after washing the surface of the substrate W. The washing solution Cs flowing in the liquid discharge guide portion 226 flows in the waste liquid receiving portion 242 having a gutter-like shape through the tube attached to the connection portion 227. The washing solution Cs flowing in the waste liquid receiving portion 242 flows to the right side in the X direction in the bottom portion and reaches the discharge port 242a. At this time, for example, when the motor 245 is driven so as to rotate the rotating shaft clockwise at a predetermined angle in FIG. 37, the tube 243 attached to the discharge port 242a is directed to the left side in the X direction, and the washing solution Cs flowing in the discharge port 242a is guided to the tank 207 from the opening on one side on the left side in the X direction of the branch flow path 246 and discharged as a waste liquid.

Further, for example, when the motor 245 is driven so as to rotate the rotating shaft counterclockwise at a predetermined angle in FIG. 37, the tube 243 attached to the discharge port 242a is directed to the right side in the X direction, and the washing solution Cs flowing in the discharge port 242a is guided to the tank 208 from the opening on the other side on the right side in the X direction of the branch flow path 246 and discharged as a waste liquid.

The flow path switching mechanism 240 of this embodiment includes at least the waste liquid receiving portion 242, the motor 245, the tube holder 244 attached to the rotating shaft of the motor 245, and the branch flow path 246. According to this, for example, in the case where the washing solution Cs flowing in the waste liquid receiving portion 242 does not contain a color developing reagent, by driving the motor 245, the washing solution Cs (waste liquid) is discharged to the tank 207. Further, for example, in the case where the washing solution Cs flowing in the waste liquid receiving portion 242 contains a color developing reagent, by driving the motor 245, the washing solution Cs (waste liquid) is discharged to the tank 208.

As shown in FIG. 38, a system for supplying the washing solution Cs to the plurality of nozzles 231a, 231b, 231c, 231d, 231e, and 231f has a first supply system that pumps out the washing solution stored in the tank 205 by a pump P1 and sends the washing solution Cs to the nozzles 231a, 231b, and 231c through a pipe 237a and the valves 232b, 232d, and 232f, and a second supply system that sends the washing solution Cs to the nozzles 231d, 231e, and 231f through a pipe 237b and the valves 233b, 233d, and 233f. Further, the system has a third supply system that pumps out pure water ($H_2O$) stored in the tank 206 by a pump P2 and sends pure water to the nozzles 231a, 231b, and 231c through a pipe 238a and the valves 232a, 232c, and 232e, and a fourth supply system that sends pure water to the nozzles 231d, 231e, and 231f through a pipe 238b and the valves 233a, 233c, and 233e. Further, on the sending side of the pump P1, a valve 236a is provided. Further, in a pipe connecting the valve 236a on the sending side to the pump P2 on the sending side, a relay valve 236b is provided.

As shown in FIG. 38, when the valve 236b connected to the pump P2, and the valves 232a, 232c, and 232e and the valves 233a, 233c, and 233e are closed, and the valve 236a connected to the pump P1, and the valves 232b, 232d, and 232f and the valves 233b, 233d, and 233f are opened, and the pump P1 is driven, the washing solution Cs can be ejected from each of the plurality of nozzles 231a, 231b, 231c, 231d, 231e, and 231f.

Further, as shown in FIG. 39, when the relay valve 236b, the valves 232b, 232d, and 232f, and the valves 233b, 233d, and 233f are closed, and the valve 236a connected to the pump P1, and the valves 232a, 232c, and 232e and the valves 233a, 233c, and 233e are opened and the pump P2 is driven, pure water can be ejected from each of the plurality of nozzles 231a, 231b, 231c, 231d, 231e, and 231f. That is, an operation of ejecting the washing solution Cs or pure water from each of the plurality of nozzles 231a, 231b, 231c, 231d, 231e, and 231f is performed by opening and closing the valve attached to each of the plurality of nozzles 231a, 231b, 231c, 231d, 231e, and 231f.

In the case where a buffer solution such as PBS described above is used as the washing solution Cs, when the buffer solution in a pipe is dried and a solid component is deposited, the pipe may be closed. Therefore, it is preferred to periodically or appropriately wash the first supply system and the second supply system to which a buffer solution such as PBS is supplied with pure water. In such a case, as shown in FIG. 40, when the valve 236a connected to the pump P1, and the valves 232a, 232c, and 232e and the valves 233a, 233c, and 233e are closed, and the relay valve 236b, the valves 232b, 232d, and 232f, and the valves 233b, 233d, and 233f are opened and the pump P2 is driven, pure water is supplied to the first supply system and the second supply system to perform washing, and pure water after washing can be discharged from each of the plurality of nozzles 231a, 231b, 231c, 231d, 231e, and 231f. Pure water used for washing and discharged from the nozzles 231 is guided and discharged to the tank 207 having a larger volume than the other tanks by the above-mentioned flow path switching mechanism 240 from the liquid discharge guide portion 226.

In this embodiment, the piping system in which a buffer solution such as PBS is supplied to each of the plurality of nozzles 231a, 231b, 231c, 231d, 231e, and 231f is divided into the first supply system and the second supply system, and therefore, as compared with the case where a buffer solution is supplied to the plurality of nozzles 131 in one supply system as in the above-mentioned first embodiment, the buffer solution can be stably ejected from each nozzle 231. Further, the device is less likely to be affected by clogging of the piping system.

Incidentally, although not shown in FIG. 38 to FIG. 40, in this embodiment, in a pipe between the first supply system or the second supply system and the valve 236a, a pressure sensor that detects the pressure of the washing solution Cs passing through the pipe is provided. By detecting the pressure loss in the pipe with the pressure sensor, clogging of the first supply system and the second supply system is detected so as to be able to urge an operator to perform washing with pure water.

<Reagent Supply Portion>

Next, the reagent supply portion 250 of this embodiment will be described with reference to FIG. 41 to FIG. 44. FIG. 41 is a schematic perspective view showing a configuration of the reagent supply portion of the second embodiment, FIG. 42 is a perspective view showing the cartridge of the second embodiment, FIG. 43 is a schematic plan view showing the arrangement of the respective portions associated with the reagent supply portion of the second embodiment, and FIG. 44 is a schematic side view showing the arrangement of the respective portions associated with the reagent supply portion of the second embodiment.

The reagent supply portion 250 of this embodiment is a device that supplies the reagent Rs filled in a cartridge 50R to the substrate W mounted on the stage 10R of the stage portion 210. As shown in FIG. 41, the reagent supply portion 250 has a pier portion 251, a support frame 252, a front face frame 253, a pair of timing pulleys 254a and 254b, a plurality of cartridge holders 255 as holding portions capable of attaching and detaching the cartridge 50R, a timing belt 256, a motor 257, and an electric pusher 258.

The pier portion 251 is a structure body that supports the pair of timing pulleys 254a and 254b, and the motor 257, and is stretched over in the X direction in the third frame 204c of the pathological specimen preparation device 200. On the both end sides of a part extending in the X direction of the pier portion 251, the pair of timing pulleys 254a and 254b are provided. The timing pulley 254a on one side positioned on the right side in the X direction of the pair of timing pulleys 254a and 254b is pivotally supported in a rotatable manner by the pier portion 251. To the timing pulley 254b on the other side positioned on the left side in the X direction, the motor 257 is attached, and the rotation thereof is electrically controlled. The motor 257 is, for example, a stepping motor.

The timing belt 256 is stretched between the pair of timing pulleys 254a and 254b. To the timing belt 256, a plurality of (nine) cartridge holders 255 are attached. In this embodiment, two cartridges 50R can be attached to and detached from one cartridge holder 255, and therefore, it is configured such that a total of 18 cartridges 50R can be attached to the plurality of (nine) cartridge holders 255. By driving the motor 257 so as to move the timing belt 256, the plurality of (nine) cartridge holders 255 attached to the timing belt 256 can be moved freely in the X direction. In this embodiment, a configuration including the pair of timing pulleys 254a and 254b, the timing belt 256, and the motor 257 is one example of the transport portion of the invention.

The support frame 252 is provided so as to be erected on the rear end in the Y direction of the pier portion 251 and extend in the X direction. The support frame 252 has a shape extending in the Z direction after being bent in the middle to the rear side in the Y direction. In the bent portion of the support frame 252, a plurality of (six) electric pushers 258 are provided. The electric pusher 258 includes a motor 258a, a male screw 258b, and a support portion 258c for the male screw 258b. The motor 258a is, for example, a linear stepping motor, and screws with the male screw 258b and allows the male screw 258b to move up and down in the Z direction. According to this, the electric pusher 258 can pressurize the cartridge 50R attached to the cartridge holder 255 from the upper side to the lower side in the Z direction by the male screw 258b.

The support portion 258c that supports the male screw 258b on the upper end side in the Z direction is provided for each electric pusher 258 in the support frame 252, and is attached to the upper end of a slit 252a formed extending in the Z direction. According to this, it is configured such that shaft wobble by rotation of the male screw 258b is prevented by the support portion 258c.

The front face frame 253 which is erected on the front end in the Y direction of the pier portion 251 and extends in the X direction is provided. Three lamps 259 (259a, 259b, and 259c) are attached to a central portion in the X direction of the front face frame 253 at intervals. As the lamps 259, for example, LEDs capable of obtaining light emission of at least two colors (for example, green and red) are used. The arrangement of the three lamps 259 in the X direction is set in accordance with the arrangement of the cartridges 50R attached to the cartridge holders 255. It is configured such that the state of the residual amount of the reagent Rs in the cartridge 50R positioned at the front of the lamp 259 can be found based on the lighting state of the lamp 259 so that an operator is urged to replace the cartridge 50R as needed. For example, the lamp 259b at the center of the three lamps 259 becomes in a lighting state that indicates that the cartridge 50R should be replaced, and the cartridge 50R to be replaced is transported to the front of the lamp 259b at the center. According to this, the cartridge 50R to be replaced can be reliably replaced. Incidentally, as the lighting state that indicates that the cartridge 50R should be replaced, a state where the lamp 259b at the center lights up in a different color from that of the other lamps 259a and 259c, a state where the lamp 259b at the center flashes on and off and the other lamps 259a and 259c light up normally or do not light up, or the like is exemplified. The detection of the residual amount of the reagent Rs in the cartridge 50R will be described later.

Here, the cartridge 50R capable of ejecting the reagent Rs of this embodiment will be described with reference to FIG. 42. As shown in FIG. 42, the cartridge 50R has a first case 51 filled with the reagent Rs, a second case 52 capable of housing the first case 51 and having a cylindrical shape provided with a nozzle portion 52a on the bottom face, and a lid portion 53 of the first case 51. On the side closer to a housing port on a side face of the second case 52, an opening portion 52b having a rectangular shape is provided. Further, on the lower side in the Z direction of the side face provided with the opening portion 52b, two opening portions 52c and 52d are provided with a gap therebetween. On the side face of the first case 51 opposed to the opening portion 52b, a locking portion 51b is provided.

The first case 51 has a housing portion 51a capable of storing the reagent Rs. On the lower side in the Z direction of the housing portion 51a, a constricted portion 51c whose volume is throttled is formed. The constricted portion 51c has a valve structure that prevents the reagent Rs from leaking from the tip side of the constricted portion 51c. The reagent Rs is injected into the housing portion 51a from the housing port of the first case 51, and the first case 51 is covered with the lid portion 53. It is configured such that when the first case 51 is inserted and pushed in the second case 52 thereafter, the constricted portion 51c of the housing portion 51a and a communication portion 52e to be connected to the nozzle portion 52a of the second case 52 are connected to each other in a state of being able to move up and down in the Z direction. To the communication portion 52e, a coil spring (illustration is omitted) as a biasing unit that biases the first case 51 to the upper side in the Z direction is attached. Further, the locking portion 51b of the first case 51 is locked in the opening portion 52b of the second case 52, whereby the first case 51 is fitted in the second case 52. According to this, it is configured such that the first case 51 is in a state where it is difficult to easily detach the first case 51 from the second case 52, and water or the like hardly penetrates in the cartridge 50R from the outside. Incidentally, in the lid portion 53, a communication hole 53a that communicates with the housing portion 51a is provided.

It is configured such that when the lid portion 53 of the cartridge 50R is pressed so as to push down the first case 51 with respect to the second case 52, a predetermined amount of the reagent Rs can be ejected from the nozzle portion 52a through the communication portion 52e. It is configured such that the ejection amount of the reagent Rs to be ejected from the nozzle portion 52a by one pressing is determined by the volume of the reagent Rs filled in the communication portion 52e.

The first case 51 in which the reagent Rs of the cartridge 50R is stored is transparent or semi-transparent and also is composed of, for example, polypropylene or polyethylene in consideration of chemical resistance. On the side face of the second case 52 that houses the first case 51, the opening portions 52c and 52d are provided as described above. The opening portion 52c is provided at a position capable of facing a part near the constricted portion 51c of the housing portion 51a of the first case 51. The opening portion 52d is provided at a position capable of facing the constricted portion 51c of the first case 51.

A hook 55 is provided on a side face opposed to the side face on which the opening portions 52b, 52c, and 52d are provided in the cartridge 50R. Therefore, as shown in FIG. 41, when the cartridge 50R is inserted into the cartridge holder 255, a portion of the cartridge holder 255 becomes in a state of being sandwiched between the side face of the cartridge 50R and the hook 55, and therefore, the second case 52 can be fixed so as not to move by attaching the cartridge 50R to the cartridge holder 255. Incidentally, on the bottom face of the cartridge holder 255, an opening is provided at a position corresponding to the nozzle portion 52a.

As shown in FIG. 43, by driving the motor 257 and moving the timing belt 256 in the X direction, the cartridge 50R attached to the cartridge holder 255 can be moved to a position overlapped with the electric pusher 258. By the electric pusher 258, the lid portion 53 of the cartridge 50R is pressed, and the reagent Rs is ejected from the nozzle portion 52a of the cartridge 50R as described above. At this time, by moving the stage 10R to a position opposed to the reagent supply portion 250 by the stage portion 210 in advance, a predetermined amount of the reagent Rs can be accurately dropped onto the tissue specimen Ts on the substrate W mounted on the stage 10R.

Further, as shown in FIG. 43, a barcode reader 262 and a plurality of sensors are provided side by side on the rear side in the Y direction and on the left side in the X direction of the reagent supply portion 250. The plurality of sensors include two residual amount detection sensors 263 (263a and 263b) for detecting the residual amount of the reagent Rs in the cartridge 50R and a height detection sensor 268 for detecting the height of the cartridge 50R.

Further, an image capture unit 260 capable of capturing an image of the substrate W is provided on the front side in the Y direction of the reagent supply portion 250. The image capture unit 260 is configured to include a CCD 261 as an image capture portion, a pair of timing pulleys 264a and 264b, a timing belt 266, and a motor 267.

The pair of timing pulleys 264a and 264b is disposed side by side in the Y direction so as to be partially overlapped with the pair of timing pulleys 254a and 254b of the reagent supply portion 250 in a plan view. The timing belt 266 is stretched in the X direction over the pair of timing pulleys 264a and 264b. On the front side of the timing belt 266 stretched in the X direction, the CCD 261 is attached in a state of being able to capture an image on the lower side in the Z direction. The motor 267 is attached to the timing pulley 264b on the left side in the X direction of the pair of timing pulleys 264a and 264b.

By driving the motor 267, the CCD 261 fixed to the timing belt 266 can be moved in the X direction. That is, by driving and controlling the motor 267, the CCD 261 can be disposed freely at a position corresponding to the stage 10R moved to the reagent supply portion 250 by the stage transport mechanism in each of the above-mentioned plurality of (six) stage portions 210. Then, by capturing an image of the substrate W mounted on the stage 10R using the CCD 261, the state of the tissue specimen Ts fixed to the substrate W or the information related to the tissue specimen Ts written in the marking region 3 can be obtained as an image.

Next, the respective configurations of the barcode reader 262 and the plurality of sensors associated with the cartridge 50R will be described with reference to FIG. 44.

As shown in FIG. 44, a leg portion 251b is vertically provided on the rear side in the Y direction with respect to the pier portion 251 that supports the pair of timing pulleys 254a and 254b of the reagent supply portion 250 from the lower side. The height of the leg portion 251b is set so as not to come into contact with the cartridge holder 255. A support portion 251c extending to the rear side in the Y direction from the head of the leg portion 251b is provided, and the barcode reader 262 and a plurality of sensors are provided on the support portion 251c. As for the plurality of sensors, the height detection sensor 268, the residual amount detection sensor 263a, and the residual amount detection sensor 263b are attached sequentially from the top to a support plate 251d which is provided on the support portion 251c and extends in the Z direction.

In this embodiment, a sticker indicating a barcode associated with the reagent Rs is adhered to the side face between the opening portion 52c and the opening portion 52d of the second case 52 of the cartridge 50R.

When the motor 257 is driven so as to move the cartridge holder 255, the cartridge 50R can be opposed to the barcode reader 262. By the barcode reader 262, the barcode adhered to the cartridge 50R can be read. Incidentally, the action of reading the barcode using the barcode reader 262 is performed for each of the 18 cartridges 50R in total set in the plurality of cartridge holders 255 of the reagent supply portion 250. The barcode to be given to the cartridge 50R is a one-dimensional barcode or a two-dimensional barcode, and as the barcode reader 262, a device which can read these barcodes is selected.

The position where the barcode is given in the cartridge 50R is not limited to the side face between the opening portion 52c and the opening portion 52d of the second case 52. The position of the barcode reader 262 may be set so that the cartridge 50R and the barcode reader 262 are opposed to each other in accordance with the position where the barcode is given.

Further, when the motor 257 is driven so as to move the cartridge holder 255, the cartridge 50R can be opposed to the two residual amount detection sensors 263a and 263b and the height detection sensor 268. Incidentally, the cartridge 50R opposed to the plurality of sensors is the cartridge 50R capable of ejecting the reagent Rs by the electric pusher 258 (see FIG. 43).

The residual amount detection sensor 263a of the two residual amount detection sensors 263a and 263b is attached to the support plate 251d at a position capable of facing the opening portion 52c of the second case 52 of the cartridge 50R. Further, the residual amount detection sensor 263b is attached to the support plate 251d at a position capable of facing the opening portion 52d of the second case 52 of the cartridge 50R.

Each of the two residual amount detection sensors 263a and 263b includes a light emitting portion and a light receiving portion, and optically detects the presence or absence of the reagent Rs by receiving reflection light obtained by reflecting emission light emitted from the light emitting portion from a target material by the light receiving portion and detecting the intensity of the reflection light.

As described above, the first case 51 filled with the reagent Rs in the cartridge 50R is formed using a transparent or semi-transparent light transmissive member. Therefore, by using the residual amount detection sensor 263a, the presence or absence of the reagent Rs in the housing portion 51a of the first case 51 can be detected. Further, when using the residual amount detection sensor 263b, the presence or absence of the reagent Rs in the constricted portion 51c of the first case 51 can be detected.

The opening portion 52c of the cartridge 50R facing the residual amount detection sensor 263a opens to the housing portion 51a on the side closer to the constricted portion 51c, and therefore, in the case where it is detected that the reagent Rs is not present by the residual amount detection sensor 263a, it is indicated that the amount of the reagent Rs in the housing portion 51a is significantly decreased, and the time for replacement of the reagent cartridge 50R is near at hand.

The opening portion 52d of the cartridge 50R facing the residual amount detection sensor 263b opens to the constricted portion 51c, and therefore, in the case where it is detected that the reagent Rs is not present by the residual amount detection sensor 263b, it is indicated that the amount of the reagent Rs reaches the limit and the cartridge 50R needs to be replaced. By using the two residual amount detection sensors 263a and 263b in this manner, the residual amount of the reagent Rs in the cartridge 50R is accurately detected, and thus, the management of the residual amount of the reagent Rs can be ensured.

The height detection sensor 268 is attached to the support plate 251d at a position capable of detecting the upper face of the lid portion 53 of the cartridge 50R set in the cartridge holder 255. As described above, the cartridge 50R is configured such that a predetermined amount of the reagent Rs can be ejected from the nozzle portion 52a by pressing the lid portion 53 from the upper part by the electric pusher 258. When the cartridge 50R is not properly set in the cartridge holder 255 and the lid portion 53 is disposed on the upper side of the predetermined position in the Z direction, even if the lid portion 53 is pressed once by the electric pusher 258, a predetermined amount of the reagent Rs may not be accurately ejected from the nozzle portion 52a. Further, when the motor 257 is driven so as to move the cartridge holder 255, the male screw 258b of the electric pusher 258 and the lid portion 53 of the cartridge 50R may come into contact with each other. It is configured such that by detecting the position of the lid portion 53 of the cartridge 50R, that is, the height of the cartridge 50R set in the cartridge holder 255 using the height detection sensor 268, the above-mentioned problem can be prevented.

Incidentally, as shown in FIG. 44, the CCD 261 of the image capture unit 260 is disposed on the front side in the Y direction with respect to the motor 267 that moves the CCD 261 in the X direction. Further, a plurality of (four) lighting elements 261a are provided at positions (actually, four corners) surrounding the CCD 261. The lighting element 261a is, for example, an LED and is provided for lighting the substrate W which is an image capture target whose image is to be captured by the CCD 261. The number of lighting elements 261a is not limited to the plural number (four), and may be at least one.

<Electric Field Stirring Portion>

Next, the electric field stirring portion 270 will be described with reference to FIG. 45. FIG. 45 is a schematic perspective view showing a configuration of the electric field stirring portion of the second embodiment.

As shown in FIG. 45, the electric field stirring portion 270 has an upper electrode 20, a support frame 271, and a pair of leg portions 272a and 272b. The upper electrode 20 has a rectangular shape in which one side portion is longer than the other side portion. The support frame 271 is provided for stretching the long and narrow upper electrode 20 in the X direction in the third frame 204c of the pathological specimen preparation device 200 (see FIG. 30). The support frame 271 is fixed to the pair of leg portions 272a and 272b opposed to each other with a gap therebetween in the X direction, and has guide portions 271a and 271b disposed with a gap therebetween in the Y direction. The guide portion 271a is longer than the guide portion 271b, and each of the guide portions 271a and 271b is configured to have a groove capable of inserting the upper electrode 20 therein from the right side in the X direction. On the left end of the guide portion 271a, a support plate 273 is stretched over in the Y direction, and on the support plate 273, a microswitch 275 is provided. The microswitch 275 is provided for detecting whether the left end in the X direction of the upper electrode 20 is disposed at a predetermined position when the upper electrode 20 is inserted along the guide portion 271a. That is, the plate-shaped upper electrode 20 can be attached at a predetermined position and also can be inserted and removed with respect to the support frame 271.

On the lower face in the Z direction of the upper electrode 20, a plurality of grooves 21 extending in the Y direction are formed. The plurality of grooves 21 are formed at equal intervals in the X direction. When the stage 10R is moved to the electric field stirring portion 270 by the above-mentioned stage transport mechanism, the mounting portion 11R that functions as the lower electrode of the stage 10R and the upper electrode 20 are opposed to each other. Further, by detecting the position of the left end in the X direction of the upper electrode 20 with the above-mentioned microswitch 275, the upper electrode 20 is disposed so that the mounting portion 11R and the groove 21 are opposed to each other. A method in which the stage 10R and the upper electrode 20 are disposed to generate an electric field between the pair of electrodes thereby stirring a liquid droplet S on the substrate W mounted on the stage 10R by the electric field in this manner is the same as the method described in the above-mentioned first embodiment. Therefore, a detailed description of electric field stirring is omitted. Incidentally, also in this embodiment, it is configured such that unless the upper electrode 20 comes into contact with the microswitch 275 and is brought into an on state, an electric field is not generated between the mounting portion 11R that functions as the lower electrode of the stage 10R and the upper electrode 20.

<Pathological Specimen Preparation System>

Next, a pathological specimen preparation system of a second embodiment will be described with reference to FIG. 46. FIG. 46 is a block diagram showing an electrical and mechanical configuration of the pathological specimen preparation system of the second embodiment. The pathological specimen preparation system of the second embodiment adopts the pathological specimen preparation device 200 of the second embodiment and incorporates the characteristics thereof in contrast to the pathological specimen preparation system 1000 of the above-mentioned first embodiment. Therefore, the same components as those of the pathological specimen preparation system 1000 are given the same reference numerals, and a detailed description thereof is omitted.

As shown in FIG. 46, a pathological specimen preparation system 2000 of this embodiment includes the pathological specimen preparation device 200, for example, a desktop computer 500, and peripheral devices connected to the computer 500.

The pathological specimen preparation device 200 has the display portion 203, the stage portion 210, the washing portion 230, the reagent supply portion 250, the electric field stirring portion 270, the circuit unit 280, and the high voltage generation portion 281 as described above. Further, the pathological specimen preparation device 200 includes the CCD 261 as the image capture portion, the barcode reader 262, and various types of sensors such as the residual amount detection sensors 263 (263a and 263b) for the cartridge 50R, the residual amount detection sensors 265 associated with the tanks 205 to 208, and the height detection sensor 268. The circuit unit 280 includes a motor driver 282, a Peltier controller 283, a control unit 285, a DC power supply unit 286, and a USB hub 287. The high voltage generation portion 281 is a device that generates a potential which periodically changes as described above and applies the potential to the pair of electrodes 11R and 20 of the electric field stirring portion 270.

The motor driver 282 of the circuit unit 280 is a circuit board on which a circuit that drives and controls a motor included in each of the stage portion 210, the washing portion 230 (including the flow path switching mechanism 240), the reagent supply portion 250, and the image capture unit 260 is mounted. To the stage 10R of the stage portion 210, the Peltier element 15 as a heating element for heating the stage 10R and a temperature sensor 16 that detects the temperature of the stage 10R are attached. The Peltier controller 283 and the temperature sensor 16 are connected to the control unit 285 through, for example, an I/O port. The Peltier controller 283 controls the temperature of the Peltier element 15 by controlling an electric current flowing in the Peltier element 15 based on a control signal from the control unit 285. Incidentally, the Peltier controller 283 of this embodiment includes a microcomputer associated with the control of the temperature of the Peltier element 15, however, the microcomputer may be configured to be included in the control unit 285.

The various types of sensors such as the residual amount detection sensors 263 and 265 are also connected to the control unit 285 through, for example, an I/O port.

The CCD 261 and the barcode reader 262 are connected to the control unit 285 through the USB hub 287. The CCD 261 is provided so as to be able to capture an image of the substrate W mounted on the stage 10R as described above. The control unit 285 can obtain the information of the tissue specimen Ts fixed to the substrate W from the information of the image of the substrate W captured by the CCD 261.

The barcode reader 262 is provided so as to be able to read a barcode given to the cartridge 50R mounted on the reagent supply portion 250 as described above. The control unit 285 can obtain the information of the reagent Rs filled in the cartridge 50R from the barcode read by the barcode reader 262.

The circuit unit 280 includes at least the motor driver 282, the Peltier controller 283, the control unit 285, the DC power supply unit 286, and the USB hub 287. The DC power supply unit 286 generates a DC voltage required as a power supply for the respective portions of the circuit unit 280 and the high voltage generation portion 281 from an AC power supply of 100 V supplied from the outside, and supplies the DC voltage.

Further, the control unit 285 is connected to the computer 500 through the USB hub 287 and a USB terminal. The computer 500 has a main body 501 including a CPU 502, a memory 503 as a memory portion, and terminals (HDMI, LAN, and USB) for achieving connection to various types of peripheral devices. To a USB terminal, a mouse 504 or a keyboard 505 associated with an input operation to the computer 500 can be connected. Further, to another USB terminal, another barcode reader 506 different from the barcode reader 262 included in the pathological specimen preparation device 200, or a label printer 507 can be connected. To an HDMI terminal, a monitor 508 can be connected. In this embodiment, the display portion 203 with a T/K is included on the pathological specimen preparation device 200 side, and therefore, not only the operation of the pathological specimen preparation device 200, but also exchange with the computer 500 can be performed while confirming the information related to the pathological specimen preparation protocol displayed on the display portion 203. The monitor 508 can display various types of information sent from the computer 500. To a LAN terminal, for example, a network associated with the information management of the pathology department is connected.

The barcode reader 506 is used for reading a barcode given to a reagent container such as a bottle in which the reagent Rs is mainly housed as described in the above-mentioned first embodiment. The computer 500 obtains the information of the reagent Rs from the barcode read and can print a barcode label to be adhered to the cartridge 50R filled with the reagent Rs using the label printer 507.

In the memory 503 of the computer 500, various types of pathological specimen preparation protocols associated with the above-mentioned method for preparing a pathological specimen are stored. The memory 503 in which the pathological specimen preparation protocols are stored may be an internal storage device such as a ROM, a RAM, or an HDD, or an external storage device to be used by being connected to a USB terminal.

An operator designates the pathological specimen preparation protocol stored in the computer 500 through the display portion 203, drives and controls the pathological specimen preparation device 200 by the computer 500 through the display portion 203, and can prepare a pathological specimen. Further, by actually reading the barcode of the cartridge 50R attached to the reagent supply portion 250 with the barcode reader 262, the computer 500 can collate the information of the reagent Rs filled in the cartridge 50R with the information of the reagent Rs in the designated pathological specimen preparation protocol. According to this, management as to whether the reagent Rs to be used in the preparation of the pathological specimen is properly applied can be ensured.

Further, the computer 500 obtains an image of the substrate W captured by the CCD 261 and can perform an operation of associating the image with the designated pathological specimen preparation protocol. According to this, the traceability of the pathological specimen prepared according to the designated pathological specimen preparation protocol can be established. That is, the traceability of the pathological specimen can be improved as compared with the visual confirmation by an operator.

Further, the computer 500 can obtain the information related to the residual amount of the reagent Rs housed in each cartridge 50R by the residual amount detection sensors 263. Therefore, even if there arises a gap between the used amount of the reagent Rs obtained from the pathological specimen preparation protocol and the actually used amount, the management of the reagent Rs, that is, replacement of the cartridge 50R or the like can be properly and accurately performed.

Further, the computer 500 can obtain the information related to the amount of a solution (the washing solution Cs including pure water or a waste liquid thereof) stored in each of the tanks 205 to 208 by the residual amount detection sensors 265. Therefore, even if there arises a gap between the used amount of the washing solution Cs including pure water obtained from the pathological specimen preparation protocol and the actually used amount, the management of the washing solution Cs can be properly and accurately performed. Further, the amount of the waste liquid stored in each of the tanks 205 to 208 can be properly and accurately managed.

Further, by connecting the computer 500 to the network of the pathology department, a series of information related to the pathological specimen preparation can be shared and managed. Incidentally, the configuration of the pathological specimen preparation system 2000 is not limited thereto, and the system may include, for example, another device to be used for a pathological diagnosis such as a device that performs an image analysis of a stained state of a tissue or a cell. Further, the system preferably includes an uninterruptible power supply (UPS) capable of coping with a power failure.

<Immunohistochemical Staining (IHC) Using Frozen Section in Example 4>

Next, Example 4 of pathological specimen preparation using the pathological specimen preparation system 2000 of the second embodiment will be described with reference to FIG. 47. Example 4 is an example of immunohistochemical staining (IHC) using a frozen section in the same manner as in Example 1 described in the above-mentioned first embodiment. FIG. 47 is a table showing a step of preparing a pathological specimen by immunohistochemical staining of Example 4.

As shown in FIG. 47, a step of preparing a pathological specimen by IHC of Example 4 has a first step of fixing a sliced tissue specimen Ts to a substrate W, a second step of washing the fixed tissue specimen Ts, a third step of removing endogenous PO (peroxidase) of the tissue specimen Ts, a fourth step of washing the tissue specimen Ts from which endogenous PO is removed, a fifth step of performing a primary antibody reaction, a sixth step of washing the tissue specimen Ts subjected to the primary antibody reaction treatment, a seventh step of performing a secondary antibody reaction, an eighth step of washing the tissue specimen Ts subjected to the secondary antibody reaction treatment, a ninth step of allowing the washed tissue specimen Ts to develop a color, a tenth step of washing the tissue specimen Ts allowed to develop a color, an eleventh step of subjecting the washed tissue specimen Ts to nuclear staining, a twelfth step of washing the tissue specimen Ts subjected to nuclear staining, a thirteenth step of encapsulating the washed tissue specimen Ts, and a fourteenth step of digitizing the depth of staining by performing an image analysis of the encapsulated tissue specimen Ts. These steps are stored in the memory 503 of the computer 500 as the pathological specimen preparation protocol on the premise that the pathological specimen preparation system 2000 is used. The computer 500 sends a control signal according to the pathological specimen preparation protocol to the control unit 285 of the pathological specimen preparation device 200 in the respective steps from the second step to the twelfth step, and the control unit 285 drives and controls the pathological specimen preparation device 200 so as to perform the treatments in the second step to the twelfth step.

Further, the pathological specimen preparation device 200 of the second embodiment includes the residual amount detection sensors 263 capable of detecting the residual amount of the reagent Rs in the cartridge 50R and the residual amount detection sensors 265 for the solutions (pure water, the washing solution, and the waste liquid) in the tanks 205 to 208. The pathological specimen preparation system 2000 performs a treatment of confirming the residual amounts of the reagents Rs in the respective cartridges 50R using the residual amount detection sensors 263 before starting the pathological specimen preparation. Further, by using the residual amount detection sensors 265, a treatment of confirming the residual amounts of the solutions in the tanks 205 to 208 is performed. Then, with reference to the pathological specimen preparation protocol, it is determined whether the reagent Rs and the washing solution (including pure water) necessary for the pathological specimen preparation to be performed thereafter are ensured. If there are no problems, an operator is informed that the preparation is ready. A notification is displayed on the display portion 203. The operator confirms the notification and starts the pathological specimen preparation. On the display portion 203, a start button for starting the pathological specimen preparation is displayed, and the operator starts the pathological specimen preparation by touching the displayed start button.

On the other hand, in the case where it is determined that the reagent Rs or the washing solution (including pure water) may be running short, the detection result obtained by the residual amount detection sensors 263 is displayed on the display portion 203, and also a warning that urges the operator to replace the cartridge 50R containing the reagent Rs which is running short or to replenish the tank with the washing solution (including pure water) which is running short is displayed on the display portion 203.

Further, in the case where it is determined by the residual amount detection sensors 265 that the tanks 207 and 208 in which the waste liquid is stored may become full by the pathological specimen preparation to be performed thereafter, the state of the waste liquid stored in the tanks 207 and 208 is displayed on the display portion 203, and also a warning that urges the operator to discharge the waste liquid is displayed on the display portion 203. The operator performs a treatment in response to such a warning, and thereafter releases the warning, and then starts the pathological specimen preparation.

By performing the treatment using such residual amount detection sensors 263 and 265, the pathological specimen preparation is prevented from stopping in the middle of the preparation due to a shortage of the reagent Rs or the washing solution or filling up of the tanks 207 to 208 in which the waste liquid is stored during the pathological specimen preparation.

Incidentally, the treatment using such residual amount detection sensors 263 and 265 is not limited to the treatment to be performed before starting the pathological specimen preparation, and may be performed after completing the pathological specimen preparation. Further, the treatment using the residual amount detection sensors 263 and 265 may be performed manually or may be incorporated in the pathological specimen preparation protocol. Then, the process proceeds to the first step.

In the first step of Example 4, as the tissue specimen Ts, a frozen section obtained by slicing a pig liver block is disposed inside the water-repellent ring 2 of the substrate 1, and thereafter the substrate 1 is immersed in acetone for 2 minutes. By doing this, the frozen section is adhered and fixed to the substrate 1. That is, the substrate W having the tissue specimen Ts fixed thereto is obtained. Then, the process proceeds to the second step.

In the second step of Example 4, the substrate W is mounted on the stage 10R of the pathological specimen preparation device 200. The control unit 285 drives and controls the stage transport mechanism (motor 215) so as to transport the stage 10R from the starting point to the washing portion 230 again after once passing through the washing portion 230. In the washing portion 230, the control unit 285 drives and controls the pump P1 and the associated valves so as to eject the washing solution Cs stored in the tank 205 from the nozzle 231 and allowing the washing solution Cs to continuously flow for 30 seconds. As the washing solution Cs, PBS-T (PBS containing Tween 20 which is a nonionic surfactant having a blocking action) is used. In the washing portion 230, washing is performed by supplying PBS-T to the substrate W in a state where the stage 10R is tilted by the stage tilting mechanism. Then, the control unit 285 opens the valve 235 so as to spray air on the substrate W from the nozzle 234 for 1 second. By doing this, PBS-T used for washing goes through the liquid discharge guide portion 226 from the tilted substrate W, and is guided by the flow path switching mechanism 240 and discharged and stored in the tank 207. Then, the process proceeds to the third step.

In the third step of Example 4, the control unit 285 drives and controls the stage transport mechanism (motor 215) so as to transport the stage 10R from the washing portion 230 to the reagent supply portion 250. In the reagent supply portion 250, a reagent (a 3 vol % aqueous hydrogen peroxide solution) for removing endogenous PO is selected according to the pathological specimen preparation protocol. The control unit 285 drives and controls the reagent supply portion 250 (motor 257) so as to transport the cartridge 50R filled with the reagent (3 vol % aqueous hydrogen peroxide solution) to face the substrate W. Then, the control unit 285 drives and controls the electric pusher 258 so as to drop the reagent (3 vol % aqueous hydrogen peroxide solution) onto the substrate W from the cartridge 50R. The dropping amount of the reagent (3 vol % aqueous hydrogen peroxide solution) in this case is, for example, 150 µL (microliters) although it depends on the size of the water-repellent ring 2. After a predetermined amount of the reagent (3 vol % aqueous hydrogen peroxide solution) is supplied to the substrate W, the substrate W is left to stand there for 1 minute, whereby endogenous PO is removed from the tissue specimen Ts (endogenous PO is blocked). Then, the process proceeds to the fourth step.

In the fourth step of Example 4, the control unit 285 drives and controls the stage transport mechanism (motor 215) so as to transport the stage 10R from the reagent supply portion 250 to the washing portion 230. In the washing portion 230, washing with PBS-T is performed in the same manner as in the second step. Then, the process proceeds to the fifth step.

In the fifth step of Example 4, the control unit 285 drives and controls the stage transport mechanism (motor 215) so as to transport the stage 10R from the washing portion 230 to the reagent supply portion 250. In the reagent supply portion 250, a primary antibody reagent (Hep-Par1 which binds to a protein contained in hepatocytes) is selected according to the pathological specimen preparation protocol. The control unit 285 drives and controls the reagent supply portion 250 (motor 257) so as to transport the cartridge 50R filled with the primary antibody reagent to face the substrate W. Then, the control unit 285 drives and controls the electric pusher 258 so as to drop, for example, 150 µL of the primary antibody reagent onto the substrate W from the cartridge 50R. Thereafter, the control unit 285 drives and controls the stage transport mechanism (motor 215) so as to transport the stage 10R from the reagent supply portion 250 to the electric field stirring portion 270. In the electric field stirring portion 270, the control unit 285 generates an electric field between the pair of electrodes 11R and 20 and stirs the solution S of the primary antibody reagent supplied to the substrate W. A time required for the electric field stirring is 5 minutes. Then, the process proceeds to the sixth step.

In the sixth step of Example 4, the control unit 285 drives and controls the stage transport mechanism (motor 215) so as to transport the stage 10R from the electric field stirring portion 270 to the washing portion 230. In the washing portion 230, washing with PBS-T is performed in the same manner as in the second step. Then, the process proceeds to the seventh step.

In the seventh step of Example 4, the control unit 285 drives and controls the stage transport mechanism (motor 215) so as to transport the stage 10R from the washing portion 230 to the reagent supply portion 250. In the reagent supply portion 250, a secondary antibody reagent (EnVision+Dual Link which is a sensitizing reagent using a dextran polymer and peroxidase, manufactured by Dako Co., Ltd.) is selected according to the pathological specimen preparation protocol. The control unit 285 drives and controls the reagent supply portion 250 (motor 257) so as to transport the cartridge 50R filled with the secondary antibody reagent to face the substrate W. Then, the control unit 285 drives and controls the electric pusher 258 so as to drop, for example, 150 µL of the secondary antibody reagent onto the substrate W from the cartridge 50R. Thereafter, the control unit 285 drives and controls the stage transport mechanism (motor 215) so as to transport the stage 10R from the reagent supply portion 250 to the electric field stirring portion 270. In the electric field stirring portion 270, the control unit 285 generates an electric field between the pair of electrodes 11R and 20 and stirs the solution S of the secondary antibody reagent supplied to the substrate W. A time required for the electric field stirring is 5 minutes. Then, the process proceeds to the eighth step.

In the eighth step of Example 4, the control unit 285 drives and controls the stage transport mechanism (motor 215) so as to transport the stage 10R from the electric field stirring portion 270 to the washing portion 230. In the washing portion 230, washing with PBS-T is performed in the same manner as in the second step. Then, the process proceeds to the ninth step.

In the ninth step of Example 4, the control unit 285 drives and controls the stage transport mechanism (motor 215) so as to transport the stage 10R from the washing portion 230 to the reagent supply portion 250. In the reagent supply portion 250, a reagent (3,3'-diaminobenzidine (DAB)) for causing color development is selected according to the pathological specimen preparation protocol. The control unit 285 drives and controls the reagent supply portion 250 (motor 257) so as to transport the cartridge 50R filled with the reagent (DAB) to face the substrate W. Then, the control unit 285 drives and controls the electric pusher 258 so as to drop the reagent (DAB) onto the substrate W from the cartridge 50R. The dropping amount of the reagent (DAB) in this case is, for example, 150 µL. After a predetermined amount of the reagent (DAB) is supplied to the substrate W, the substrate W is left to stand there for 3 minutes so as to allow the tissue specimen Ts and the reagent (DAB) to react with each other and develop a color. Then, the process proceeds to the tenth step.

In the tenth step of Example 4, the control unit 285 drives and controls the stage transport mechanism (motor 215) so as to transport the stage 10R from the reagent supply portion 250 to the washing portion 230. In the washing portion 230, the control unit 285 drives and controls the pump P2 and the associated valves so as to eject pure water stored in the tank 206 from the nozzle 231 and allow pure water to continuously flow for 2 minutes. In the washing portion 230, washing is performed by supplying pure water to the substrate W in a state where the control unit 285 drives and controls the stage tilting mechanism so as to tilt the stage 10R. Then, the control unit 285 opens the valve 235 so as to spray air on the substrate W from the nozzle 234 for 1 second. By doing this, pure water supplied is discharged to the liquid discharge guide portion 226. Pure water used for washing contains the reagent (DAB) containing a carcinogenic substance, and therefore, pure water goes through the liquid discharge guide portion 226 from the tilted substrate W, and is guided by the flow path switching mechanism 240 and discharged and stored in the tank 208. Then, the process proceeds to the eleventh step.

In the eleventh step of Example 4, the control unit 285 drives and controls the stage transport mechanism (motor 215) so as to transport the stage 10R from the washing portion 230 to the reagent supply portion 250. In the reagent supply portion 250, a reagent (hematoxylin) for causing nuclear staining (counterstaining) is selected according to the pathological specimen preparation protocol. The control unit 285 drives and controls the reagent supply portion 250 (motor 257) so as to transport the cartridge 50R filled with the reagent (hematoxylin) to face the substrate W. Then, the control unit 285 drives and controls the electric pusher 258 so as to drop the reagent (hematoxylin) onto the substrate W from the cartridge 50R. The dropping amount of the reagent (hematoxylin) in this case is, for example, 150 µL. After a predetermined amount of the reagent (hematoxylin) is supplied to the substrate W, the substrate W is left to stand there for 1 minute so as to allow the tissue specimen Ts and the reagent (hematoxylin) to react with each other, thereby performing nuclear staining (counterstaining). Then, the process proceeds to the twelfth step.

In the twelfth step of Example 4, the control unit 285 drives and controls the stage transport mechanism (motor 215) so as to transport the stage 10R from the reagent supply portion 250 to the washing portion 230. In the washing portion 230, the control unit 285 drives and controls the pump P2 and the associated valves so as to eject pure water stored in the tank 206 from the nozzle 231 and allow pure water to continuously flow for 2 minutes. In the washing portion 230, washing is performed by supplying pure water to the substrate W in a state where the control unit 185 drives and controls the stage tilting mechanism so as to tilt the stage 10R. Then, the control unit 285 opens the valve 235 so as to spray air on the substrate W from the nozzle 234 for 1 second. By doing this, pure water containing the reagent (hematoxylin) goes through the liquid discharge guide portion 226 from the tilted substrate W, and is guided by the flow path switching mechanism 240 and discharged and stored in the tank 207. Then, the control unit 285 drives and controls the stage transport mechanism (motor 215) so as to transport the stage 10R from the washing portion 230 to the starting point. Then, the process proceeds to the thirteenth step.

In the thirteenth step of Example 4, the substrate W is taken out from the stage 10R, and in order to prevent dryness of the washed tissue specimen Ts, an encapsulation treatment in which a non-water soluble encapsulating agent is dropped onto the substrate W and the tissue specimen Ts is covered with a cover slip is performed. A time required for the thirteenth step is about 1 minute. Then, the process proceeds to the fourteenth step.

In the fourteenth step of Example 4, by using an image analysis device including an image capture portion, an image of the tissue specimen Ts subjected to the encapsulation treatment is captured, and an image analysis is performed, and then, the depth of staining is digitized. A time required for the fourteenth step is about 1 minute. Incidentally, a pathological diagnosis is performed by preparing a tissue specimen Ts with a positive finding and a tissue specimen Ts with a negative finding, and digitizing the depth of staining by an image analysis of each of the specimens, followed by comparison.

By going through the above-mentioned steps, the preparation of the pathological specimen by IHC of Example 4 is completed. A time required for the preparation of the pathological specimen of Example 4 was about 25 minutes.

In the pathological specimen preparation of this embodiment, the treatments can be automatically performed from the second step to the twelfth step using the pathological specimen preparation device 200. Therefore, an operator does not need to monitor the pathological specimen preparation device 200 during this period, and thus can perform another operation during the pathological specimen preparation. However, when a certain time elapses before the process transfers from the twelfth step to the thirteenth step in which the pathological specimen preparation device 200 is not used, the tissue specimen Ts after completion of the nuclear staining treatment may dry on the substrate W mounted on the stage 10R. Therefore, in the pathological specimen preparation system 2000 of this embodiment, the time after the twelfth step is completed is measured, and in the case where the process does not proceed to the thirteenth step even if a predetermined time has elapsed, the control unit 285 drives and controls the stage transport mechanism (motor 215) so as to transport the stage 10R to the washing portion 230. Then, in the washing portion 230, the control unit 285 drives and controls the pump P2 and the associated valves so as to eject, for example, 10 mL (milliliters) of pure water stored in the tank 206 from the nozzle 231 and allow pure water to continuously flow. The control unit 285 drives and controls the stage transport mechanism (motor 215) so as to transport the stage 10R to the starting point. Such a treatment of preventing dryness of the tissue specimen Ts is repeatedly performed according to the period for which the tissue specimen Ts is left before the process transfers to the thirteenth step. In the case where pure water is dropped for preventing dryness, in the above-mentioned thirteenth step, the substrate W is immersed in, for example, ethanol so as to replace pure water with ethanol. Then, ethanol is replaced with xylene, and thereafter, a non-water soluble encapsulating agent is dropped onto the substrate W and the tissue specimen Ts is covered with a cover slip. The non-water soluble encapsulating agent is compatible with xylene. In other words, the washing solution Cs to be dropped from the nozzle 231 for preventing dryness after the twelfth step is completed is preferably pure water which can be easily replaced with ethanol.

In this manner, pure water as the washing solution Cs to be used also for preventing dryness of the tissue specimen Ts is different from ultrapure water to be used in, for example, the production of a semiconductor device, and distilled water sterilized by an autoclave or the like is preferably used.

The pathological specimen preparation using the pathological specimen preparation system 2000 is not limited to immunohistochemical staining (IHC) using a frozen section of the above-mentioned Example 4. It can also be applied to immunohistochemical staining (IHC) using a paraffin-embedded section of Example 2 shown in the above-mentioned first embodiment or in situ hybridization (ISH) shown in Example 3 in the first embodiment. That is, the residual amount of the reagent Rs in the cartridge 50R and the amounts of the solutions in the tanks 205 to 208 are confirmed in advance, and then pathological specimen preparation is started. Further, in the washing step using PBS-T or pure water, the ejected washing solution Cs (containing the reagent Rs in some cases) is reliably discharged by spraying a gas (air) on the tilted substrate W.

According to the pathological specimen preparation device 200 and the pathological specimen preparation system 2000 including the pathological specimen preparation device 200 of the above-mentioned second embodiment, the following effects can be obtained in addition to the same effects as the effects (1), (2), and (6) to (8) of the above-mentioned first embodiment.

(9) The stage tilting mechanism of this embodiment is configured such that by the movement of transporting the stage 10R to the washing portion 230 toward the starting point in the Y direction by the stage transport mechanism, the lever 222 pivotally supported by the first stage support portion 221 rides on the flat plate 214 and rotates counterclockwise, and the tip portion 222*d* of the second arm 222*b* of the lever 222 pushes up the pedestal 12R of the stage 10R. According to this, the stage 10R pivotally supported by the second stage support portion 222 is tilted to the liquid discharge guide portion 226 side. Therefore, a dedicated driving system such as a motor for tilting the stage 10R is not needed, and thus, a simple device configuration can be achieved.

(10) By the stage tilting mechanism, the stage 10R is tilted by an angle within the range of 45° to 60° from the horizontal state of the mounting portion 11R. The washing solution Cs supplied to the substrate W or the washing solution Cs containing the reagent Rs flows in the liquid discharge guide portion 226. Further, air is sprayed on the tilted stage 10R from the nozzle 234, and therefore, the washing solution Cs supplied onto the substrate W can be completely discharged. In other words, a pathological specimen can be properly prepared by reducing or preventing the effect of the washing solution Cs or the washing solution Cs containing the reagent Rs remaining on the substrate W on various types of treatments in the pathological specimen preparation.

(11) The device is configured such that the tilted portion 12*f* which projects to the outside in the X direction is provided in the pedestal 12R of the stage 10R, and when the stage 10R is tilted by the stage tilting mechanism, the tilted portion 12*f* is positioned inside the guide portion 226*b* of the liquid discharge guide portion 226. According to this, even if the washing solution Cs moves to the pedestal 12R side from the mounting portion 11R, the washing solution Cs can be reliably allowed to flow in the liquid discharge guide portion 226. That is, it is possible to prevent the occurrence of a mechanical or electrical problem due to leakage of the washing solution Cs from the stage 10R to a place other than the liquid discharge guide portion 226.

(12) The pathological specimen preparation device 200 includes the residual amount detection sensors 263 that detect the residual amount of the reagent Rs in the cartridge 50R and the residual amount detection sensors 265 that detect the residual amount of the solution stored in each of the tanks 205 to 208. Therefore, the pathological specimen preparation device 200 capable of properly and accurately managing the reagent Rs housed in the cartridge 50R and the solution stored in each of the tanks 205 to 208 can be provided. The pathological specimen preparation system 2000 including the pathological specimen preparation device 200 can obtain the information related to the residual amount of the reagent Rs in each of the cartridges 50R and the information related to the residual amount of the solution stored in each of the tanks 205 to 208. Therefore, interruption of the preparation due to a shortage of the reagent Rs in the middle of the pathological specimen preparation or a shortage of the washing solution Cs including pure water can be prevented. Similarly, interruption of the pathological specimen preparation due to filling up of the tank 207 or 208 in which the waste liquid is stored can be prevented. In other words, the pathological specimen preparation system 2000 capable of performing pathological specimen preparation with confidence without interrupting the pathological specimen preparation in the middle of the preparation can be provided.

(13) In the above-mentioned first embodiment, the CCD 161 as the image capture portion is attached to the timing belt 156 that transports the cartridge holder 155. On the other hand, the CCD 261 as the image capture portion of the image capture unit 260 of the second embodiment can move freely in the X direction independently of the cartridge holder 255 fixed to the timing belt 266. In other words, an image of the substrate W can be captured by transporting the CCD 261 to a given place without being affected by the transport of the cartridge 50R, and therefore, an operation associated with image capture or a load on the device can be reduced.

(14) The pathological specimen preparation system 2000 is configured such that when the substrate W after a nuclear staining treatment is left for a predetermined time, the stage 10R on which the substrate W is mounted is transported to the washing portion 230, and pure water is ejected on the substrate W from the nozzle 231. Therefore, in the twelfth step in which a nuclear staining treatment is performed, dryness of the tissue specimen Ts caused by leaving the substrate W can be prevented. In other words, dryness of the tissue specimen Ts after the nuclear staining treatment can be prevented, and therefore, an operator does not need to monitor the pathological specimen preparation device 200 all the time, and can perform another operation while performing the second step to the twelfth step.

The invention is not limited to the above-mentioned embodiments and appropriate modifications are possible without departing from the gist or idea of the invention readable from the claims and the entire specification, and a pathological specimen preparation device and a pathological specimen preparation system thus modified are also included in the technical scope of the invention. Other than the above-mentioned embodiments, various modification examples can be contemplated. Hereinafter, modification examples will be described.

Modification Example 1

The configuration of the substrate 1 to be used in the pathological specimen preparation is not limited to the configuration including the water-repellent ring 2 on the substrate 1 shown in FIG. 1. Hereinafter, a modification example of the substrate 1 will be described with reference to FIG. 48 to FIG. 50. FIG. 48 to FIG. 50 are each a schematic plan view showing a configuration of a substrate of a modification example. For example, as shown in FIG. 48, it may be configured such that two water-repellent stickers 2a and 2b are adhered onto the substrate 1. Each of the two water-repellent stickers 2a and 2b has a circular opening portion. Further, the two water-repellent stickers 2a and 2b are connected to each other through a connection portion 2c having a narrower width than the width of the substrate 1. In other words, by the connection portion 2c, a necessary number of water-repellent stickers are cut off at the connection portion 2c from a plurality of water-repellent stickers connected to one another through the connection portion 2c and adhered to the substrate 1. Each water-repellent sticker is formed with the same width as the width of the substrate 1, and therefore, the reagent Rs or the washing solution Cs dropped onto the substrate 1 can be easily discharged by tilting the substrate 1.

Further, for example, as shown in FIG. 49, a water-repellent sticker 2d may be formed so as to surround a predetermined quadrangular region on the substrate 1. According to this, a region where the tissue specimen Ts is disposed can be ensured larger than the water-repellent ring 2. In other words, even if the water-repellent ring 2 in accordance with the size of the tissue specimen Ts is not prepared, the preparation of a pathological specimen can be performed.

Further, for example, as shown in FIG. 50, a water-repellent sticker 2e in which one long side portion on the side to which the stage 10 is tilted is eliminated from the water-repellent sticker 2d in FIG. 49 may be adopted. According to this, the reagent Rs or the washing solution Cs dropped onto the substrate 1 can be easily discharged by tilting the substrate 1 by the stage 10.

Modification Example 2

In the pathological specimen preparation device 200 of the above-mentioned second embodiment, the shape of the stage 10R on which the substrate W having the tissue specimen Ts fixed thereto is mounted is not limited thereto. FIG. 51 is a schematic perspective view showing a stage of a modification example. As shown in FIG. 51, a stage 10RB of the modification example is made different from the above-mentioned stage 10R in the form of a notched portion. More specifically, the stage 10RB has a mounting portion 11RB on which the substrate W is mounted and a pedestal 12RB which supports the mounting portion 11RB from the lower side. The mounting portion 11RB has a guide portion 11a, a guide portion 11b, a guide portion 11e, and a guide portion 11f for mounting the substrate W at a predetermined position in the X direction and the Y direction. The guide portion 11a is provided on the right-side side in the X direction and a rear end side in the Y direction of the mounting portion 11RB. The guide portion 11b is provided at the front left corner of the mounting portion 11RB, and the guide portion 11f is provided at the front right corner of the mounting portion 11RB. On the left-side side in the X direction of the mounting portion 11RB, a tilted portion 11d is provided. Further, the guide portion 11e which is formed integrally with the guide portion 11a and extends along the tilted portion 11d is provided. The mounting portion 11RB has a notched portion 11h which is notched between the guide portion 11b and the guide portion 11f on the front side, and also the pedestal 12RB has a notched portion 12h which is notched on the front side where the guide portion 11b and the guide portion 11f are overlapped with each other. These notched portions 11h and 12h are notched so that when the substrate W is set or reset with respect to the mounting portion 11RB by grasping an end of the substrate W with, for example, forceps or the like, the forceps do not come into contact with the pedestal 12RB even if an operator grasps the forceps with the left hand or the right hand. That is, it is configured such that setting or resetting of the substrate W with respect to the stage 10RB can be easily performed. Incidentally, the configuration of the other portion of the stage 10RB is the same as that of the above-mentioned stage 10R.

Modification Example 3

In the color development step of the above-mentioned Example 1 to Example 4, DAB to be used is not limited to one type. For example, a color development buffer reagent (DAB1) and a concentrated color development reagent (DAB2) may be used. The ratio of DAB1 to DAB2 is appropriately set.

Modification Example 4

In the pathological specimen preparation in ISH of the above-mentioned Example 3, the pathological specimen preparation device 100 is not used in the first step (deparaffinization) to the fourth step (washing), however, in the reagent supply portion 150, if the dropping amount of the reagent Rs to be dropped from the cartridge 50 can be more accurately adjusted, it is possible to perform the treatment using the pathological specimen preparation device 100 or the pathological specimen preparation device 200 also in the first step (deparaffinization) to the fourth step (washing).

The invention claimed is:

1. A pathological specimen preparation device, comprising:
   three directions orthogonal to each other being defined as a first direction, a second direction, and a third direction;
   a stage on which a substrate is mounted, the substrate having a tissue specimen fixed thereto;
   a first motor configured to move the stage along the first direction via a first drive mechanism;
   a support rod abutting on a bottom of the stage, the support rod being configured to push the stage upward along the second direction via a second drive mechanism so as to rotate the stage toward the third direction and around a rotation axis, the rotation axis being parallel to the first direction;
   a reagent supply device having a plurality of cartridges, each of the plurality of cartridges having a nozzle, the plurality of cartridges storing a plurality kind of reagents, respectively, that are different from each other, one of the plurality kind of reagents being supplied to the substrate via a corresponding one of the plurality of nozzles from a corresponding one of the plurality of cartridges;
   a washing device having a tank and a washer nozzle, the tank storing a washing solution that is supplied to the substrate via the washer nozzle;
   an electric field stirring device having first and second electrodes, the electric field stirring device being configured to generate an electric field between the first and second electrodes that is applied to the reagent or the washing solution supplied to the substrate to stir the reagent or the washing solution around the substrate; and
   a controller configured to control the stage device, the first motor, the reagent supply device, the washing device, and the electric field stirring device to prepare a pathological specimen,
   wherein the washing device, the reagent supply device, and the electric field stirring device are sequentially disposed on a frame of the pathological specimen preparation device along the first direction through which the stage moves,
   the first electrode of the electric field stirring device is provided to face the stage, and a groove is formed across a surface of the first electrode,
   the controller is configured to cause the support rod to push the bottom of the stage so as to rotate the stage when the stage is positioned in the washing device, and the controller is configured to select one of the plurality kind of reagents and determine a period of time during which the electric field generated between the first and second electrodes is applied to the reagent or the washing solution around the substrate according to a pathological specimen preparation protocol.

2. The pathological specimen preparation device according to claim 1, wherein the stage is rotated by 60° or more toward the third direction from a horizontal state via the support rod.

3. The pathological specimen preparation device according to claim 1, wherein
   the stage is configured with a plurality of stages that are arranged in parallel in the first direction, and each of the plurality of stages has the substrate,
   the reagent supply device supplies the reagent to the substrate mounted on each of the plurality of stages,
   the washing device supplies the washing solution to the substrate mounted on each of the plurality of stages,
   the first electrode of the electric field stirring device is provided across the plurality of stages in the first direction.

4. The pathological specimen preparation device according to claim 1, wherein
   the reagent supply device includes a plurality of holders, a second motor, a pulley, and a timing belt, the plurality of holders hold the plurality of cartridges, respectively, and the second motor is configured to move the plurality of holders via the pulley and the timing belt, and
   the controller is configured to control the second motor to drive the plurality of holders according to the pathological specimen preparation protocol so as to move at least one of the plurality of holders to a position opposed to the stage.

5. The pathological specimen preparation device according to claim 4, further comprising:
   a barcode reader,
   wherein each of the plurality of cartridges has a barcode, and
   the controller is configured to cause the barcode reader to read the barcodes on the plurality of cartridges so as to move at least one of the plurality of holders to the position opposed to the stage.

6. The pathological specimen preparation device according to claim 4, further comprising:
   a residual amount detection sensor configured to detect presence or absence of the reagent in each of the plurality of cartridges,
   wherein each of the plurality of cartridges has a light transmissive housing, and
   the residual amount detection sensor is configured to optically detect the presence or absence of the reagent through the light transmissive housing.

7. The pathological specimen preparation device according to claim 1, wherein
   the tank of the washing device is configured with a plurality of tanks,
   the washing device further includes a valve configured to switch connection destination of the nozzle to the plurality of tanks, and
   the controller is configured to control the valve according to the pathological specimen preparation protocol so as to connect the nozzle to one of the plurality of tanks.

8. The pathological specimen preparation device according to claim 7, wherein pure water is filled in one of the plurality of tanks as the washing solution.

9. The pathological specimen preparation device according to claim 1, wherein
the washing device further includes a gas nozzle connected to a gas supply source through a gas valve, and
the controller is configured to control opening and closing of the gas valve according to the pathological specimen preparation protocol so as to spray a gas on the substrate mounted on the stage from the gas nozzle when the stage is positioned in the washing device.

10. The pathological specimen preparation device according to claim 1, further comprising:
a waste liquid tank, and
a discharge flow path that discharges the reagent or the washing solution flowing down from the substrate on the rotated stage toward the waste liquid tank when the stage is positioned in the washing device.

11. The pathological specimen preparation device according to claim 10, further comprising:
a flow path switching mechanism configured with a third motor and a rotation shaft,
wherein the waste liquid tank is configured with a first waste liquid tank and a second waste liquid tank,
the discharge flow path is configured with a first discharge flow path toward the first waste liquid tank and a second discharge flow path toward the second waste liquid tank,
the flow path switching mechanism is configured to switch discharge destination of the reagent or the washing solution flowing down from the substrate on the rotated stage to flow in between the first discharge flow path and the second discharge flow path by rotating the rotation shaft by the third motor, and
the controller is configured to control the flow path switching mechanism depending on a type of the reagent or the washing solution according to the pathological specimen preparation protocol so as to switch the discharge destination of the reagent or the washing solution between the first discharge flow path and the second discharge flow path.

12. The pathological specimen preparation device according to claim 1, further comprising:
an image capture sensor configured to capture an image of the substrate mounted on the stage.

13. The pathological specimen preparation device according to claim 1, further comprising:
a display configured to display information related to the pathological specimen preparation protocol; and
an input interface associated with an operation of the pathological specimen preparation protocol.

14. A pathological specimen preparation system, comprising:
the pathological specimen preparation device according to claim 1; and
a computer having a memory that stores the pathological specimen preparation protocol, wherein
the computer is configured to control the pathological specimen preparation device according to the pathological specimen preparation protocol.

15. The pathological specimen preparation system according to claim 14, wherein
the regent is filled in one of the plurality of cartridges having a barcode, and
the computer is configured to obtain information of the reagent associated with the barcode of the one of the plurality of cartridges and collate the information of the reagent associated with the barcode with information of the reagent according to the pathological specimen preparation protocol.

16. The pathological specimen preparation system according to claim 14, wherein
each of the plurality of cartridges has a light transmissive housing,
the pathological specimen preparation device includes a residual amount detection sensor that is configured to detect presence or absence of the reagent in each of the plurality of cartridges,
the residual amount detection sensor is configured to optically detect the presence or absence of the reagent through the light transmissive housing, and
the computer is configured to detect a residual amount of the reagent with the residual amount detection sensor at least before starting preparation of the pathological specimen according to the pathological specimen preparation protocol.

17. The pathological specimen preparation system according to claim 14, wherein the computer is configured to transport the substrate to the washing device and allow pure water as the washing solution to be supplied to the substrate from the washing device according to the pathological specimen preparation protocol when a standing time after the tissue specimen fixed to the substrate is allowed to develop a color and then washed reaches a predetermined time.

18. The pathological specimen preparation system according to claim 14, wherein
the computer is configured to obtain an image of the substrate and the tissue specimen fixed to the substrate, and
the computer is configured to perform an operation of associating the obtained image with the pathological specimen preparation protocol.

* * * * *